US012773225B2

(12) United States Patent
Shifflette

(10) Patent No.: US 12,773,225 B2
(45) Date of Patent: Oct. 27, 2026

(54) TIME DOMAIN VISCOMETRY

(71) Applicant: J. Michael Shifflette, Alachua, FL (US)

(72) Inventor: J. Michael Shifflette, Alachua, FL (US)

( * ) Notice: Subject to any disclaimer, the term of this patent is extended or adjusted under 35 U.S.C. 154(b) by 721 days.

(21) Appl. No.: 18/128,224

(22) Filed: Mar. 30, 2023

(65) Prior Publication Data

US 2024/0325035 A1 Oct. 3, 2024

Related U.S. Application Data

(60) Provisional application No. 63/347,005, filed on May 30, 2022, provisional application No. 63/325,614, (Continued)

(51) Int. Cl.
*A61B 17/22* (2006.01)
*G01N 11/08* (2006.01)
(Continued)

(52) U.S. Cl.
CPC .... *A61B 17/22* (2013.01); *A61B 2017/00292* (2013.01); *A61B 2017/00725* (2013.01); (Continued)

(58) Field of Classification Search
CPC .......... A61B 17/22; A61B 2017/00292; A61B 2017/00725; A61B 2017/22079; A61B 2090/064; A61B 17/3207; A61B 2017/00022; A61B 2017/00115; A61B 2017/0019; A61B 5/02035; A61B 17/00491; A61B 2017/00004; A61B 8/12; A61B 17/07292; A61B 5/6866;
(Continued)

(56) References Cited

U.S. PATENT DOCUMENTS 5,720,721 A 2/1998 Dumas et al.
9,563,198 B2 2/2017 Anup et al.
(Continued)

OTHER PUBLICATIONS

Non-Final Rejection Mailed on Oct. 22, 2025 for U.S. Appl. No. 18/128,600, 6 page(s).

*Primary Examiner* — Andre J Allen
(74) *Attorney, Agent, or Firm* — Kaplan Breyer Schwarz, LLP

(57) ABSTRACT

Time domain viscometry is disclosed in the context of a thrombectomy system, wherein the aspirate composition may span saline (≈1 cP) and blood (≈4 cP) to blood/thrombus mixtures (~10 cP to ~10,000 cP) to a clog (>10,000 cP). An objective of a suction thrombectomy system is to aspirate low-viscosity blood at low suction levels concomitantly with aspirating high-viscosity thrombus at high suction levels. Time domain viscometry comprises measuring the time required for fluids of differing viscosities to flow into an elastically deformed conduit. One or more fluid standards (e.g., saline, blood, etc.) may be used for in-situ calibration of the viscometer. Ratiometric analysis of the resulting measurements permits time domain differential viscometry wherein the viscosity of an unknown fluid is determined with respect to a fluid of known viscosity. Viscometric thrombectomy systems are enabled to discriminate between blood and thrombus and adjust the aspiration rate accordingly.

20 Claims, 22 Drawing Sheets

Related U.S. Application Data filed on Mar. 31, 2022, provisional application No. 63/326,040, filed on Mar. 31, 2022.

(51) Int. Cl.
*A61B 17/00* (2006.01)
*A61B 90/00* (2016.01)

(52) U.S. Cl.
CPC ............... *A61B 2017/22079* (2013.01); *A61B 2090/064* (2016.02); *A61M 2205/3334* (2013.01); *A61M 2205/3344* (2013.01); *A61M 2205/70* (2013.01)

(58) Field of Classification Search
CPC .. A61M 2205/3334; A61M 2205/3344; A61M 2205/70; A61M 37/0015; A61M 37/00; A61M 2037/0053; A61M 2037/0023; A61M 2037/0046; A61M 35/003; A61M 31/00; A61M 15/08; A61M 35/00; A61M 5/315; A61M 5/20; A61M 2205/8206; A61M 31/002; A61M 5/14276; A61M 2005/14513; A61M 11/00; A61M 11/007; A61M 60/422; A61M 2207/00; A61M 5/19; A61M 5/31; A61M 5/3202; A61M 60/232; A61M 2037/0061; A61M 5/2033; A61M 2210/0618; A61M 5/30; A61M 5/1723; G01N 11/08
See application file for complete search history.

(56) References Cited

U.S. PATENT DOCUMENTS

| | | | | |
|---|---|---|---|---|
| 11,197,683 | B1 | 12/2021 | Teigen et al. | |
| 11,716,880 | B2 | 8/2023 | Lee | |
| 11,730,499 | B1 * | 8/2023 | Thio | A61B 17/22 604/508 |
| 12,156,666 | B2 * | 12/2024 | Trosper | A61B 17/22 |
| 12,156,667 | B2 * | 12/2024 | Trosper | A61B 17/22 |
| 12,239,777 | B2 * | 3/2025 | Su | A61B 17/320758 |
| 12,496,076 | B2 * | 12/2025 | Trosper | A61B 17/22 |
| 2007/0126592 | A1 | 6/2007 | Littrell | |
| 2007/0196213 | A1 | 8/2007 | Parsons et al. | |
| 2017/0173262 | A1 * | 6/2017 | Veltz | G16H 20/17 |
| 2019/0143469 | A1 | 5/2019 | Coleman | |
| 2021/0109158 | A1 | 4/2021 | Manson et al. | |
| 2021/0324955 | A1 | 10/2021 | Zhu et al. | |
| 2021/0404854 | A1 | 12/2021 | Patel et al. | |
| 2022/0025891 | A1 | 1/2022 | Abhyankar et al. | |
| 2022/0326666 | A1 | 10/2022 | Ubert et al. | |

* cited by examiner

*Prior Art*

*Prior Art*

*Prior Art*

Prior Art $-\ln\left(\frac{P}{P_0}\right)$ vs $\frac{t}{\tau_{saline}}$

Time decay of Pressure, Flow and Displacement Volume time > ≈ 5τ time = 0

*Prior Art*

Fig. 16c

Column 1 480

Row 1 485

| | Water | Vinegar | Creamer | Cream Hot | Veg Oil | Cream Cold | ATF | Visc Factor |
|---|---|---|---|---|---|---|---|---|
| Slope | 71.7 | 61.3 | 34.2 | 18.6 | 4.1 | 3.3 | 1.8 | |
| Norm Slope | 1.000 | 0.855 | 0.477 | 0.260 | 0.058 | 0.045 | 0.025 | |
| 1/(Norm Slope) | 1 | 1.2 | 2.1 | 3.8 | 17.3 | 22.0 | 39.8 | VF1 |
| Min Pressure | 277.1 | 277.6 | 266.9 | 255.8 | 226.3 | 241.8 | 235.9 | |
| Pressure Factor | 1 | 1.00 | 1.04 | 1.08 | 1.22 | 1.15 | 1.17 | VF2 |
| Range | 79.2 | 68.2 | 38.9 | 21.1 | 5.3 | 4.3 | 3.0 | VF3 |
| | 1 | 1.2 | 2.2 | 4.3 | 32.8 | 34.5 | 75.8 | VF1^VF2 |
| | 1 | 1.2 | 2.2 | 4.2 | 21.2 | 25.2 | 46.8 | VF1xVF2 |

Fig. 16d

| | Water | Vinegar | Creamer | Cream Hot | Veg Oil | Cream Cold | ATF |
|---|---|---|---|---|---|---|---|
| 101 | 279.4 | 280.0 | 269.2 | 257.0 | 227.8 | 242.9 | 238.6 |
| 102 | 278.9 | 278.6 | 266.9 | 256.7 | 227.0 | 242.7 | 236.9 |
| 103 | 277.1 | 277.6 | 267.6 | 255.8 | 226.3 | 241.8 | 235.9 |
| 104 | 280.2 | 280.2 | 268.9 | 257.1 | 226.8 | 242.3 | 236.1 |
| 105 | 282.7 | 282.7 | 270.2 | 258.1 | 226.9 | 242.0 | 236.2 |
| 106 | 285.1 | 284.5 | 272.1 | 258.6 | 227.2 | 242.4 | 236.5 |
| 125 | 343.7 | 333.5 | 297.8 | 272.8 | 230.3 | 244.8 | 238.5 |
| 126 | 346.0 | 335.7 | 299.6 | 273.8 | 230.4 | 245.3 | 238.1 |
| 127 | 348.2 | 338.1 | 301.5 | 274.9 | 231.0 | 245.2 | 238.5 |
| 128 | 352.2 | 341.8 | 302.8 | 275.8 | 231.6 | 245.7 | 238.8 |
| 129 | 354.0 | 344.0 | 304.1 | 276.5 | 231.0 | 245.7 | 238.4 |
| 130 | 356.3 | 345.8 | 305.8 | 276.9 | 231.5 | 246.1 | 238.9 |

Difference ∝ ATF Slope

Difference ∝ Water Slope

Difference ∝ Creamer Slope

Difference ∝ Veg Oil Slope

TIME DOMAIN VISCOMETRY

STATEMENT OF RELATED CASES

This case relates to U.S. patent application Ser. No. 17/409,635 filed Aug. 23, 2021, Provisional U.S. Pat. Applications 63/326,040, filed Mar. 31, 2022, 63/347,005, filed May 30, 2022, and 63/325,614 filed Mar. 31, 2022, all of which are incorporated by reference herein.

FIELD OF THE INVENTION

The present invention relates to thrombectomy and viscometry.

BACKGROUND INFORMATION

Suction thrombectomy systems employ differential pressure to aspirate thrombus; this differential pressure may arise from a number of sources including an evacuated reservoir or a liquid pump. A problem with suction thrombectomy systems is blood loss because blood flows rapidly while thrombus flows slowly under the same differential pressure conditions.

Viscosity may be measured in batch process viscometers such as rotational viscometers (e.g., Brookfield), capillary tube viscometers, falling ball viscometers and vibration viscometers. The first three listed examples are limited to batch processes, whereas vibration viscometers are suited for flow processes.

SUMMARY OF THE INVENTION

The present invention provides a thrombectomy system and operational methods therefor that avoid the shortcomings of the prior art. In accordance with the present teachings, time-domain mathematical techniques are disclosed that transform variable data from the measured parameters or properties (e.g., pressure, temperature, etc.) to a quantitative determination of a secondary parameter or property (e.g., viscosity, flow, heat transfer, etc.). Time rate-of-change analyses (of measured fluid property data) are disclosed herein that quantitatively measure or determine viscosity by evaluating changes in pressure (the dependent variable, ordinate or range) with respect to time (the independent variable, abscissa, or domain). Aspects of the present invention include field or in-situ calibration of thrombectomy systems; this calibration provides accurate experimental data which is collected upon: sampled fluids (e.g., saline, reference fluids, patient bloodstream, etc.) and the equipment (e.g., thrombectomy system, peristaltic pump, etc.) at the time of the procedure.

Prior art efforts in thrombectomy systems are limited to collecting and analyzing fluid property data and subsequently describing fluid flow in attribute terms including: flow, thrombus, clot or clog, etc. The present invention furthers these efforts in no fewer than two important distinctions: (1) the quantification of fluid properties such as viscosity and flow as variable data and (2) the measurement of a first fluid property (pressure) and quantitative determination of additional fluid properties (viscosity and flow).

U.S. Pat. No. 11,197,683 (the '683 patent) discloses embodiments and a methodology to sense flow; the disclosed system employs two pressure sensors acting as a flowmeter. The '683 patent further discloses an algorithm in FIG. 13 to "sense flow" which executes conditional statements (e.g., IF ($\Delta P > X^*\Delta P\text{max}$) OR IF ($\Delta P < \Delta P\text{min}$) THEN close valve) to intermittently open and close a valve to reduce the aspiration of viable blood; where X is an undisclosed "confidence multiplier." Also not disclosed is the "Lower threshold for $\Delta P = \Delta P\text{min}$," or the "Optimized sample period, T." This algorithm may be intended to rapidly aspirate (leave the valve open) thrombus-laden blood with uninterrupted vacuum while slowly aspirating viable blood with interrupted vacuum (intermittently closing the valve). However, there are 2 or 3 arbitrary constants (X, T and ΔPmin) affecting the outcome of these conditional statements. Changes to these arbitrary constants may allow the outcomes of the conditional statement to be biased in favor of a preferred or otherwise erroneous outcome; for instance, if X (Confidence Multiplier) is (too) large, then the outcome of the algorithm iteration will be biased toward ("Stay Open Until Next Sample") whereupon the valve remains open (until the next sample). Similarly, if ΔPmin is (too) small, then the outcome of the algorithm iteration will be similarly biased. However, if X (Confidence Multiplier) is (too) small and ΔPmin is also (too) small, then the outcome of the algorithm will be biased toward ("Stay Closed Until Next Sample"). Therefore, the '683 algorithm is not robust to any change in the stated arbitrary constants; furthermore, the derivation, ranges or calculation of these arbitrary constants are not disclosed. The '683 convention of using symbol ΔP (upper case) to denote the measurement difference between two pressure sensors (located a distance apart from one another) has been preserved in the preceding section, hereinafter, this measured quantity may be referred as Δp (lower case).

The position and distance between the pressure sensors is not disclosed in the '683 patent, and a "connecting tube" separates the two; therein, differential pressure is measured concomitantly at two locations separated by an undisclosed distance through a tube of undisclosed diameter. The flowmeter disclosed in the '683 patent consists of two pressure sensors separated by a length of tubing. The '683 patent employs the term "near full vacuum" and provides the definition as: "near-29.9 inHg." This vacuum is provided by a vacuum pump which evacuates air from a vacuum reservoir.

U.S. Pat. No. 11,716,880 (the '880 patent) discloses, in FIG. 5*a* through FIG. 5*d*, pressure traces; regions of decreasing slope 99 and increasing slope 83, 95 are identified, along with the steady pressure curve 97. In the four depictions, decreasing slope 99, steady pressure curve 97 and increasing slope 83, 95 are indistinguishable between the figures. Furthermore, depictions of the "regions of decreasing slope" 99 are actually regions of increasing slope. At the left-most end of the graph (time=0?), the pressure is approximately zero and decreasing at the greatest rate (slope is large and negative at time=0). As time approaches approximately 10 seconds, the slope remains negative but was continuously increasing in value over the first approximately 10 seconds. In the '880 patent, "regions of decreasing slope" 99 would be better described as "regions of decreasing pressure;" the slope is shown to be continuously increasing. Similarly, "regions of increasing slope" 83, 95 are shown to be "regions of increasing pressure"; while the slope is generally shown to be increasing, no attempts are made to quantify the slope of the pressure traces.

In FIG. 5A through FIG. 5*d* of the '880 patent, the time axis (abscissa, x or t axis) remains constant in all depictions scaled to 60 seconds, and the event time frame may be estimated to be in the range of 25 to 50 seconds. The pressure axis (ordinate, or y axis) is labeled at zero; no units or hash marks are provided on the pressure axis; the minimum pressure appears to be consistent among the figures. A pressure difference 81 is shown in FIG. 5*b* and pressure deviations 77, 73 are shown in FIG. 5*d* to occur on a time scale of duration 65. Both the pressure deviations 77, 73 and the time duration 65 are correlated to reference values stored in memory. The stated range for this time duration 65 is disclosed to be between 0.001 s and 0.5 s which is subdivided into 4 different ranges for 4 different embodiments; there is no stated range for pressure difference 81.

Both the '683 and the '880 patents utilize algorithms which invoke reference/library data and/or arbitrary constants (e.g., pre-set values stored in the memory module 56) to assess any collected experimental pressure data and make non-quantitative, or characteristic inferences, e.g., flow, thrombus, clot or clog, etc. These inferences produce attribute data by comparison with reference data from databases, libraries, user-defined arbitrary constants and artificial intelligence. The '880 patent measures pressure traces which are compared to reference data stored in memory modules in order to describe the aspirate in attribute terms. Both the '683 and the '832 patents thereby utilize reference data which are typically: (1) not collected upon the thrombectomy system in use, (2) not collected at the time of use, and/or (3) not collected upon the patient under treatment. In order to determine a thrombectomy operating mode, prior art thrombectomy systems may employ conditional statements with patient data, reference data and arbitrary constants as arguments. These arbitrary constants may bias the outcome of conditional statements such that preferred or otherwise erroneous outcomes result.

Co-pending U.S. patent application Ser. No. 17/409,635, Provisional U.S. Pat. Applications 63/326,040, and 63/347,005, disclose the utilization of a peristaltic pump as a viscometer; embodiments include operating the combination of a peristaltic pump and pressure transducer to form a viscometer for quantitatively measuring the viscosity of aspirate in a thrombectomy system. Embodiments include operating a peristaltic pump at a plurality of speeds and measuring the inlet pressure to the pump. A mathematical function may be curve-fit to calibration data (e.g., saline, blood, oil, etc.) or a calibration database may be created in tabular form.

Aspects of the present invention further disclose the use of homogeneous, variable data (including homogeneous patient data) as calibration data; subsequent heterogeneous patient data may then be quantitatively analyzed with respect to calibration data instead of reference data. These calibration data may be collected as an integral, ancillary, initial, intermediate, preparatory function of a thrombectomy procedure. Prior art techniques for evaluation and/or monitoring of patient data vs. reference data may generate results in attribute data and/or descriptive terms (e.g., thick, viscous, clot, clog, etc.). The present invention enables quantitative determination of patient data vs. calibration data which may result in variable data in engineering units (e.g., 10% pressure, 200% time, 20 cP, 5 cc/min, etc.). Variable data in engineering units may be readily converted to attribute data in descriptive characteristic terminology, however this process is degenerative and not reversible. Attribute data are used effectively by statisticians using descriptive terms such as: gender, ethnicity, color, yes/no, pass/fail, etc.; large sample sizes enable statisticians to make valid statistical inferences from these data. Attribute data may be also referred to as "counting data" because it may be used most effectively by counting the number of occurrences of a particular attribute or characteristic; statistical inferences may thereby be made using attribute data of sufficient sample size (i.e., a sufficient number of counts or occurrences).

A thrombectomy system may "sample" the process fluid (blood and/or thrombus) continuously or at periodic (regular, sequential, intermittent, etc.) intervals (e.g., pressure measurement, flow measurement, viscosity measurement, temperature, opacity, conductivity, etc.). In a thrombectomy system each "sample" is "snapshot in time" of the measured parameter (pressure, flow, viscosity, temperature, etc.). A thrombectomy system may be designed to sense or measure any aspirate either quantitatively or characteristically (e.g., pressure, flow, viscosity, etc.), and to subsequently make a control system response decision regarding whether or not to update a system setpoint (e.g., change a setting, change a pump speed, open a valve, close a valve, etc.). Therefore, each measurement "sample" is a sample size of 1 and a decision may be made based upon each sample. A methodology for an example thrombectomy system, using attribute data, may be to continuously, sequentially or intermittently sample the aspirate, each sample being of sample size 1; then to transform the variable data to attribute data (e.g., pressure <5 psi, flow>1 cc/second, temperature above 30° C., yes, pass, etc.), and to subsequently monitor the attribute data for a change in the measured or sensed characteristic. An example is: (IF characteristic(i)< >characterist(i+1) THEN increase pump speed by X %), where X % is an arbitrary constant. In contrast, the conditional statement (IF characteristic (i)<characteristic (i+1) THEN . . . ) generally may not be evaluated because characteristic (j) is an attribute or characteristic expressed in words and not a numeric variable which may be compared quantitatively to any other characteristic (k). i, j and k are loop index counters, and so events i, i+1, j and k generally occur at different times as may occur in a thrombectomy procedure wherein continuous, sequential or intermittent aspirate sampling is conducted. If a change in attribute data is detected (e.g., pressure>5 psi, flow<1 cc/second, temperature below 30° C., no, fail, etc.) then the example thrombectomy system may change a system setpoint by an arbitrary amount as determined by an arbitrary constant. The example threshold values of 5 psi, 1 cc/second, 30° C., etc. are also examples of arbitrary constants invoked in determining the control system response. Such a system may not be robust to changes in the value of the arbitrary constants invoked. Attribute data (and arbitrary threshold constants) may be of statistical value with large sample sizes; however the sample size for a thrombectomy procedure is generally one. Attribute data may be most useful only when the sample size is large (a large number of observations must occur) and statistical inferences may be made. In a thrombectomy procedure, each such "observation" generally discharges a finite volume of patient blood to waste; this collectively may cause exsanguination of the patient. Therefore, each evaluation of attribute data occurring in a thrombectomy procedure is generally is of sample size one. Algorithms may exist that count the number of occurrences such as: (IF P>P* five consecutive times THEN . . . ), where P* and five are arbitrary constants. While such an algorithm may increase the sample size to five, this also introduces an additional arbitrary constant (in this example case case, five), this algorithm may discharge five sample volumes of patient blood to waste before a control system response occurs.

An aspect of the present invention is to collect homogeneous calibration data (e.g., saline, blood, calibration standards, etc.) and heterogeneous patient data (e.g., blood, thrombus, clot, clog, etc.) which may be quantitatively analyzed to measure fluid properties including viscosity, flow and/or delivered volume. Data from an analytical instrument, such as a pressure transducer, supplies data in characteristic units; in this case: pressure. Prior art includes the measurement of pressure, or differential pressure, in thrombectomy systems, however pressure data alone is of little use without an apparatus and method to convert or transform intensive pressure data to extensive fluid property data, such as flow.

Another aspect of the present invention is to invoke coordinate transformations upon dimensional data which may transform the data to be dimensionless or otherwise change the dimensions to another set of dimensions. Dimensions may be herein presented in Force/Length/Time fundamental units and expressed as [FLT], each fundamental unit may be raised to a power; examples include: pressure [$FL^{-2}$], volumetric flow rate [$L^3T^{-1}$], viscosity [$FL^{-2}T$], etc. Dimensional data may be transformed to dimensionless data by dividing any quantity by another quantity of the same dimensions; this ratio is dimensionless. This is distinct from unit conversion wherein data in a first set of units is converted into data in a second set of units. Coordinate transformations may facilitate the use of differential & integral calculus and/or differential equations (herein in time domain) to solve the governing equations or mathematical model identified to elicit any desired quantities (e.g., flow, delivery volume and viscosity). Coordinate transformations may facilitate the rapid determination of the initial conditions for differential equations to be solved. The present invention discloses the incorporation of one or more extensive properties (to the governing equations or mathematical models) to evaluate the rate of change of an intensive property (e.g., pressure, temperature, conductivity, etc.) with respect to an extensive property (e.g., time, mass, length, volume, etc.). A representative embodiment may include any or all of steps: (1) collecting pressure data, (2) non-dimensionalizing the pressure data, (3) taking the time derivative of the non-dimensionalized pressure data, (4) measuring a (slope) parameter (having the dimensions of inverse time), (5) calculating a time constant (t) for the pressure data (having the dimensions of time), (6) calculating a viscosity, flow or delivery volume as a function of the time constant, the units of the viscosity and/or flow being consistent with the dimensions of the selected engineering units. An aspect of the present invention may comprise the collection of data in a first set of units and dimensions and then to subsequently calculate parameters in a second set of units and dimensions. For example, data may be collected in units and dimensions of pressure and time; the mathematical techniques of the present invention may facilitate manipulation of this data to measure parameters in different units and dimensions, e.g., viscosity and/or flow rate. Non-dimensionalization of any data at any step is optional and is incorporated in preferred embodiments and disclosed examples for clarity and as a convenience.

Fundamental to subsequent analyses is an understanding of differential pressure flow measurement and flowmeters. A working equation for a differential pressure flowmeter (for flow in a pipe) is given in eq. 1, which is a simplified form of the inviscid momentum equation, also known as Bernoulli's equation.

$$Q = k\sqrt{\Delta p} \qquad \text{Eq. 1}$$

Where Q is the volumetric flow rate in the pipe, Δp (lower case) is the differential pressure across an orifice, restriction, venturi, length of pipe, etc. and k is a (dimensioned) calibration constant (which may be calculated for some flowmeters, or experimentally determined). Δp is a (simultaneous, concurrent, instantaneous) difference in pressure measurements separated by a distance or length. In a differential pressure flowmeter, Δp is typically measured across a restriction such as an orifice plate to enable a compact design (the pressure transducers may be positioned in close proximity); however a length of conduit or tubing also generates a measureable Δp between the ends of the tubing. Once the calibration constant, k, is determined, eq. 1 is one equation in one unknown, or a "determined" set (of a single equation). In a well-designed and calibrated differential pressure flowmeter, measuring the differential pressure allows quantification of flow by algebraic operations. A problem in applying a differential pressure flowmeter to a suction thrombectomy system lies in the fact that the calibration constant, k, is dependent upon viscosity; and a thrombectomy procedure is anticipated to aspirate fluids of different viscosities. Another problem with differential pressure flowmeters in thrombectomy systems is the magnitude of the flow rate required for reliable results; the flow rate may need to be in the range of cc/second to hundreds of cc/second to elicit reliable and accurate results. The required minimum flow rate for a differential pressure flowmeter may be reduced by selecting a smaller orifice plate; this carries the risk of clogging with thrombus in a thrombectomy system. Therefore, even the ideal differential pressure flowmeter, as a component of a thrombectomy system, is subject to minimum-flow limitations and calibration errors as the aspirate viscosity changes. Flow sensing of the '683 patent is attained by means of a variant of a differential pressure flowmeter without an orifice plate. The embodiments of the '683 patent utilizes a constant-diameter "connecting tube" which does not exhibit features typical of a differential pressure flowmeter (e.g., orifice plate, venturi, etc.). The differential pressure data of the '683 patent actually measures the viscous losses incurred by the fluid within the connecting tube; this differential pressure measurement provides information regarding the viscosity and the flow rate of the liquid residing within the connecting tube, however the measurement is taken in the units of pressure and not flow.

Omitted in the '683 patent is consideration of viscosity; in relevant thrombectomy systems, flow and viscosity may be inextricably linked. An alternate governing equation is presented in eq. 2, known as the Hagen-Poiseulle equation, which relates differential pressure to both viscosity and flow; herein eq. 2 may be applied to pipes, conduits, tubing and catheters, etc.

$$\Delta p = \frac{8\mu LQ}{\pi R^4};\ Q = \frac{\pi R^4 \Delta p}{8\mu L};\ \mu = \frac{\pi R^4 \Delta p}{8QL};\ \mu Q = \frac{\pi R^4 \Delta p}{8L} \qquad \text{Eq. 2}$$

where μ is the dynamic viscosity, Δp is the differential pressure (between ends of the conduit), L and R are the length and radius of liquid path, or conduit. The Hagen-Poiseulle equation may be used to calculate or estimate the pressure drop in a pipe, or the pressure drop may be measured in order to determine viscosity or flow. Combining the geometric constants to a single (dimensioned) constant, K, a working equation for pressure drop in a pipe is expressed in eq. 3.

$$\Delta p = K\mu Q \quad \text{Eq. 3}$$

Eq. 3 is one equation in two unknowns (μ and Q); this is an underdetermined set of equations for which no unique solution generally exists. The Hagen-Poiseuille equation (eq. 2) relates intensive properties (μ and Δp) to the extensive property flow, Q, as expressed in eq. 3. Note that eq. 1 asserts that differential pressure, Δp, is linearly proportional to $Q^2$ for an inviscid fluid. In contrast, for a fluid of finite viscosity, eq. 3 asserts that Δp is linearly proportional the product of μ and Q. Eq. 3 asserts that, for a given differential pressure, viscosity (u) is inversely proportional to flow (Q).

In the application of eq. 2 and eq. 3, Δp (lower case) generally means the difference in pressure between opposite ends of a pipe, tube, conduit or catheter. In application of eq. 1, Δp generally means the difference in pressure upstream and downstream of a restriction, such as an orifice plate. Thrombectomy system embodiments of the present invention may aspirate a fluid (e.g., blood, saline, thrombus, etc.) through a catheter; therein Δp means the difference in pressure between the proximal and distal ends of the catheter, the distal end of the catheter being immersed in fluid (e.g, saline, blood, thrombus, etc.) at some (blood) pressure which may differ from atmospheric or ambient pressure. Subsequent equations herein employ a somewhat different ΔP (upper case) to mean the difference in pressure between the interior and exterior of a compliance chamber, the exterior of which being at substantially atmospheric pressure. Herein, Δp may generally be taken to mean the difference between pressures measured, inferred or observed at approximately opposite ends of a catheter (flow may exist within the catheter, so Δp exhibits a fluid pathway between the measurement locations). ΔP may generally be taken to mean the difference in pressure between the interior of a compliance chamber and atmospheric pressure (flow may not exist because of a solid, impenetrable boundary between the measurement locations). Both ΔP and Δp many also be normalized and/or non-dimensionalized to one. Blood pressure (if present, depending upon application) generally pushes fluid outward (proximally) through a catheter; atmospheric pressure (at the proximal end of an open catheter) generally opposes this flow. These two pressures, blood pressure (at the distal end of the catheter) and atmospheric pressure (at the proximal end of the catheter, including effects of atmospheric pressure acting upon a compliance chamber), are applied to opposite ends of the catheter and may be eliminated by coordinate transformation by algebraic means. To understand how and why a change in aspirate viscosity effects a change in differential pressure along a catheter, the length and diameter of the catheter are relevant as is the differential pressure along the catheter length (this is generally referenced as Δp herein). To measure the time rate-of-change of this differential pressure, pressure may be practicably measured in general proximity of a compliance chamber; the available and/or appropriate reference pressure therein is ambient or atmospheric pressure (this is generally referenced as ΔP herein). Embodiments of the present invention do not require that blood pressure (at or near the distal end of the catheter) is measured directly (i.e., there is no requirement for a pressure transducer at or near the distal end of the catheter); rather, blood pressure (if present, depending upon application) may be indirectly measured or inferred at or near zero flow through the catheter. In the absence (or near absence) of flow there is no (or almost no) viscous dissipation along the length of the catheter and the differential pressure, Δp, (between opposite ends of the catheter) may be taken to be approximately zero from eq. 1, eq. 2 and eq. 3. Normal, periodic fluctuations in blood pressure at the distal end of the catheter are acknowledged and overlooked herein. In time domain viscometry, viscosity, acting along the length of a catheter or conduit, may be measured; pressure may be measured at a single location at or near practical locations including: the proximal end of the catheter, inlet port of a pump, compliance chamber, etc.; such locations for a pressure measurement device may reference the measured pressure with respect to atmospheric or ambient pressure. Preferred embodiments of the present invention feature a single pressure measurement site, additional pressure measurement(s) taken at additional site(s) is anticipated.

Eq. 1, eq. 2 and eq. 3 relate the extensive property (Q) to intensive properties (Δp and/or μ). The constant of eq. 1 (k, having dimensions of $[L^7F^{-2}T^{-1}]$) introduces one new extensive property, time. The constant (K) of eq. 3 has dimensions of $[L^{-3}]$. The dimensions of Q (for volume flow rate and mass flow rate) are $[L^3T^{-1}]$ or $[M^3T^{-1}]$ (volumetric flow rate is generally used herein); however, time does explicitly appear as a variable in the preceding equations. Incorporation of the extensive property (time) is disclosed herein to construct and solve time-domain differential and or integral equations to elicit a unique solution (the quantitative determination of μ and Q) for eq. 3, which is underdetermined (i.e., possessing an unlimited number of valid solutions). Aspects and embodiments of the present invention disclose the use of time as a measured parameter (extensive property) and employ the hydraulic circuit/electric circuit analogy by modeling a thrombectomy system as a time-dependent RC (resistor-capacitor) electric circuit. The present invention discloses the use of a compliance chamber of variable volume (a non-isovolumetric component) to introduce another extensive property (volume, or $L^3$) to the set of equations. Differential, integral and/or algebraic equations may be employed to incorporate the relevant extensive parameter, time; this is because the time for a volumetric change of the compliance chamber may be measured. Eq. 1, eq. 2 and eq. 3 relate a (spatial) differential pressure (Δp) to flow, viscosity and geometric factors.

Some embodiments of the present invention may invoke analogous mathematical models, such as an RC (resistor-capacitor) circuit with a step function input (opening and closing a switch). FIG. 1*a* and FIG. 1*b* show analogous electric and hydraulic circuits. The analogous thrombectomy hydraulic circuit is comprised of a catheter, a differential pressure source (analogous to a battery), a valve (analogous to a switch) and a compliance chamber (analogous to a capacitor). The hydraulic analogue of variable resistance of the hydraulic circuit is the variable viscosity of the fluid in the catheter; the capacitance analogue is a compliance chamber which deforms under pressure or vacuum such that the chamber volume is a function of pressure (internal vs. external, or ΔP). Upon opening the valve (between a vacuum reservoir and the catheter), the compliance chamber deforms to a new (e.g., smaller) volume; the length of time required may be related to a time constant of an RC circuit or an analogous hydraulic circuit. Upon closing the valve, the compliance chamber may revert toward the original (e.g., larger) volume, again exhibiting a characteristic period of time for the volumetric change of the compliance chamber to occur. The volumetric displacement of the compliance chamber may be measured or quantified (if required); an underlying principle is that since it is possible to measure the length of time required for a characteristic volumetric change; the flow rate may thus be determined. Eq. 3 may be invoked to calculate the viscosity after having quantified the flow, or we may be unconcerned with quantification of the volumetric change of the compliance chamber and rather elect to quantify viscosity by other techniques afforded by time domain viscometry.

Time-domain differential viscometry may be applied to many applications in a broad array of fields, and it may also be applied to thrombectomy systems which do not employ a vacuum reservoir. Embodiments of time-domain differential viscometry may comprise a liquid syringe as a compliance chamber and a spring member to bias (force) the syringe plunger; this may provide a more linear pressure-volume relationship over a broad range of volumes. The (volume of the) compliance chamber may be forced to a volume by means of actuators, hydraulic cylinders, motors and gear train or crankshaft. The compliance chamber may be forced to a volume (to measure the change in pressure with respect to time), or a controlled force may be applied to the compliance chamber (to measure the change in volume with respect to time). The compliance chamber may be forced to an increased volume which generates a vapor space (cavitation, boiling) because aspirate flow through the catheter is insufficiently rapid to fill the void; the resulting non-equilibrium condition may provide the maximum attainable vacuum for maximum aspiration and clot/clog clearing.

Certain examples of suction thrombectomy systems are representative of a large class of apparatus which are comprised of a gas/vapor pump utilized to evacuate a reservoir for the admission of liquids, solids, vapors and gasses into the reservoir, a Shop-Vac is another example. In contrast, liquid pump thrombectomy systems are representatives of a class of apparatus which are comprised of a pump and pipes or a piping network; (non-thrombectomy) examples abound in industrial, commercial, scientific and environmental applications. Time-domain viscometry is disclosed in embodiments which are described as thrombectomy systems of both types (both vacuum reservoir and liquid pump); the inclusion of time-domain viscometry into other, unrelated applications is anticipated. Incorporating a viscometer into thrombectomy systems is the selected application to disclose this technology because of the importance of viscometry and/or flow measurement to thrombectomy procedures; the improvements to thrombectomy systems by the enabling disclosures herein conserve valuable resources: human blood and time.

The relevant equations for time domain viscometry are derived herein with reference to generalized non-isovolumetric elements (embodiments) including: a length of tubing, a flexible bladder, or "squeeze bulb," piston-in-cylinder and syringe embodiments to name a few. The volume scale of such embodiments may range between approximately 1 cc to 100 cc and the time scale for those embodiments may range between approximately 1 second to 5 minutes to sufficiently fill and empty. Subsequently, a peristaltic pump is considered wherein the volume scale may be approximately 10 μl to 5 cc and the time scale may be approximately 10 μs to 5 seconds.

Time domain viscometry is further disclosed through example analyses of pulsatile, transient pressure data collected upon a peristaltic pump fluid system. Viscosity and flow rate are stated herein to be inversely proportional; therefore viscosity may be measured or approximated by measuring and analyzing the rate of change of pressure or "pressure decay" (under appropriate conditions). Representative equations for time-domain viscometry are disclosed in closed-form expressions wherein experimental data and calibration constants are combined to provide quantitative experimental measurements of viscosity (in terms of variable data). This is in contrast to prior art wherein experimental data are correlated to arbitrary constants, reference data or library data to provide descriptions or characteristics of the viscosity (in terms of attribute data).

Embodiments of the present invention include any generalized conduit comprising a non-isovolumetric element which may expand or contract in response to a differential pressure (with reference to external, ambient, or atmospheric pressure) or external force. In a steady-state, such a non-isovolumetric element may assume a characteristic volume which does not appreciably change with time; example non-isovolumetric elements include a pneumatic tire, a balloon or a basketball. In an unsteady-state, such as a leak in any of the above examples, the pressure will decrease in proportion to: (1) the size of the leak, (2) the instantaneous internal (differential) pressure and (3) the kinetic or dynamic viscosity of the fluid passing through the leaking orifice (inverse proportion). The examples exhibit finite volumes, and eventually a sufficient quantity of fluid will escape such that the internal and external pressures become essentially equalized, and flow is no longer observed. Time-domain viscometry may be accomplished by analyzing the rate of pressure decay. Herein, the term "pressure decay" includes increases and decreases in differential pressure, the term "pressure" includes pressures below ambient or atmospheric which may be termed "vacuum." In this context, pressure decay occurs when distorted components are or become unconstrained in order to elastically return toward a nominal dimension by means of fluid transfer as the internal pressure returns toward ambient.

A fundamental aspect of time domain viscometry is that the time rate of change of pressure, or the slope, may be measured in order to measure the viscosity of fluids. A fundamental equation of a time domain viscometer is presented in eq. 4:

$$dP/dt = f(\mu, P, \ldots) \qquad \text{eq. 4}$$

where f is some, yet undetermined, function. The slope of a pressure vs time graph (pressure decay) is a function of the viscosity of the fluid and the slope of the graph may be obtained from experimental data by numerical methods including finite difference, differential quadrature, etc. Time domain viscometry comprises differential and/or integral analysis of a measured data, which may include pressure, flow, motor current, etc. Numerical approximations of derivatives, slopes and/or curvature of measured data may be calculated an thus infer intensive properties (such as viscosity) and extensive properties (such as flow). In contrast to eq. 1, eq. 2 and eq. 3 (which describe a spatial differential pressure, Δp under conditions which may be assumed to be steady), eq. 4 describes the (unsteady) temporal rate-of-change of pressure measured at a single location.

Approximations or estimations (and herein, measurement) of slopes, derivatives, curvature, etc. of experimental data may be calculated from analysis methods (of pressure vs time data) such as linear regression, finite difference, curvilinear regression, etc. Implementation of eq. 4 in the present invention is presented in embodiments which employ finite difference approximations or measurements of the slope of a line (a derivative). An unscaled finite difference approximation or measurement may be implemented by calculating the difference between two or more (pressure) measurements with respect to time; this difference may optionally be scaled by a function of the time interval. Time domain viscometry comprises the ratiometric comparison of two or more measurements; these measurements may be pressure, a function of pressure, the slope of the pressure trace, a derivative of the pressure trace, an integral of the pressure trace, etc. The ratio of these measurements may be a function of the ratio of the viscosities of two fluids.

Differential pressure may be defined as a difference in pressure between two points in space. In some instances hereinafter, differential pressure may mean the difference in pressure between the inside and outside regions of any non-isovolumetric component which exhibits a fluid-impenetrable barrier between the interior and exterior surfaces; fluid transfer into and out of the non-isovolumetric component may occur by means including apertures, openings, tubing, etc. This meaning of differential pressure may be denoted as ΔP indicating that the pressure measurement is taken across a solid boundary. A pressure transducer typically measures a differential pressure with a reference to atmospheric pressure; peristaltic pump tubing is typically exposed to the same atmospheric pressure. The pressure transducer may thereby measure the differential pressure between the interior of the peristaltic pump tubing (at a point or location) and atmospheric or ambient pressure. This is in contrast to alternate definitions (e.g., the '683 patent) of differential pressure (therein denoted ΔP) wherein two pressure transducers measure pressure upstream and downstream of a characteristic feature (e.g., connection tube, length of tubing, orifice, pump, restriction, etc.). It is acknowledged that a peristaltic pump provides an axial differential pressure between the inlet port and the reservoir from which the fluid is drawn. It will be disclosed herein that a single pressure transducer provides the necessary and sufficient data to determine the differential pressure between (1) the interior and exterior of any non-isovolumetric component and atmosphere (herein generally denoted by ΔP) and (2) between the pump inlet and the reservoir from which the fluid is drawn (herein generally denoted as Δp).

Pulsatile flow in a non-isovolumetric system may provide an ongoing sequence of expansion and contraction cycles which may be analyzed for the rates of increasing and decreasing pressure. In general, a less-viscous fluid exhibits faster differential pressure decay while a more-viscous fluid exhibits a slower differential pressure decay. Peristaltic pumps represent an ideal apparatus for time-domain viscometry because the pump tubing characteristically acts as a non-isovolumetric element which is expanded or compressed due to roller forces and/or differential pressure between the inside and outside of the tubing. As any force or differential pressure (constraint) is relieved, the tubing relaxes or reverts toward nominal dimensions as flow into or out of the tubing is permitted. An embodiment of the present invention comprises stopping the rotor of a peristaltic pump and measuring the rate of differential pressure decay as the pump tubing relaxes toward nominal dimension; any portion of the pressure and/or slope of the pressure trace data may be used to determine the viscosity of the fluid being transferred.

The rate of pressure decay may also be a function of the magnitude of the differential pressure; this phenomenon is acknowledged and exploited in embodiments of the present invention by analyzing data at variable or multiple pump speeds. At low pump speeds and low flow rates, the differential pressure may also be low. As the pump speed is increased, the rate-of-shear is also increased; thus the rheological properties of the fluid may also be determined. The speed, frequency or setpoint, of the pump thereby provides additional data and information for analysis; this may be termed "frequency-domain viscometry," as disclosed in co-pending applications listed as references. Embodiments of the present invention may incorporate both time-domain and frequency-domain viscometry to provide viscometric data which may be accurately and precisely converted to engineering units including cP, cSt, Pa's, etc.

Peristaltic pumps are generally comprised of flexible tubing which may be radially compressed to create discontinuities in fluid communication within the tubing, much akin to valves in general and specifically to pinch valves. A peristaltic pump may be described as a rotary array of pinch valves which sequentially isolate and move a fluid-filled cavity; the no-penetration boundary of the cavity being comprised of radially compressible tubing. The discrete cavity may be (1) overfilled and distended (greater radius), (2) nominally filled (nominal radius), or (3) underfilled and contracted (smaller radius). Because of elastic pressure vessel theory: (1) internal pressure exceeding ambient results in a distended cavity of greater volume, (2) internal pressure approximately equal to ambient results in a nominally filled cavity, or (3) internal pressure less than ambient results in a contracted cavity of lesser volume. Each of these conditions may arise from any combination of factors including inlet and outlet pressures, flow restrictions, occlusions, fluid viscosity, etc. These factors may exert their influence in either the inlet (upstream) or outlet (downstream) conduits. Since peristaltic pumps are generally reversible, the present invention comprises embodiments wherein the non-isovolumetric component may be in fluid communication with either the inlet port or the outlet port of the pump. In a peristaltic pump, each discrete cavity is created as a pump roller passes/opens the inlet port and moves a no-penetration fluid barrier axially along the tubing; subsequently a second pump roller passes/closes the inlet port and isolates a fluid-filled cavity. The pressure within the fluid cavity at the time that the second roller isolates the cavity may be deterministic of both the fluid volume of, and the pressure within, the cavity for the duration of the cavity's existence.

Embodiments of the present invention may feature a combination of a peristaltic pump, a step-motor/controller and one or more pressure transducers. In some embodiments, after flow is established (by rotating the pump shaft), the rotor is stopped and the inlet and/or outlet pressure(s) are then monitored for initial pressure ($P_0$) and time rate of pressure decay. In general operation of a pump, a lower operating pressure at the inlet and/or a higher operating pressure at the outlet are characteristic of a more viscous fluid; this data may be used to quantitatively determine viscosity with some accuracy. However, it is the rate of pressure decay (as fluid flow permits the tubing to relax toward nominal dimension) that is herein utilized for greatly improved accuracy. In other embodiments, the rotor may be rotating while the time rate of pressure decay is calculated. Embodiments disclosed herein are presented with instrumentation outfitted and analysis performed on the pump inlet, where pressures are generally below atmospheric. The present invention may be reduced to practice equally well to applications wherein the pump outlet is instrumented and pressures above ambient are analyzed.

In some applications it is important to minimize the amount of fluid sampled for viscometric determination; the peristaltic pump viscometer is capable of measuring viscosity with a very small sample volume. For example, a commercially available peristaltic pump with 3 rollers, 5 mm ID tubing and approximately 15 mm radius transfers approximately 0.4 cc per ⅓ revolution; ⅓ revolution is sufficient for viscosity measurement by employing the means of the present invention. Smaller pumps and/or with more rollers may permit viscometry to be performed with even smaller sample volumes, the lower limit may approach 10 µl per sample. Medical devices aspirating or drawing blood represent an example application where it is important to minimize the volume of blood which is aspirated or lost to viscometric sampling and analysis.

The present invention differs from prior-art viscometers in 3 noteworthy aspects: (1) continuous flow process, (2) deformable components provide the source of differential pressure and (3) pressure is measured and analyzed as a function of time. In drip cup and capillary viscometers of prior art, time is measured and correlated to viscosity through reference/library data; thus the independent variable (time) is correlated to the dependent variable (viscosity) through library or reference data. In the present invention, time is the independent variable and pressure is the dependent variable; calculations performed upon the dependent variable (e.g., magnitude and slope of pressure, area under the pressure curve, etc.) may provide quantitative viscometric data through closed-form expressions.

Relevant examples from prior art make use of attribute data in qualitative terms including: monitor/monitoring, measuring a characteristic, determine flow rate, etc.; these activities typically generate attribute data, e.g., "unrestricted flow, restricted flow, or clogged" changed or not changed, high viscosity, low viscosity, etc. Examples from prior art share a common theme of attempting to measure a flow rate (an extensive property) by using measurements from one or more pressure transducers (which measure an intensive property, pressure). Therefore, prior art is generally limited the use of attribute data because attempts to transform (intensive variable) pressure (in engineering units e.g., Pa, psi, mmHg, etc.) into (extensive variable) flow (in engineering units e.g., m3/s, cc/see, liters/minute, etc.) have been unsuccessful. To overcome this problem, the present invention introduces an extensive property, time, to facilitate the transformation from pressure to flow and/or viscosity.

The present invention is readily distinguishable from prior art by using variable data in quantitative terms including: measuring, quantifying, quantitatively determining, estimating, approximating, etc. The present invention is disclosed in a context and scope comprising the utilization of variable data in depicted embodiments, descriptions, calculations, etc. The present invention comprises a transformation of variable data (measured or collected in a first set of dimensions and units) into a new set of variable data (measured or quantified in a second set of dimensions and units). The present invention is well suited to quantify flow rate, viscosity, delivery volume as required by the application. Because viscosity is an intensive property, any changes in flow rate do not generally affect viscosity (for a Newtonian fluid); Newtonian viscosity may be considered "invariant" to flow rate. Because flow is an extensive property, any changes in viscosity generally do affect flow rate. For this reason, the present invention is disclosed in the context of measuring viscosity (an intensive, generally flow-invariant property) preferentially over measuring flow rate and delivery volume (extensive properties generally dependent upon viscosity).

BRIEF DESCRIPTION OF THE DRAWINGS

FIG. 1*b* (along with FIG. 2*b*, FIG. 3*b* and FIG. 5*b*) are annotated Prior Art because the circuit design and corresponding analysis appear in many textbooks.

FIG. 9*a* through FIG. 9*e* depict prior art as a "squeeze bulb" example.

FIG. 9*b* shows a perspective view of the compliance chamber of FIG. 9*a*.

FIG. 9*c* shows a cutaway view of a compliance chamber embodiment at intermediate volume.

FIG. 9*d* shows a perspective view of the compliance chamber of FIG. 9*c*.

FIG. 9*e* shows a cutaway view of a compliance chamber embodiment at or near minimum volume.

FIG. 16*c* shows finite difference analysis of a portion of the data of FIG. 16*a*. First and second order approximations of viscosity are calculated for each of the 7 representative fluids.

FIG. 16*d* shows an abridged version of the experimental pressure trace data graphed in FIG. 16*a* and FIG. 16*b*.

DETAILED DESCRIPTION OF THE DRAWINGS

Figure 1A:
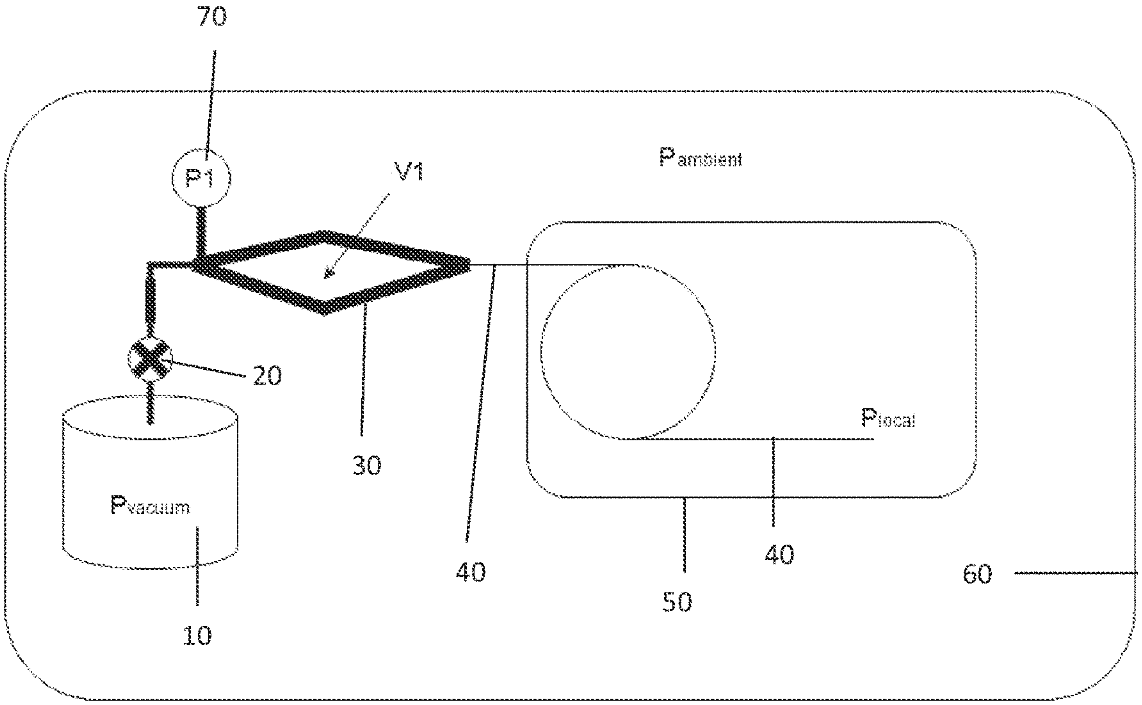
FIG. 1*a* shows a suction thrombectomy system with the valve closed, the volume of the compliance chamber is greatest of the following sequences. The compliance chamber is at static equilibrium between the internal pressure ($P_{local}$) and the external pressure ($P_{ambient}$).

FIG. 1*a* shows a suction thrombectomy system comprised of vacuum reservoir 10 operating at $P_{vacuum}$, vacuum valve 20 (shown in the closed position), pressure sensor 70 (measuring pressure P1), compliance chamber 30 (at volume V1), and catheter 40. Catheter 40 penetrates patient body 50 and is immersed in intravascular fluid (at $P_{local}$) at the distal end; ambient atmosphere 60 surrounds all components of FIG. 1*a*. FIG. 1*a* is stated to be at or near static equilibrium (at or near zero flow); the pressure measured by pressure sensor 70 may be approximately equal to $P_{local}$. P1 and V1 are interdependent in that any change in pressure (at pressure sensor 70) will result in corresponding change in volume (V1) of compliance chamber 30; e.g., a decrease in internal pressure may result in a corresponding decrease in the volume of compliance chamber 30. This relationship may be linear, logarithmic/exponential, polynomial or otherwise expressed as a mathematical function; however, explicit determination of this relationship may not need to be instituted by the methodologies disclosed as aspects of the present invention. FIGS. 1 through 4 assume a homogeneous aspirate of unchanging viscosity, the viscosity being small enough that finite fluid flow occurs for any finite value of Δp; variations in viscosity with respect to time are considered subsequently.

FIG. 1 illustrates an important distinction, the difference (if any exists) between $P_{local}$ and P1 (measured by pressure sensor 70) and the difference between $P_{ambient}$ and P1. The difference between $P_{local}$ and P1 is generally denoted Δp herein, and may be recognized as "blood pressure" at the distal end of catheter 40. Operationally, P1 may generally be assumed to be equal to or less than $P_{local}$, and this represents the differential pressure which applies an axial force acting upon fluid (e.g., saline, blood, thrombus, paint, oil, etc.) contained within catheter 40. Operationally, the measured value of P1 may generally be assumed to be equal to or less than $P_{local}$; and this instantaneous difference (between internal and external pressure of compliance chamber 30) is generally denoted ΔP herein and may be (1) quantitatively deterministic of the instantaneous volume of compliance chamber 30 and (2) quantitatively deterministic of the instantaneous flow rate into compliance chamber 30 including flow through catheter 40. Embodiments of the present invention (e.g., the apparatus of FIG. 1*a*) may readily measure ΔP for use in subsequent calculations. In FIG. 1*a* (stated to be at static equilibrium) pressure sensor 70 may measure $P_{local}$ with respect to $P_{ambient}$; this measurement may be assigned the value of zero by coordinate transformation. Thus, blood pressure (if present depending upon application) may be algebraically eliminated through coordinate transformation.

Figure 1B:
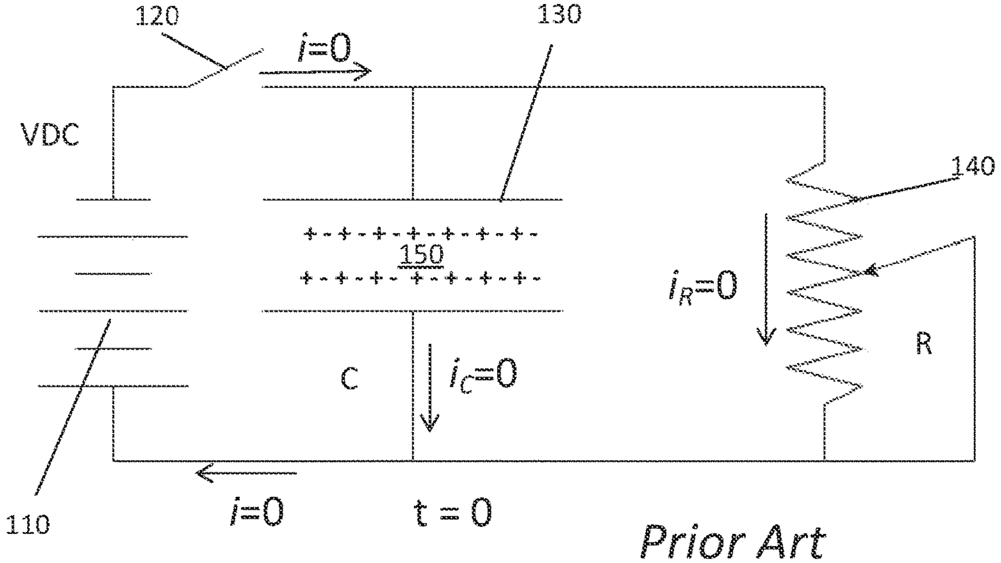
FIG. 1*b* shows the analogous electric circuit with the switch open; the charge on the capacitor plates is neutral. The resistor is variable.

FIG. 1*b* shows an R-C electric circuit analogous to the thrombectomy system of FIG. 1*a*; the circuit is comprised of voltage source 110, switch 120, capacitor 130, and variable resistor 140. Switch 120 is shown in the open position; current flow through each component and the loop is zero. Capacitor 130 is shown in FIG. 1*b* to have neutral/equal charge on the plates; the capacitor is discharged or having a neutral charge 150 at time t=0. FIG. 1*b* is stated to be at static equilibrium; current is not flowing and there is zero charge on capacitor 130. FIG. 1*b* is annotated Prior Art because the circuit design and analysis appear in many textbooks.

Figure 2A:
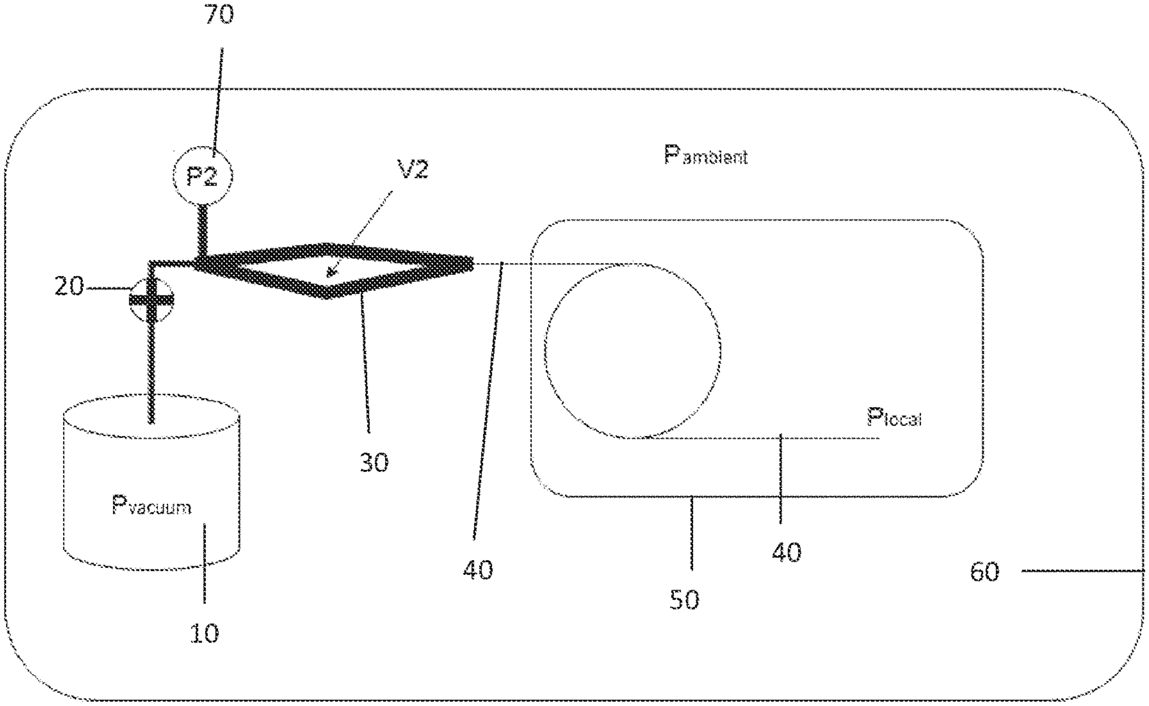
FIG. 2*a* shows the suction thrombectomy system a short time after the valve is opened; the volume of the compliance chamber is diminished from FIG. 1*a*. The compliance chamber volume is decreasing with time.

FIG. 2*a* shows the suction thrombectomy system at a time shortly after vacuum valve 20 is changed to the open position (at time t=0); pressure sensor 70 measures pressure P2, which is less than pressure P1 of FIG. 1*a*. Compliance chamber 30 is decreasing in volume to volume V2, which is less than volume V1 of FIG. 1*a*. Pressure P2 and compliance chamber 30 volume, V2, may be continuously changing in time as compliance chamber 30 continues to deform and assume continuously decreasing volume; a characteristic "emptying time" may be established when the pressure measured at pressure sensor 70 ceases to change with time. After the requisite "emptying time" the system assumes a steady state wherein neither the volume of compliance chamber 30 nor the pressure measured by pressure sensor 70 continue to change with time.

Figure 2B:
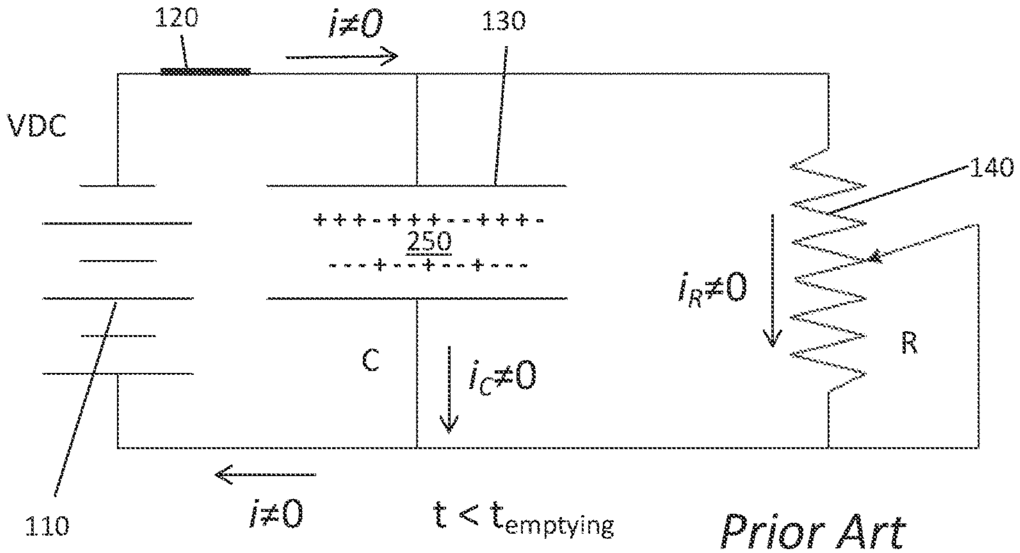
FIG. 2*b* shows the analogous electric circuit with the switch closed, a charge is building on the capacitor plates.

FIG. 2*b* shows the analogous electric circuit shortly after switch 120 is closed; capacitor 130 is at a state of partial charge 250 and exhibits non-zero current, $i_c \neq 0$. Independently (parallel circuitry), non-zero current, $i_R \neq 0$, is shown to exist through variable resistor 140. Total current, i, is the sum or the non-zero currents $i_R$ and $i_c$; total current, i, is unknown because it is one equation in two unknowns. During the interim period of time $t<t_{emptying}$, capacitor 130 is charging, analogously to compliance chamber 30 exhibiting a decreasing volume wherein the contents of the compliance chamber are "emptying" by transferring fluid from the compliance chamber 30 to vacuum reservoir 10. FIG. 2*b* is annotated Prior Art because the circuit design and analysis appear in many textbooks.

Figure 3A:
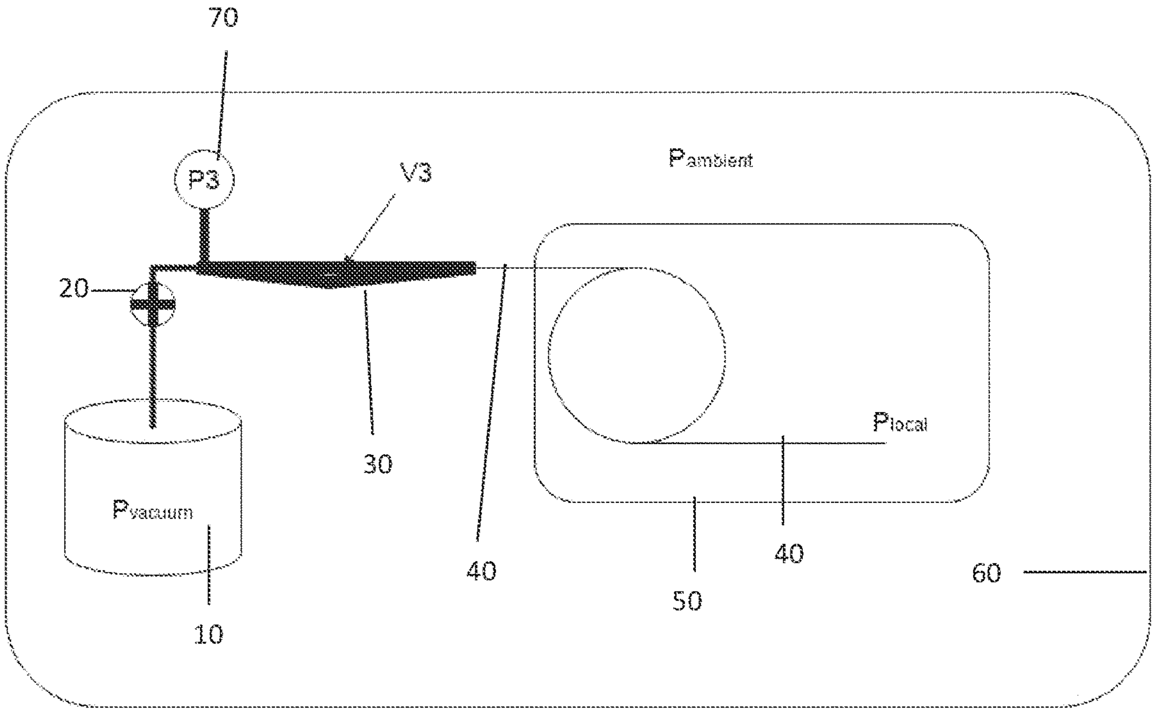
FIG. 3*a* shows the suction thrombectomy system after the valve is opened for a sufficient duration; the volume of the compliance chamber is diminished to the smallest of the sequences.

FIG. 3*a* shows the suction thrombectomy system at a time sufficiently greater than $t_{emptying}$ such that compliance chamber 30 is at constant volume, V3 (V3<V2<V1), with respect to time; FIG. 3*a* is stated to be at or near static equilibrium. Pressure P3 (P3<P2<P1), measured by pressure sensor 70 is no longer time dependent. Vacuum valve 20 is open and an equilibrium compliance chamber 30 volume exists with measured pressure P3. At time t*, vacuum valve 20 is changed to the closed position, as shown in FIG. 4*a*.

Figure 3B:
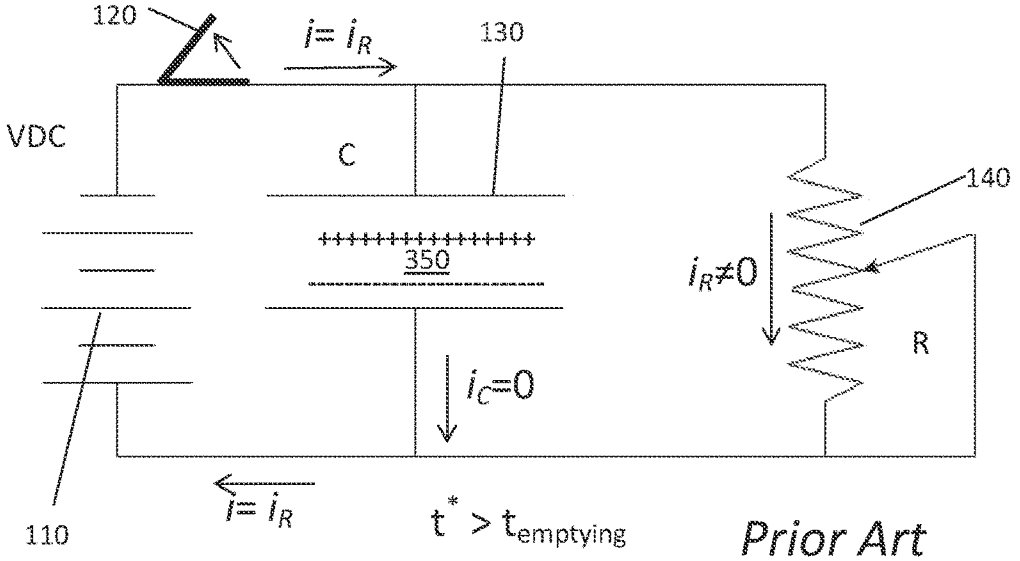
FIG. 3*b* shows the analogous electric circuit with the switch closed, the capacitor plates are completely charged.

FIG. 3*b* shows the analogous electric circuit at steady state, with $i_c=0$ through capacitor 130; a fully charged 350 state of capacitor 130 is shown. Current through variable resistor 140 is non-zero ($i_R\neq0$); an electrical steady state exists corresponding to static equilibrium of the hydraulic analogy to FIG. 3*a*. At time t*, switch 120 is changed to the open position, as shown in FIG. 4*b*. FIG. 3*b* is annotated Prior Art because the circuit design and analysis appear in many textbooks.

Figure 4A:
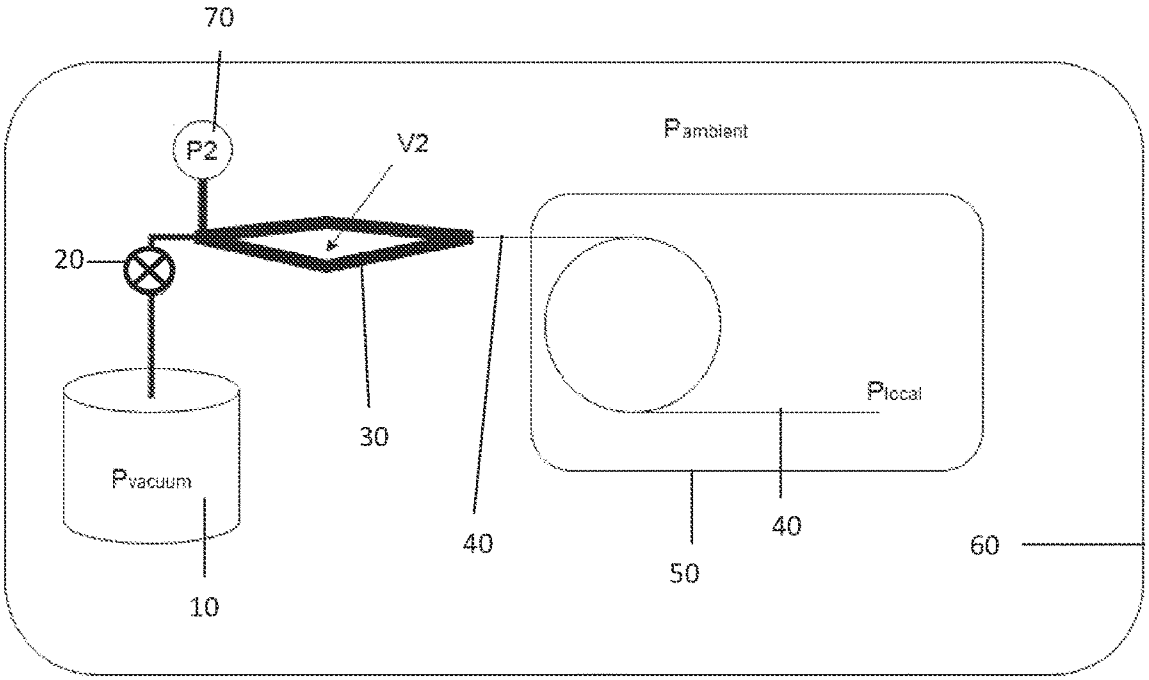
FIG. 4*a* shows the suction thrombectomy system a short time after the valve is closed; the volume of the compliance chamber is increasing. Flow exists between the patient vascular system and the compliance chamber.
Figure 4B:
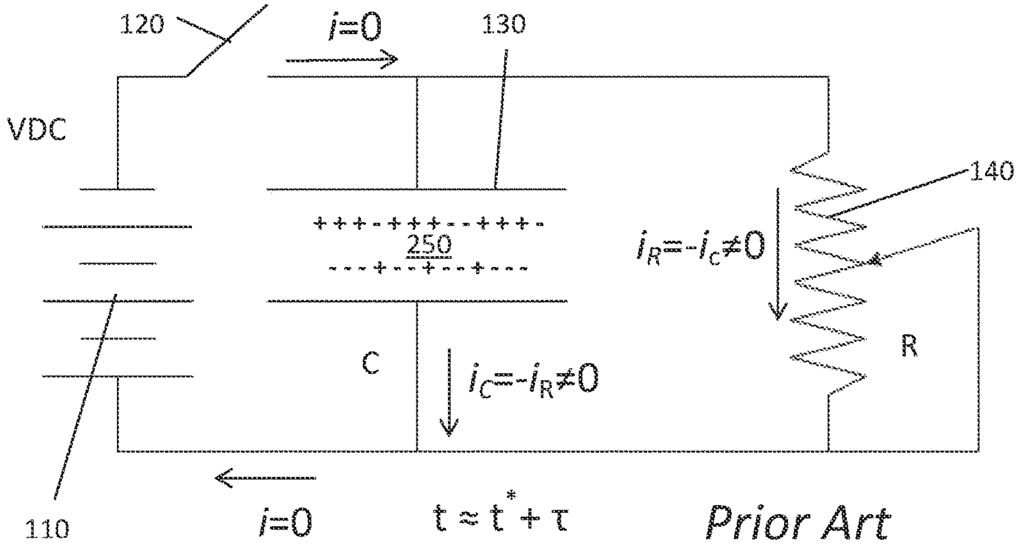
FIG. 4*b* shows the analogous electric circuit a short time after the switch was opened; the capacitor is discharging. Current exists in the capacitor-resistor loop.

FIG. 4*a* shows the suction thrombectomy system shortly after vacuum valve 20 is changed to the closed position. An intermediate value of pressure, P2, is measured by pressure sensor 70; this is accompanied by, and may be correlated to an intermediate volume, V2, existing in compliance chamber 30. Compliance chamber 30 is increasing in volume (with respect to time); the requisite fluid flow is through catheter 40, given that vacuum valve 20 is closed. At this point in time, the differential pressure between $P_{local}$ and P2 (measured at pressure sensor 70) drives aspirate flow through catheter 40 and into compliance chamber 30. The rate at which compliance chamber 30 changes volume ("fills") may be directly proportional to aspirate flow rate through catheter 40.

FIG. 4*b* shows the analogous electric circuit shortly after switch 120 is opened; net current through the voltage source is zero (i=0) and non-zero current is conserved through the RC circuit ($i_c=-i_R\neq0$). Capacitor 130 is discharging to supply current flow through variable resistor 140; at time $t=t^*+\tau$, capacitor 130 is shown with partial charge 250. FIG. 4*b* is annotated Prior Art because the circuit design and analysis appear in many textbooks.

FIG. 1 through FIG. 4 show an idealized cycle comprising a temporal sequence of closing, then opening, then closing vacuum valve 20 while collecting data from pressure sensor 70. As in any engineering discipline, the solution to the governing equations may be presented; systematic and experimental errors may introduce error and uncertainty in any experimental results. Herein, initial and boundary conditions may be stated in absolute terms including maximum, minimum, zero, static equilibrium, etc.; in all cases, deviations from these absolute terms are anticipated.

An operational cycle of an embodiment of time domain viscometry is described. In FIG. 1*a*, vacuum valve 20 is closed and compliance chamber 30 has assumed volume V1 and is in static equilibrium with pressure $P_{local}$; fluid flow is zero. In the analogous electric circuit of FIG. 1*b*, switch 120 is open and there is a neutral charge 150 on capacitor 130; current flow through the circuit is zero (i=0) at time t=0.

In FIG. 2*a*, vacuum valve 20 is opened at time t=0, FIG. 2*b* shows an intermediate time such that $0<t<t_{emptying}$; compliance chamber 30 is emptying by changing volume. Pressure P2 is generally less than $P_{local}$, therefore flow exists in catheter 40; aspiration has begun and the flow rate is a function of the differential pressure (Δp) and the viscosity of the fluid in catheter 40. In the analogous electric circuit of FIG. 2*b*, switch 120 is closed at t=0; capacitor 130 is charging and is shown at a partial charge 250 state. Current flow through variable resistor 140 is non-zero ($i_R\neq0$) and is a function of the voltage across capacitor 130; current through variable resistor 140 is a function of voltage and the electrical resistance of variable resistor 140.

In FIG. 3*a*, vacuum valve 20 has been open long enough ($t>t_{emptying}$) for compliance chamber 30 to assume volume V3, (V3<V2<V1), and may be in static equilibrium exhibiting pressure P3, (P3<P2<P1), measured by pressure sensor 70. Flow through catheter 40 is a function of differential pressure ($P_{local}-P3$) and the fluid viscosity. At time t*, vacuum valve 20 is closed. In the analogous electric circuit of FIG. 3*b*, switch 120 has been closed long enough for capacitor 130 to reach a fully charged 350 state. Current flow through variable resistor 140 is non-zero ($i_R\neq0$) and is a function of the concurrent voltage across capacitor 130; current through variable resistor 140 is a function of voltage and the electrical resistance of variable resistor 140. At time t* switch 120 is opened.

In FIG. 4*a*, vacuum valve 20 is closed at timet*; fluid flow between compliance chamber 30 and vacuum reservoir 10 may become zero (because valve 20 is closed). As the pressure measured by pressure sensor 70 attains a value approximately equal to P2, compliance chamber 30 concurrently attains a volume approximately equal to V2. At the instant of FIG. 4*a*, compliance chamber 30 is filling with fluid flowing through catheter 40; flow through catheter 40 is a function of differential pressure (Δp or $P_{local}$-P2) and the fluid viscosity within catheter 40. In the analogous electric circuit of FIG. 4*b*, switch 120 has been open for a period of time (t) sufficient for capacitor 130 to have discharged to a partial charge 250 state. As capacitor 130 discharges, current flows from capacitor 130 through variable resistor 140; current through variable resistor is a function of the voltage across capacitor 130 and the electrical resistance of variable resistor 140. From conservation of charge for a capacitor, $i_R=-i_c\neq0$; net current flow through voltage source 110 is zero, i=0.

FIG. 1*a* through FIG. 4*b* show the compliance chamber 30 and analogous capacitor 130 transitioning (in time) from neutral charge (FIG. 1*a* and FIG. 1*b*), to partial charge (FIG. 2*a* and FIG. 2*b*), to the fully charged state (FIG. 3*a* and FIG. 3*b*). FIG. 4*a* and FIG. 4*b* show compliance chamber 30 filling and capacitor 130 discharging. The states depicted in FIGS. 1*a*, 1*b*, 3*a*, and 3*b* may represent steady flow or equilibrium conditions; the states depicted in FIGS. 2*a*, 2*b*, 4*a* and 4*b* may represent unsteady flow, non-equilibrium, time-dependent states. In this context, the term charging may mean: a decrease in volume of compliance chamber 30 or the analogous increase in stored charge in capacitor 130. Conversely, in this context, the term discharging may mean: an increase in volume of compliance chamber 30 or the analogous decrease in stored charge in capacitor 130. The rates of charging and discharging are time-dependent events. Embodiments of present invention are disclosed to include steady state, steady flow or equilibrium conditions as part of a cycle; this apparent constraint is avoided herein by employing mathematical techniques comprising the present invention. Time domain viscometry is disclosed herein as comprising a cycle of charging and discharging a compliance chamber analogously to a capacitor. The mathematical models employed in standard circuit analyses as well as the present invention may typically be posed as starting and ending at equilibrium conditions. In practice, time domain viscometry may be conducted from arbitrary and non-extreme, non-equilibrium endpoints. Time domain viscometry may be conducted between arbitrary volumes, pressure and/or time endpoints; preferred embodiments incorporate an efficient and robust algorithm and may permit time domain viscometry to be accomplished in less than one second (approximate range 0.1 s to 10 s). Some equilibrium conditions are shown and described for clarification and simplicity; in practice equilibrium need not be attained for the analytical techniques of the present invention to be effective. The measurement of $P_{local}$ may be conducted at equilibrium (approximately zero differential pressure and flow); the difference between any measured pressure and $P_{local}$ may be the differential pressure between the pressure sensor and the distal end of the conduit or catheter (Δp).

Aspects of the present invention disclose and illustrate the use of standard circuit analysis techniques to determine the viscosity of fluid contained within catheter 40 by solving the analogous electric circuit equations for current flow through variable resistor 140. The relevant electric circuit equations are presented in eq. 5 and eq. 6. Eq. 7 is enforced whenever switch 120 is open.

$$i_R = \frac{v}{R};\ i_C = C\frac{dv}{dt} \quad \text{Eq. 5}$$

$$i = i_C + i_R \quad \text{Eq. 6}$$

$$i_C = -i_R(\text{when } i = 0;\ \text{switch open}) \quad \text{Eq. 7}$$

Combining Eq. 5 and Eq. 6 Yields Eq. 8:

$$i = C\frac{dv}{dt} + \frac{v}{R} \quad \text{Eq. 8}$$

Assuming a charged capacitor state and imposing eq. 7 (switch open, valve closed) yields eq. 9:

$$0 = C\frac{dv}{dt} + \frac{v}{R};\ C\frac{dv}{dt} = \frac{-v}{R};\ \frac{dv}{dt} = \frac{-v}{RC};\ \frac{v\prime}{v} = \frac{-1}{RC};\ \frac{v\prime}{v} = \frac{-1}{\tau} \quad \text{Eq. 9}$$

Where v' is the time derivative of voltage, the time constant, τ, may mean (in this electric analogy context) to be the product of R and C. Differential eq. 9 may be solved by standard techniques; a solution is presented in eq. 10:

$$v(t) = v_0 e^{-t/\tau};\ \frac{v\prime}{v} = \frac{-1}{\tau};\ v' \approx v\frac{-1}{\tau} \quad \text{Eq. 10}$$

where the initial voltage, $v_0$, may be determined from the initial conditions. Eq. 10 may provide a governing differential equation for the hydraulic analogy wherein pressure (P) is analogous to voltage (v), compliance chamber 30 volume is analogous to capacitor 130 charge, and fluid flow through catheter 40 is analogous to current flow through variable resistor 140. Eq. 10 may be re-written in terms of the hydraulic analogue in eq. 11.

$$P(t) \approx P_0 e^{-t/\tau};\ \frac{P\prime}{P} \approx \frac{-1}{\tau};\ P' \approx P\frac{-1}{\tau} \quad \text{Eq. 11}$$

Where time constant (t), in this context, may mean the product of viscosity and compliance, by analogy with the electric circuit. P(t), in this context, may be the measured value, ΔP; the differential pressure between the interior and exterior wall of compliance chamber 30; this is the pressure measured at pressure sensor 70.

Eq. 11 asserts that pressure (P, or ΔP, measured at pressure sensor 70) will experience an exponential decay; aspects of the present invention utilize the correlation the between the exponential decay of pressure to the corresponding exponential decay of both compliance chamber 30 volume and flow rate through catheter 40. The flow rate through catheter 40 is a function of viscosity, analogously to the current flow ($I_R$) through variable resistor 140 being a function of the resistance setting. Eq. 11 instructs that, after some number of time constants, t, (approximately 5) have elapsed, P(t)≈0; when P(t)≈0; this means that the pressure (measured at pressure sensor 70) may be approximately equal to $P_{local}$ (located within patient body 50). Thus, P(t) is a time dependent (spatial) differential pressure between the pressure measured at pressure sensor 70 and $P_{local}$ (because the system is moving toward pressure equilibrium with $P_{local}$). $P_{local}$ may be stored (from a previous iteration) and may be measured at any time sufficiently after closing vacuum valve 20, as shown in FIG. 1*a*. At any time that a differential pressure exists between pressure sensor 70 and $P_{local}$ within patient body 50, flow through catheter 40 may exist (excluding instances of a clog, analogous to infinite resistance or an open circuit in the electric circuit). The two right hand forms of eq. 11 may have units of inverse time, (1/t), or units of pressure per time (P/t) depending upon the normalization and non-dimensional technique employed. Eq. 11 is equivalent to eq. 10 wherein voltage, v, is replaced with pressure, P; many examples of commercially available pressure sensor 70 feature a voltage output which is proportional to pressure. Eq. 11 may thereby be solved in voltage-range coordinates or units; there may be no need to convert the measured voltage to pressure units by use of a conversion or calibration constant or factor. Calibration and/or unit conversion of pressure transducer output units (e.g., V, mA, etc.) into pressure units (e.g., Pa, psi, mmHg, etc.) is generally not required in preferred embodiments of the present invention.

The viscosity of the fluid in catheter 40 may influence the flow rate; a more viscous fluid may require a greater period of time for any given volumetric change in compliance chamber 30. A less viscous fluid in catheter 40 may approach equilibrium in less time than a more viscous fluid. A less viscous fluid may therefore exhibit a shorter time constant, τ, than a more viscous fluid. By measuring, approximating or estimating the time constant, τ, (e.g., by closing vacuum valve 20, etc.), the present invention may quantitatively measure viscosity; other system parameters (e.g., flow and delivery volume) may be calculated in a similar manner, if required. For instance, catheter 40 may be immersed in a measured volume of fluid ($V_{initial}$) at time t* (the instant that vacuum valve 20 is closed). After time trill has elapsed (zero flow), the difference between the initial and final volumes is approximately equal to the compliance chamber volume ($V_{initial}-V_{final}\approx\Delta V_{compliance\ chamber}$); measurement of the compliance chamber volumetric displacement may provide direct calculation of flow at any pressure. Measurement of viscosity (delivery volume or flow) may occur with any instances wherein vacuum valve 20 (or analogue) becomes closed. This includes the case of closing vacuum valve 20 (or analogue) expressly to measure the viscosity.

The electric-hydraulic analogy thereby provides embodiments of the present invention with a measurable parameter: the time constant, τ, which is the period of time required for quantifiable exponential decay of pressure (which may be accompanied a quantifiable decay of flow rate and a quantifiable decrease in ΔV). This time constant may be used to determine viscosity by a calibration or conversion factor or constant. For an RC circuit, the time constant is the product of the resistance and capacitance: τ=R C. The hydraulic analogue of capacitance is the compliance chamber 30, which exhibits elastic volumetric changes as a function of pressure. One definition of the corresponding hydraulic analogy time constant is given in eq. 12, though other definitions may exist.

$$\tau \propto (\text{compliance}) \times (\text{viscosity});\ \tau \approx K^{*}\mu \qquad \text{Eq. 12}$$

where K* is a dimensioned compliance calibration constant (a function of the compliance) and μ is the fluid viscosity. Dimensional analysis of eq. 12 reveals that the dimensions of K* are inverse pressure $[F^{-1}L^{2}]$; any quantification of compliance (as used herein) may be expressed in units with dimensions of inverse pressure. Eq. 12 employs the mathematical symbol x to denote "proportional to" and symbol~ to denote "approximately equal to." Herein, it is acknowledged that both the electric circuit and the hydraulic analogy produce equations which reflect theory and which have been experimentally confirmed to adequate accuracy expectations; experiments conducted by means of the present invention (viscosity measurement/flow measurement) are subject to experimental error and deviation from the governing equations. Despite any experimental error which may be inherent to aspects of the present invention, the improvements over existing technologies are evident as disclosed herein. To this end, the equal sign, "=", is generally replaced with the approximately equal to sign, "z" herein, particularly for the hydraulic analogue equations. Such unavoidable experimental error may be addressed by standard techniques including curve-fitting and statistical methods as may be required.

The methodology of the present invention includes techniques which may quantitatively determine the aspirate viscosity by measuring, approximating or quantitatively estimating the time constant, τ, of eq. 11; a shorter time constant, τ, is indicative of a less viscous aspirate (saline, blood, etc.), whereas a longer time constant, τ, is indicative of a more viscous aspirate (thrombus-laden blood, clots, etc.). A very long time constant, τ, may be indicative of a clog, whereupon clog-clearing measures may be undertaken automatically by system a system controller or manually by a clinician. Eq. 12 may be used to sequentially calculate the time constant for multiple fluids of varying viscosities. The time constant for saline, $\tau_{saline}$, may be calculated initially within a thrombectomy procedure; the time constant for blood, $\tau_{blood}$, may subsequently be calculated while the distal end of catheter 40 is located in blood. Eq. 13 may then be constructed by dividing eq. 12 by itself at two different values of τ.

$$\frac{\tau_{blood}}{\tau_{saline}} \approx \frac{\mu_{blood}}{\mu_{saline}} \approx \frac{Q_{saline}}{Q_{blood}} \qquad \text{Eq. 13}$$

The compliance chamber constant, K* is thereby algebraically eliminated; there is no need to contemplate or calculate K* because the compliance chamber characteristics remain constant regardless of the viscosity of the fluid contained therein. Eq. 13 introduces a concept which may be employed throughout this disclosure and any implementation of time domain viscometry: ratiometric analysis, wherein the ratio of measured parameters (e.g., time, volume, pressure, flow rate, temperature, etc.) may elicit a corresponding ratio of secondary (not directly measured) parameters (e.g., viscosity, flow rate, volume, thermal conductivity, etc.). The ratio of these time constants is anticipated to be approximately equal to 4 because $\mu_{blood}$≈4 cP and $\mu_{saline}$~ 1 cP. During any subsequent event during a thrombectomy procedure, the calculation of a time constant, $\tau_{unknown}$, that is greater than $\tau_{blood}$ may provide conclusive evidence that the aspirate possesses a viscosity greater than blood, therefore thrombus in the aspirate stream may be inferred. Quantitative measurement of viscosity permits aspects of the present invention to make inferences regarding the aspirate composition, such as distinguishing between blood, 10% thrombus, 20% thrombus, . . . clot, . . . clog, etc. comprising the aspirate. Eq. 13 also provides the relationship between flow rates; this may be in cases where flow, Q, rather than viscosity, u, is the dependent variable in the chosen coordinate system. Eq. 13 is dimensionless.

The graphs disclosed herein have been constructed in the first quadrant in order that visualizing the x-intercept (t-intercept) and slope are familiar to one of ordinary skill in the art of algebra, calculus and/or differential equations. A coordinate transformation between P measured pressure and a relevant parameter, $P/P_0$, may be conducted, such as the example given in eq. 14, which is dimensionless. The coordinate transformation of eq. 14 may be used to normalize pressure such that the initial differential pressure ($\Delta P_{initial}$ of a given cycle) is assigned to be $P_0$ (for that given cycle). Eq. 14 decays from initial value of 1 ($P=P_0$) toward zero as time increases toward infinity.

$$\frac{P}{P_0} = 1 - \left(\frac{P_0 - P}{P_0 - P_{local}}\right) \qquad \text{Eq. 14}$$

where $P_0$ is the initial pressure and $P_{local}$ may have been measured previously. As a numerical example, a pressure transducer output of 400 (approximately atmospheric+venous/arterial pressure) is measured as in FIG. 1*a*; $P1=P_{local}=400$. Subsequently, as in FIG. 3*a*, a pressure transducer output of 100 (approximately 20 inHg vacuum, approximately 25 kPa absolute) is measured; $P3=P_0=100$. Upon closing vacuum valve 20, the measured pressure increases from 100 to 400; the value of $P/P_0$ (after coordinate transformation of eq. 14) decreases from 1 to 0. The coordinate transformation of eq. 14 affords analytical and computational ease facilitating the following mathematical analyses. The term pressure decay may be used herein instead of the term vacuum decay because pressure is a fundamental unit of the analyses presented herein; it is typically pressure that is measured by pressure sensor 70, a separate coordinate transformation may be used to convert the pressure output to vacuum units. Performing the coordinate transformation of eq. 14 permits pressure data (from pressure sensor 70) to be used in the subsequent solutions to eq. 11.

Figure 5A:
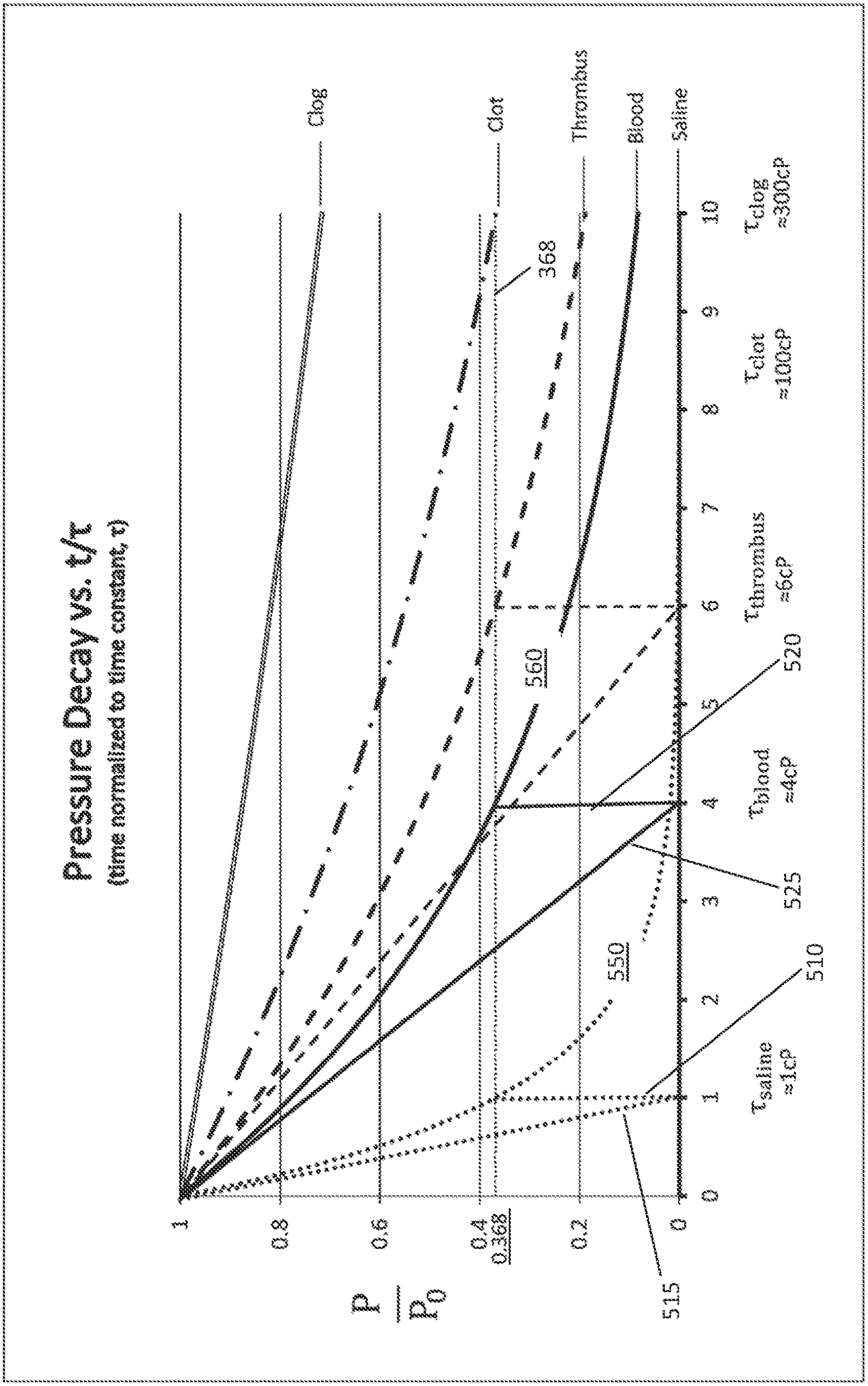
FIG. 5*a* shows the pressure decay traces of 5 representative fluids: saline, blood, thrombus, clot and clog.

FIG. 5*a* shows five representative mathematical solutions to eq. 11 for various values of the time constant, τ; which is the product of the circuit resistance (viscosity) times the circuit capacitance (compliance). Five (5) representative liquids were chosen for the graph of FIG. 5*a*: saline (1 cP), blood (4 cP), thrombus (6 cP), clot (100 cP) and clog (300 cP). The latter are numerically convenient, yet representative examples of higher-viscosity fluids; fluids may reach viscosities as great as 10,000 cP or greater, calculating these would obfuscate the visual utility of the graph of FIG. 5*a*.

FIG. 5*a* shows time-dependent pressure decay traces for five representative fluids (saline, blood, thrombus, clot and clog) which are shown to exhibit five different time constants. The ordinate axis is annotated $P/P_0$; in this graph, pressure is normalized to $P_0$ and is non-dimensionalized. The ordinate axis represents the differential pressure between pressure sensor 70 and $P_{local}$, at the distal end of catheter 40; it is this differential pressure that drives flow through catheter 40. From the electric analogue to the hydraulic circuit model, it is evident that increasing the resistance of variable resistor 140 will increase the time constant, τ; this is validated by the electric circuit definition: τ=R C. Analogously, increasing the viscosity of the fluid in catheter 40 will increase the corresponding time constant in the hydraulic circuit. A more viscous fluid, contained within catheter 40, requires greater time to refill compliance chamber 30 than a less viscous fluid. The present invention may be implemented by: (1) closing vacuum valve 20 and (2) measuring the time required for the compliance chamber 30 to partially refill. It is this time measurement that may be used by the present invention to subsequently calculate the viscosity and flow rate (by the methods of time domain viscometry) analogously to measuring the capacitance and resistance. The coordinate system of FIG. 5*a* shows time as the domain (independent variable) and dimensionless pressure ratio (dependent variable) as the range; the slope of any line in FIG. 5*a* may have the units of inverse time, $t^{-1}$.

The electric circuit shown in FIG. 1*b* through FIG. 4*b* may be used to measure the resistance of variable resistor 140 by measuring the rate of change in voltage. In an electric circuit, voltage is the property which is measured, this voltage measurement is transformed into a resistance measurement by calculating the slope of the voltage decay. Similarly, the hydraulic circuit shown in FIG. 1*a* through FIG. 4*b* may be used to measure the viscosity of the fluid in catheter 40 by measuring the rate of change in pressure, measured at pressure sensor 70. In the analogous hydraulic circuit, pressure is the fluid property which is measured, this pressure measurement may be transformed into a viscosity measurement by calculating the slope of the pressure decay. In the absence of any calibration standard, resistances and viscosities may be quantified on a ratiometric, relative or differential basis. If a first resistor exhibits a time constant, τ", and a second resistor exhibits a time constant of 2τ", then the resistance of the second resistor may be inferred to be two times greater than the resistance of the first resistor. Calibration of the electric circuit may be accomplished by the measurement of any resistor (e.g., 1 kΩ) or, in the hydraulic analogy, any fluid of known viscosity (e.g., saline @ 1 cP). Establishing a single time constant for a fluid of known viscosity (e.g., $\tau_{saline}$), thereby provides a quantitative (ratiometric) relationship between an unknown viscosity ($H_{unknown}$) and the measured time constant which may quantitatively determine $\tau_{unknown}$.

A commercially-available capacitor may provide a linear response; eq. 8 does not provide for the capacitance, C, to change (exhibit non-linearities) with voltage. In reducing aspects of the present invention to practice, compliance chamber 30 is not anticipated to necessarily exhibit a linear response; non-linear compliance chamber 30 volume (with respect to pressure) may not be a linear function of pressure, as measured at pressure sensor 70. This acknowledgement does not detract from the utility of the present invention because any compliance non-linearities are applied equally to all fluids of all viscosities within the measurement range appropriate to the aspects of the present invention. The methodologies of aspects of the present invention may demonstrate that the period of time required for viscometric determination may be small (50 ms to 5 s) compared to the system time constant (1 s to 100 s or greater).

The present invention invokes eq. 11 in that P' (t) (which is the slope the graph of P(t)) is a constant multiplied by the instantaneous pressure, P(t); that constant is −1/τ. A useful feature of the time constant is that it represents the time required for the initial pressure, P (t=0), to decay to a level of approximately 36.8%; therefore:

$$\frac{P(t=\tau)}{P(t=0)} \approx 0.368.$$

An algorithm may be devised such that the pressure is monitored (with respect to time) and thereby determines the time constant, τ, when the pressure has decayed to approximately 36.8% of the initial value. Additionally, certain embodiments of the present invention include numerically calculating or estimating the slope the graph of P(t) at time t=0; projecting this line to the time axis (finding the "x-intercept or the "t" intercept) and thereby providing a numerical estimate of the time constant, τ, of the system. This numerical approximation of P' (t=0) may be accurately calculated using only a small number pressure readings; the slope is continuously changing, therefore the first data points are representative of the initial condition (the instant when vacuum valve 20 is opened). The slope of the line P(t) may be estimated, at any time t, by subtracting successive or flanking pressure readings and dividing by the time interval between the pressure readings (a finite-difference derivative); the time delay between successive pressure readings may be selected for optimized accuracy and system response. Other approaches, such as higher-order finite-difference techniques, may be employed to estimate the slope of a pressure trace with greater robustness and accuracy.

As a graphical aid to conceptualizing the various experimental and computational methods disclosed to determine the time constant for the representative fluid saline, FIG. 5*a* shows vertical saline drop line 510 originating at the intersection of saline trace 550 and 0.368 line 368, and terminating at the time value of $\tau_{saline}$, normalized to 1. A computational method to arrive at the determination of $\mu_{saline}$=1 may be to collect pressure data with respect to time and wait until the point in time where $P/P_0 \approx 0.368$. This requires that the data collection elapsed time is greater than the time constant, which may be greater than 1 second; in the case of very viscous aspirate or a clog, the time constant may be minutes or even hours.

In another embodiment or analytical technique of the present invention, saline slope line 515 is constructed from data points collected in a fraction of the time constant, $\tau_{saline}$; as is characteristic of exponential decay functions, saline slope line 515 intersects with saline drop line 510 at the normalized time axis where $t \approx \tau_{saline} \approx 1$. The present invention utilizes this feature of exponential decay functions to experimentally determine the time constant while collecting and analyzing fewer data points in a shorter period of time. Similarly, FIG. 5*a* shows blood drop line 520 originating at the intersection of blood trace 560 and 0.368 line 368 terminating on time axis at approximately $\tau_{blood}\approx 4$; blood slope line 525 also intersects the time axis at the same t-intercept. Similar graphical constructions or computational methods may be employed to determine the time constants of the remaining representative liquids. The embodiments and methodology of the present invention thereby permit quantitative (ratiometric) determination of the viscosity of any fluid contained within catheter 40; corresponding flow rates may also be quantified, if desired; however the quantitative determination of viscosity may represent a preferred embodiment of the present invention. The foregoing is presented to provide a graphical depiction of pressure decay in real time; alternate methods may also be employed by alternate, similar techniques of the present invention.

Figure 5B:
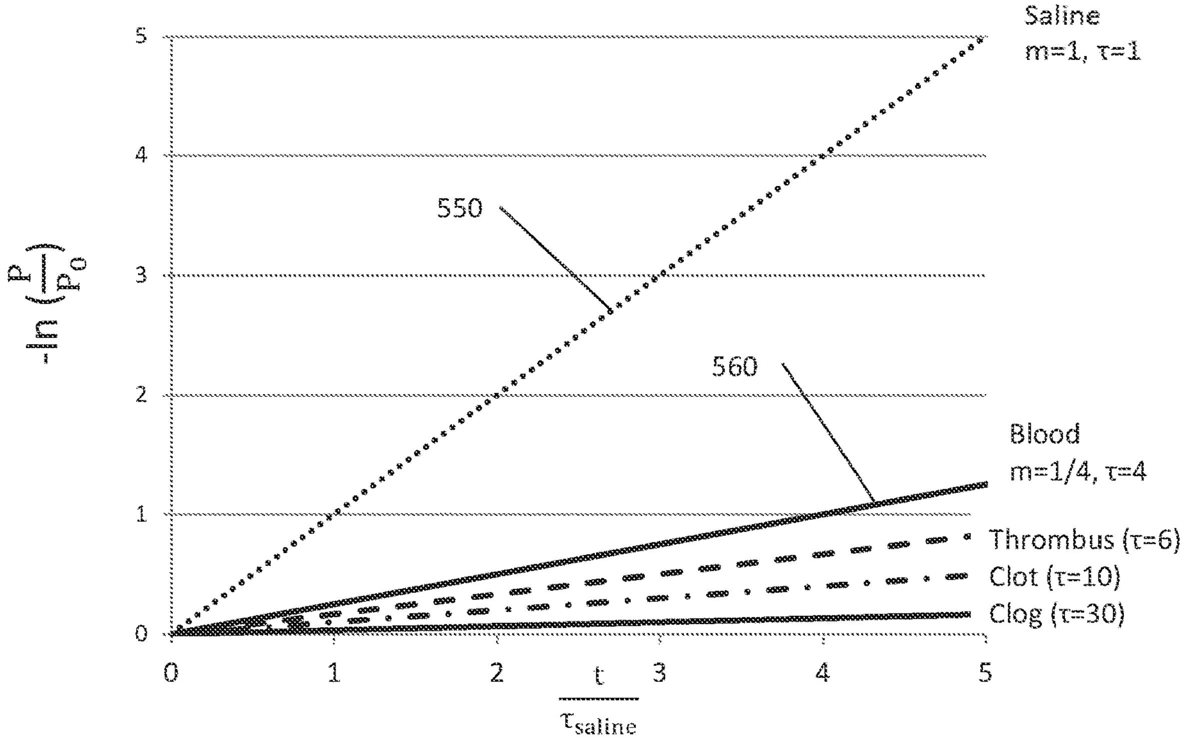
FIG. 5*b* shows the pressure decay traces of FIG. 5*a* plotted in a log-linear graph.

FIG. 5*b* shows the pressure decay curves of the 5 representative fluids plotted on a (natural) log-linear graph in the first quadrant, but depicted with positive slope as a visual aid; the pressure decay is thereby linearized such that the slope is constant throughout the range. This makes calculation of the slope (by finite difference methods, for example) independent of time; in FIG. 5*a*, the slope of each line changes with time; in FIG. 5*b*, the slope remains constant in time. The slope of each line in FIG. 5*a* is related to the viscosity by eq. 15, which may be derived from taking logarithms and derivatives of eq. 11.

$$\frac{d}{dt}\left(\ln\frac{P}{P_0}\right)\approx\frac{-1}{\tau} \qquad \text{Eq. 15}$$

Embodiments of the present invention may include calculation of the time derivative of the logarithm of pressure (measured at pressure sensor 70); this time derivative is the negative reciprocal of the slope of the pressure decay line plotted on log-linear scales in FIG. 5*b*. Eq. 15 makes the calculation of the slopes of pressure decay lines independent of time; the slope of the pressure decay curve may be calculated at any time during the first time constant with good accuracy. FIG. 5*b* is intentionally constructed such that the slope is positive for ease of applying relevant algebraic operations in the first quadrant. FIG. 5*b* is constructed with a non-dimensional domain by normalizing the time to a system constant time, $\tau_{saline}$, which may range from approximately 0.1 seconds to in excess of 60 seconds. FIG. 5*b* is shown in dimensionless form; the dependent variable units of time may be restored by multiplying ordinate by the system time constant, $\tau_{saline}$.

FIG. 5*a* depicts the theoretical pressure/voltage decay of an ideal, linear compliance chamber/capacitor; the data appear curvilinear in Cartesian coordinates. FIG. 5*b* depicts the same data after a linearizing coordinate transformation. Any such linearization scheme is an optional constituent of the present invention; FIG. 5*b* is included herein as a visual aid. Aspects of the present invention include quantitative approximation of the slope of the pressure decay trace to quantitatively measure or infer fluid viscosity; linearization may or may not be incorporated. As an example, to measure or estimate the slope of any pressure trace at a point or throughout a range, a preferred embodiment of the present invention is to use finite difference approximations to estimate the slope from a number of data points (pressure measurements); an example finite difference technique is shown in eq. 16:

$$\frac{d}{dt}(\ln P)\approx A\left(\ln\overline{P}_{t-j}-\ln\overline{P}_{t+j}\right);\ \frac{d}{dt}(\ln P)\propto\left(\ln\overline{P}_{t-j}-\ln\overline{P}_{t+j}\right) \qquad \text{Eq. 16}$$

Where $\overline{P}_{t\pm j}$ is the (averaged or otherwise data-conditioned) pressure measurement at any time t minus or plus an offset of j data points and A is an arbitrary constant (proportional to the experimental time interval) with units of inverse seconds. $\overline{P}_{t\pm j}$ may be an average of approximately two to 1,000 or more data points depending upon the speed of the processor, response time of the sensor, etc. As j is increased, a greater range of data points may be analyzed, effectively approximating the slope over a range; as j is decreased a smaller range of data points are analyzed, effectively approximating the slope at a point. For computational efficiency, the arbitrary constant A may assume unit value and the (unscaled) slope of the line may be estimated by the difference in two or more pressure measurements. The resultant unscaled slopes may be ratiometrically compared to perform differential viscometry. In eq. 16, the natural logarithm function of pressure is used in this embodiment; in practice, any function of pressure may be used. The second form of eq. 16 illustrates that the time derivative of InP, d/dt (InP), is proportional to a quantity which may be calculated by finite difference methods. Division of eq. 16 (calculated for a first fluid) by the same eq. 16 (calculated for a second fluid) yields a dimensionless ratio; this further illustrates that contemplation and calculation of the arbitrary constant A is generally unnecessary. Raw data may be averaged or conditioned (to reduce noise and error) by standard data conditioning techniques (e.g., weighted average, moving average, etc.).

The logarithm function of eq. 16 is illustrative of any function which may linearize or otherwise transform the data; the untransformed time derivative of the pressure trace may be used. Many alternate techniques may be employed to analyze the pressure data including linear regression, curvilinear regression, any-order spline, etc. Finite difference approximations of the slope may represent an optimized technique to extract the desired information from the fewest number of data points; this may decrease the time required to complete the measurements and computations. Depending upon factors including processor speed and transducer response, the time interval between pressure successive measurements may be approximately 10 μs to 1 s; this may be a function of processor speed, coding efficiency, multitasking capabilities, etc. As an example of a representative commercially available controller, an Arduino Uno collects data at approximately 800 μs intervals, or about 1,250 samples per second. Adequate data for analysis may be acquired with approximately 300 to 600 such data points; these data may be collected in less than approximately 500 ms. Time domain viscometric analysis may thereby occur in less than one second using inexpensive, off-the-shelf equipment.

FIG. 5*b* shows 5 straight lines corresponding to the 5 representative fluids; the ordinate of the graph is chosen to be −In $(P/P_0)$ such that the slopes of the pressure decay lines are positive; the slope (m) of each line is the reciprocal of the (dimensional or dimensionless) time constant, τ, for any given fluid. The slope, m, of the saline line is approximately 1 ($m_{saline}$~ 1), therefore the time constant is also approximately 1 ($\tau_{saline}\approx 1$); similarly, $m_{blood}\approx 1/4$, therefore $\tau_{blood}\approx 4$, $m_{thrombus}\approx 1/6$, therefore $\tau_{thrombus}\approx 6$, etc. The abscissa of FIG.

5*a* and FIG. 5*b* is dimensionless due to normalizing the axis to calibration or reference data, $\tau_{saline}$, by the coordinate transformation $$t => \frac{t}{\tau_{saline}};$$

this normalizes the slope of saline to $m_{saline} \approx 1$, from which viscosities of other fluids may be ratiometrically determined.

FIG. 5*a* shows the pressure decay traces of various fluids in a linear graphical coordinates; three methods of solving for the time constant are presented: A first method is waiting for the pressure trace to cross the 0.368 line 368; a second method is by estimating the slope at a point or a range by finite difference methods. The third method is to numerically approximate the slope of any pressure trace by employing data linearlization (e.g., the log-linear graphical technique of FIG. 5*b*) and employing finite difference techniques such as presented in eq. 16.

Figure 5C:
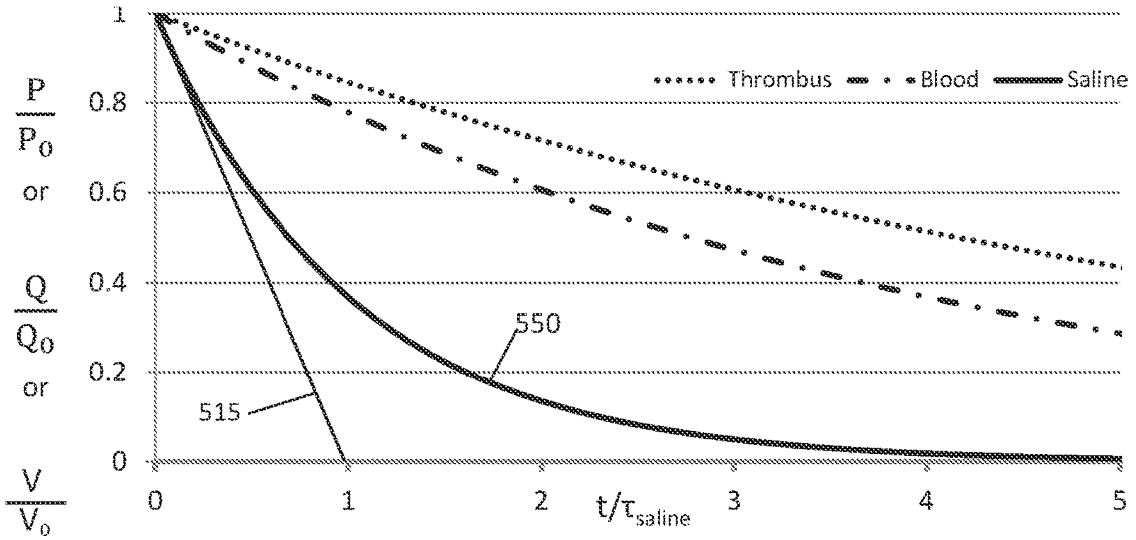
FIG. 5*c* shows the time decay traces of pressure, flow and volume.

FIG. 5*c* shows the pressure decay graph of FIG. 5*a*, with only three fluids (saline, blood and thrombus) for clarity. The ordinate is labeled in three dimensionless parameters: pressure, flow and volume. Saline slope line 515 and saline trace 550 are also shown in FIG. 5*c*; saline slope line 515 is a line with slope equal to the slope of saline trace 550 at time at or near approximately zero. Saline trace 550 exhibits maximum slope (−1) at t=0; the slope of saline trace 550 continuously increases toward zero as pressure decreases toward zero. FIG. 5*c* is subsequently discussed after flow rate and displacement volume are defined in context of subsequent figures.

Figure 6:
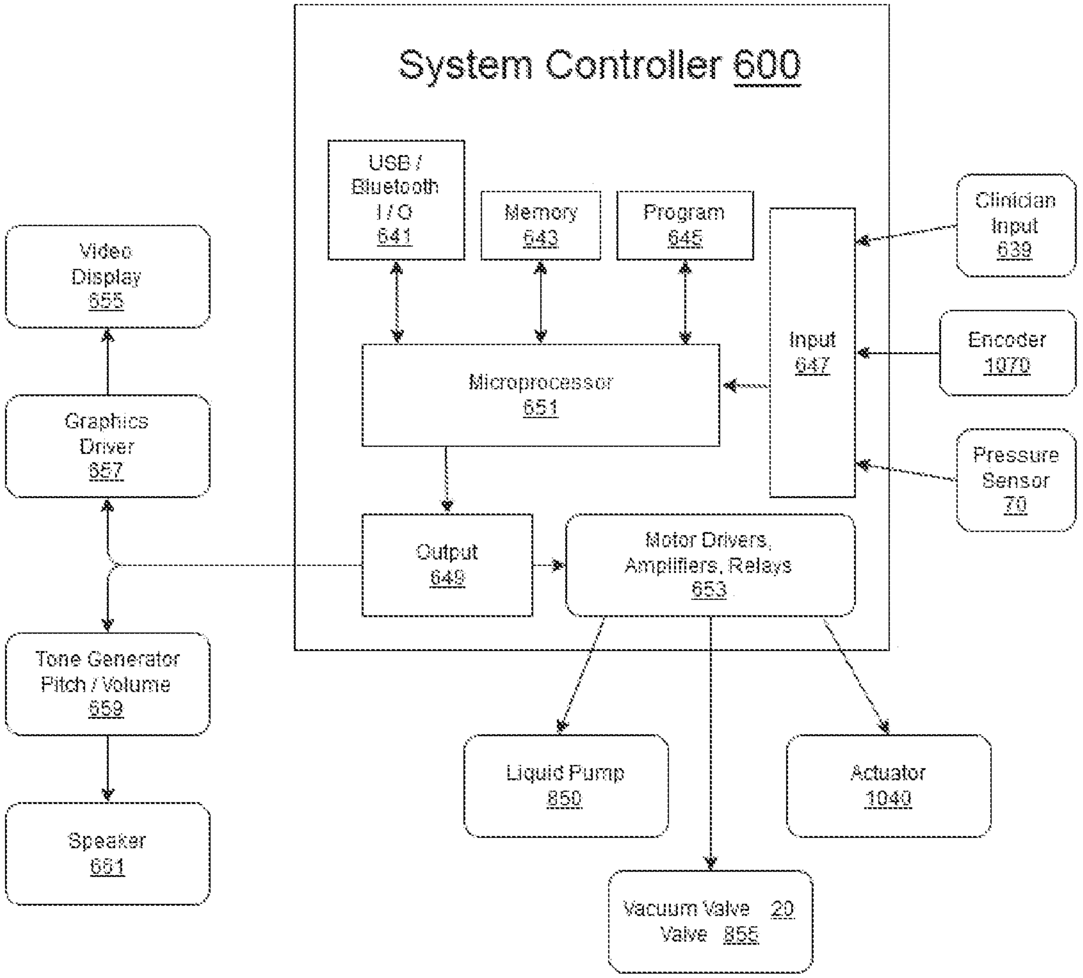
FIG. 6 shows a block diagram of a representative thrombectomy system controller.

FIG. 6 shows a block diagram of representative system controller 600 which, in preferred embodiments, may employ machine evaluation of conditional statements with variable data, calibration data, patient data and predetermined values as arguments. The outcomes of evaluating such conditional statements may be employed by resident software or program 645 to select a thrombectomy operating mode, such as clog clearing 830, clot clearing 832, thrombus extraction routines 834, 836, etc.

System controller 600 may comprise microprocessor 651 and input 647, which may be comprised of clinician input 639, encoder 1070 and pressure sensor 70. Clinician input 639 may include tasks such as positioning of the thrombectomy catheter, as well as thrombectomy mode selection/override or initiating a calibration or viscometric inflow sampling routine. Clinician input 639 may be accomplished by the use of keyboards, trackballs, mice, knobs, switches, etc. (not shown). Microprocessor 651 accesses memory 643, program 645, and USB/Bluetooth I/O 641. Output 649 may comprise clinician feedback and/or control of system components. Clinician feedback may comprise visual feedback such as may be provided by graphics driver 657 and video display 655 as well as audio feedback such as may be provided by tone generator 659 and speaker 661. Example embodiments of output 649 may include motor drivers, amplifiers, relays 653, which may control components such as liquid pump 850, actuator 1040, vacuum valve 20 and valve 855. For simplicity in FIG. 6, each component is depicted individually; each depicted component may comprise a plurality of components.

Microprocessor 651 represents one or more general-purpose processing devices such as a microprocessor, central processing unit, or the like. More particularly, microprocessor 651 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. Microprocessor 651 may also be one or more special-purpose processing devices such as an application specific integrated circuit (ASIC), a field programmable gate array (FPGA), a digital signal processor (DSP), network processor, or the like. Microprocessor 651 may be capable of executing instructions stored in program 645 and/or memory 643, including instructions corresponding to the method of FIG. 7 and FIG. 8, of reading data from and writing data into memory 643, and of receiving input signals and transmitting data or signals to output 649. While single components are depicted in FIG. 6 for simplicity, system controller 600 might comprise a plurality of components which are depicted singly. Components such as memory 643 and program 645 are depicted in FIG. 6 as discrete components; any such components may be consolidated to a single component. Components and/or functions of system controller 600 may be consolidated into one or more proprietary or commercially available single board computers, such as Arduino, Raspberry Pi, Asus Tinker Board, etc. Multitasking (such as independent pump/pressure control and pressure measurement) may be facilitated by the use of a plurality of microprocessor 651 components.

Figure 7:
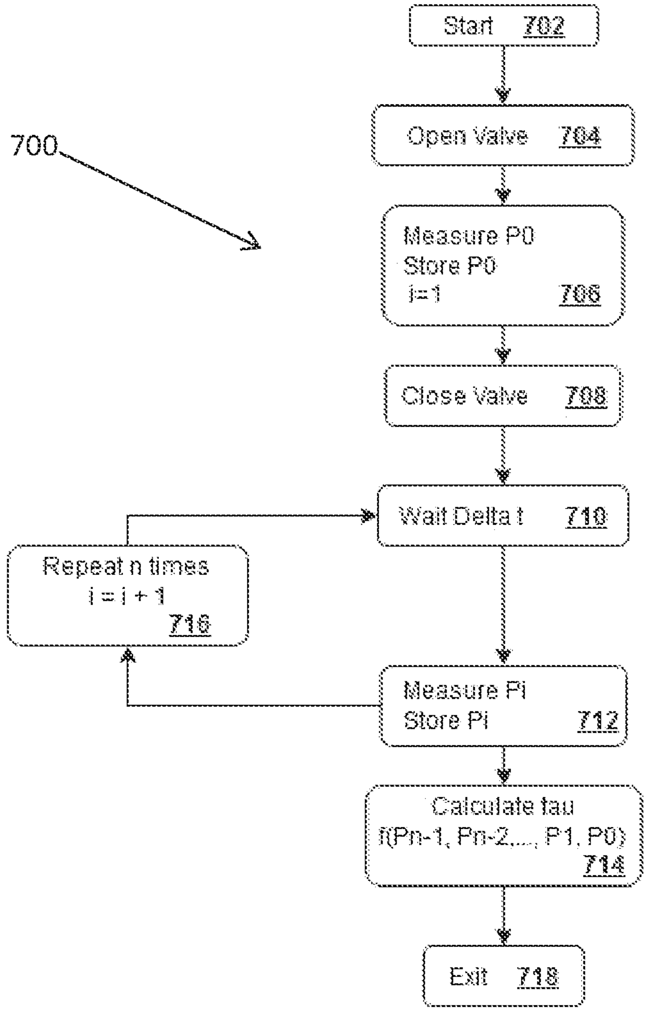
FIG. 7 shows a representative subroutine flowchart for calculating the time constant, $\tau$, for any fluid.
Figure 8:
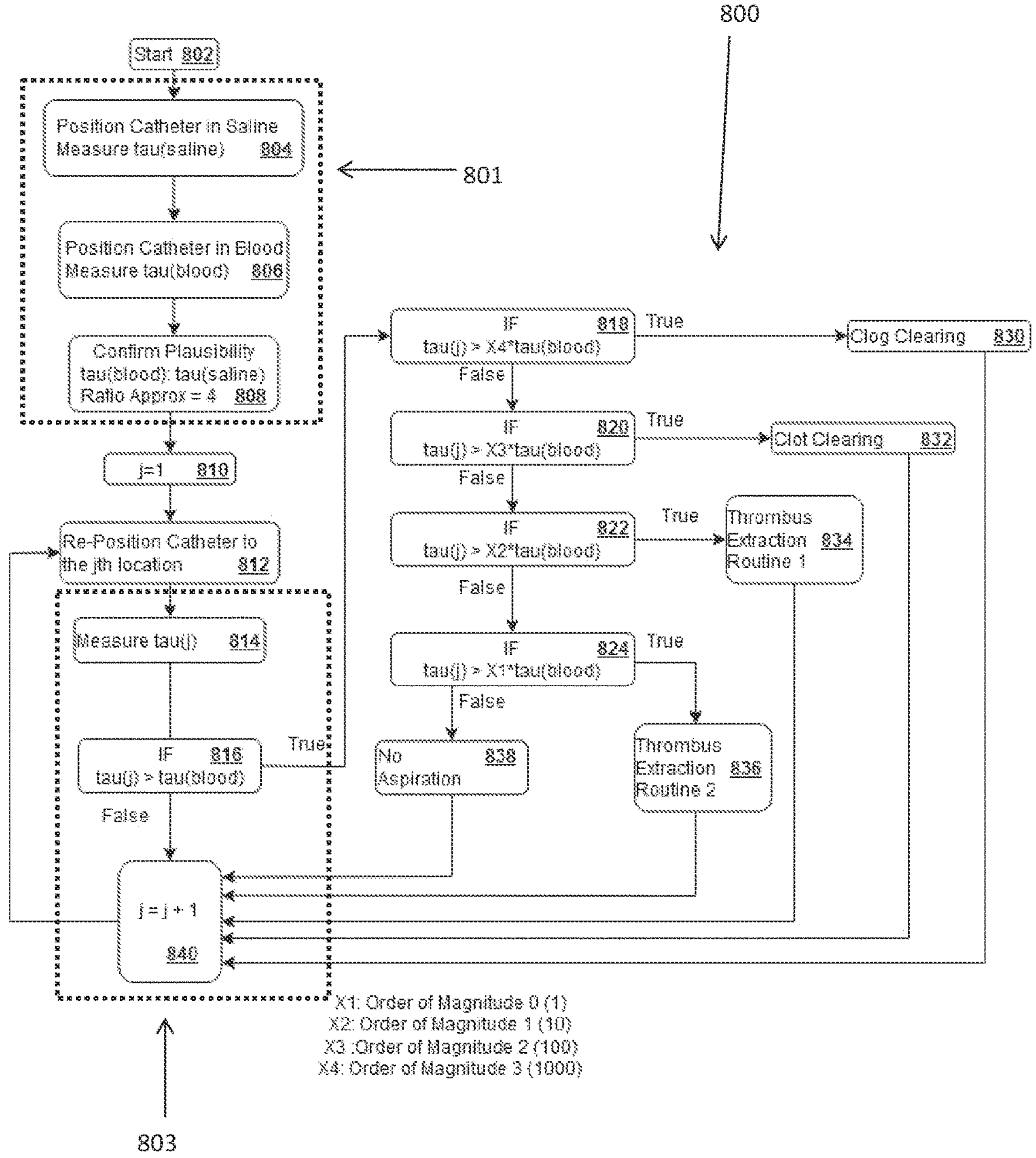
FIG. 8 shows a representative flowchart for a thrombectomy procedure.

Memory 643 and/or program 645 may be capable of storing executable instructions and data, including instructions and data corresponding to the method of FIG. 7 and FIG. 8, and may include volatile memory devices (e.g., random access memory [RAM]), non-volatile memory devices (e.g., flash memory), and/or other types of memory devices. Memory 643 and/or program 645 may be capable of persistent storage of executable instructions and data, including instructions and data corresponding to the method of FIG. 7 and FIG. 8, and may include a magnetic hard disk, a Universal Serial Bus [USB] solid state drive, a Redundant Array of Independent Disks [RAID] system, a network attached storage [NAS] array, etc.

FIG. 7 shows an example calculate tau subroutine 700 which may be executed by the methodologies of the present invention to calculate the time constant, τ, for any fluid in catheter 40. The calculate tau subroutine 700 is initiated at start 702, vacuum valve 20 or valve 855 is opened (upon the open valve 704 instruction). A time delay may occur. Data for initial pressure P0 are collected and stored in the measure P0 706 step; the index counter, i, is initialized to 1. Vacuum valve 20 is closed (upon executing the close valve 708 instruction); a time delay for flow in catheter 40 to be established during wait delta t 710 instruction. The duration of wait delta t 710 may be optimized to allow for an adequate change in pressure such that the slope may be calculated with improved accuracy; this may be dependent upon factors such as signal-to-noise ratio (SNR), the fluid viscosity, the system time constant, etc.

P1 is measured (i=1) by executing measure Pi 712 instruction; P1 is stored. The repeat n times 716 instruction subsequently collects and stores data (example: P4, P3, P2, and P1 for n=3). Executing calculate tau 714 instruction calculates the time constant, tau, for the fluid contained within catheter 40. Exit 718 may return control to another program. FIG. 7 is a representative algorithm to calculate tau for a suction thrombectomy system as illustrated in FIG. 1*a* through FIG. 4*a*, wherein a vacuum reservoir 10 and valve 20 are illustrated as aspiration means. The example calculate tau 700 subroutine may be similarly constructed for other aspiration means including liquid pumps. For other aspiration means, steps wait delta t 710, measure Pi 712, repeat n times 716 and calculate tau 714 may remain essentially as shown in FIG. 7; whereas generation of the requisite differential pressure may deviate from the depicted open valve 704 and close valve 708 examples in FIG. 7. The duration of wait delta t 710 may range from 1 μs to 10 s depending upon application; preferred embodiments may be exhibit a delta t duration between 300 μs and 1 s. Of course, the duration of wait delta t 710 may be approximately zero, such that the next instruction may be executed without a time delay.

FIG. 8 shows an example thrombectomy flowchart 800 which repeatedly invokes the calculate tau subroutine 700 upon execution of the instruction measure tau (j) 814. Upon power-up, reset or other input, the thrombectomy flowchart is initiated at instruction start 802. Upon execution of step catheter in saline 804, the catheter 40 is positioned (by the user) in saline and the measure tau subroutine 700 is executed; the value tau (saline) is stored. Subsequently, the user positions the catheter 40 in blood thereby executing step position catheter in blood 806; the value tau (blood) is stored. The optional confirm plausibility 808 step may verify the ratio of tau (blood) to tau (saline), which may be approximately 4:1. In some embodiments, calibration 801 may provide system controller 600 with viscometric data collected upon both saline and blood; finite-difference techniques, regression, curve-fitting, extrapolation and other functions of these calibration data may provide arguments for conditional statements which may be evaluated by system controller 600. In some embodiments, calibration 801 may be performed upon a single fluid (e.g., saline, blood, etc.); calibration 801 may be performed a plurality of times during any representative thrombectomy procedure (not shown).

At the conclusion of initial calibration 801, index counter, j, is initialized to 1 in step initialize j 810. Catheter 40 is repositioned, by the user, to a treatment location within the patient vascular system in step reposition catheter 812; catheter 40 is positioned in the first location (j=1), and tau is measured by executing measure tau 814 instruction, which transfers control to measure tau subroutine 700 of FIG. 7. The measure tau subroutine 700 returns the value of tau (1), which is mathematically compared to tau (blood); this mathematical operation may include subtraction, division, statistical techniques or any mathematical function. If tau (1) is not inferred to be greater than tau (blood), execution of the conditional statement (step) tau>blood 816 returns the value of false; index counter, j, is incremented in step increment j 840. Catheter 40 is repositioned to the second location (j=2) by the user in step reposition catheter 812. Catheter 40 may similarly be repositioned repeatedly while tau (j) is not inferred to exceed tau (blood), the clinician thereby seeking intravascular locations where thrombus may exist. Catheter 40 may be held approximately stationary while tau (j) is inferred to exceed tau (blood), thereby providing time for any thrombectomy operating mode to be executed to aspirate thrombus.

Viscometric inflow sampling 803 is an example thrombectomy operating mode wherein aspirate viscosity is measured and, while the aspirate is inferred to be blood, may repeat indefinitely or to a preset value. The viscometric inflow sampling 803 thrombectomy operating mode is shown to transfer control to other thrombectomy operating modes upon detection of thrombus in the aspirate. Quantitative viscometric measurement of the aspirate characteristic may provide system controller 600 with patient (variable) data for evaluation as arguments of conditional statements; calibration data (analysis or functions thereof) may be used as additional arguments in conditional statements. Reference data (from ROM, database or preset value) may be used as arguments.

Upon any instance of step tau>blood 816 returning the value of true, the magnitude of tau (j) may be bracketed, in certain embodiments, to infer attribute data in the successive steps; the magnitudes are bracketed such that a number of representative system responses may be invoked, e.g., clog clearing 830, clot clearing 832, thrombus extraction routine 1 834, thrombus extraction routine 2 836 or no aspiration 838, etc. The representative system responses may be to execute any temporal combination of aspiration rates and infusion rates, as elsewhere described in the references. Execution of conditional statement (step) tau 1000× blood 818 establishes if tau (j)>1000×tau (blood); this may be indicative of a clog in catheter 40; similarly execution of steps tau (j)>100×tau (blood) 820, tau (j)>10×tau (blood) 822, tau (j)>1×tau (blood) 824, bracket or characterize the magnitude of the viscosity of the fluid in catheter 40. Thrombectomy operating modes such as clog clearing 830, clot clearing 832, thrombus extraction routine 1 834, thrombus extraction routine 2 836 or no aspiration 838 may be executed depending upon the magnitude of the viscosity in the $j^{th}$ iteration of thrombectomy flowchart 800. The selection of multipliers X1, X2, X3 and X4 are chosen to be orders of magnitude in this representative example; in practice any increasing function may be employed to determine the value of the multipliers. The order of magnitude selection of the values of X1, X2, X3 and X4 illustrates a 1,000:1 rangeability or "turndown ratio" of the instrumentation; this in contrast to prior art which returns only attribute data (flow, clot, clog, . . . ). In practice, this turndown ratio may range from 10:1 to in excess of 10,000:1. This ratio may be a function of the maximum viscosity which may be measured.

In-situ calibration 801 routines (which may be stored in program 645) or other methods, as aspects of the present invention, may provide system controller 600 with calibration data for subsequent use as arguments of conditional statements. The present invention discloses the use of calibration data (including intra-procedure calibration data) which is distinct from prior art which may employ reference data as arguments of conditional statements. A drawback of prior-art approaches employing such reference data is that the reference data might have been collected (1) not upon the apparatus in use, (2) not at the time of use and (3) not upon the patient under treatment. Furthermore, the reference data may incorporate arbitrary constants which may bias the outcome of any conditional statement to a preferred or erroneous outcome. As an example, preferred embodiments of the present invention may evaluate the conditional statement (IF measured value<=f (calibration data), THEN execute task Z); whereas prior art provides conditional statements which may be of the form (IF measured value<=reference/preset value, THEN execute task X). Calibration 801 may be performed by measuring the viscosity of homogeneous sample data, e.g., catheter in saline 804 and/or catheter in blood 806. Homogeneous calibration data for blood may be collected at a non-diseased (thrombus-free) location within the patient vascular system; subsequent to calibration, heterogeneous data may be collected and analyzed from diseased (thrombus-containing) locations. Subsequent to calibration, aspirate inflow may be heterogeneous data, as the viscosity of the aspirate may be a function of time. As catheter 40 is repositioned (step reposition catheter 812) within the vasculature, thrombus may be encountered and aspirated; any heterogeneous data may be evaluated by system controller 600 to determine the aspirate viscosity. Upon determination of the aspirate viscosity, system controller 600 may select a thrombectomy operating mode based upon the magnitude of the aspirate viscosity. Note that in cases where tau>tau (blood) 816 returns the value of "false," then the sample is generally discarded to waste; no aspiration 838 also generally discards the sample to waste. This highlights the importance of small sample volume for viscometric inflow sampling 803, preferred embodiments the present invention may utilize sample volumes that are less than 1 cc.

FIG. 9*a* through FIG. 9*f* shows a representative embodiment of a "collapsible bulb" or "squeeze bulb" or "turkey baster" type compliance chamber 900 at 3 different volumetric states. As shown in FIG. 9*a* through FIG. 9*f*, the standalone deformable structure of FIG. 9*a* through FIG. 9*f* is prior art, yet is included to illustrate: (1) the change in volume with deformation and (2) that reduced internal pressure (as well as external forces) may cause the compliance chamber 900 to collapse to a smaller volume. A viscometer comprising a collapsible bulb type compliance chamber 30, 900 (in addition to other components) is presented herein as an embodiment of the present invention. Ancillary system components of a representative embodiment including: system controller 600, vacuum reservoir 10, vacuum valve 20, catheter 40, pressure sensor 70, etc. are not shown in FIG. 9*a* through FIG. 9*f* for clarity. Collapsible bulb compliance chamber 900 is shown in FIG. 9*a* through FIG. 9*f* to be open on both ends; ancillary system components (not shown in FIG. 9*a* through FIG. 9*f*) provide differential pressure to deform and/or permit fluid flow to compliance chamber 900. Some embodiments may comprise intermittent or cyclic application of differential pressure and the opening/closing of any flow control mechanism, such as vacuum valve 20, liquid pump 850 or peristaltic pump 100.

Figure 9A:
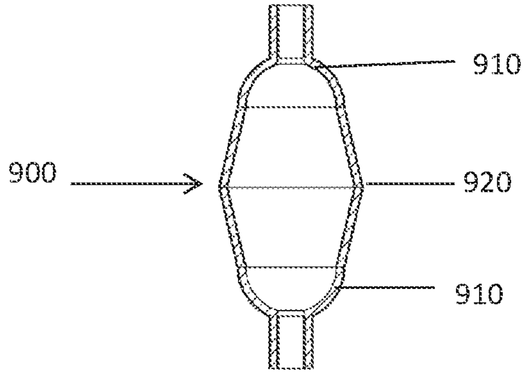
Fig. 9a Prior Art
FIG. 9*a* shows a cutaway view of a compliance chamber embodiment at or near maximum volume.
Figure 9B:
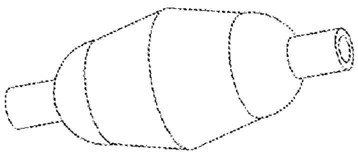
Figure 9C:
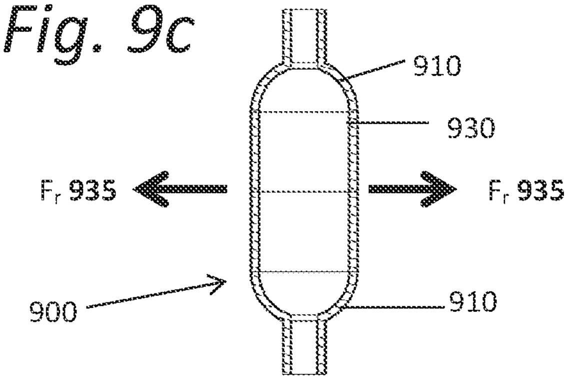
Figure 9D:
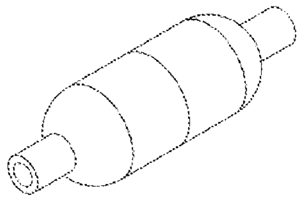
Figure 9E:
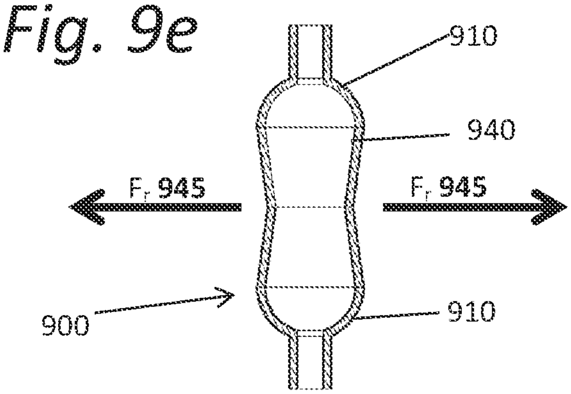
Figure 9F:
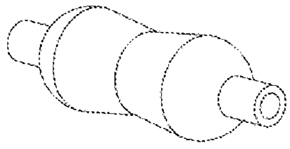
FIG. 9*f* shows a perspective view of the compliance chamber of FIG. 9*e*.

Collapsible bulb compliance chamber 900 is represented in FIG. 9*a* through FIG. 9*f* as a generally cylindrical structure exhibiting a different diameter than the flanking tubing; the collapsible bulb may also be designed and fabricated to incorporate changes in wall thickness and materials of construction. In some embodiments, a length of tubing may act as an alternative embodiment of depicted compliance chamber 30, 900. FIG. 9*a* shows a section view of compliance chamber 900, 2 inlet/outlet 910 sections and a central section shown in the nominal 920 configuration; such an expanded state may arise when the internal pressure is (greater than or) approximately equal to the external pressure. Compliance chamber 900, in nominal 920 configuration (of FIG. 9*a*), may represent the configuration of FIG. 1*a*, wherein volume V1 is at or near maximum. FIG. 9*b* shows the expanded or nominal compliance chamber 900 of FIG. 9*a* in oblique view. FIG. 9*c* shows a section view of compliance chamber 900 in an intermediate 930 configuration; such an intermediate state may arise when the internal pressure is decreased/decreasing below the external pressure, which may be representative of FIG. 2*a*, wherein volume V2 is less than volume V1. FIG. 9*d* shows the intermediate compliance chamber of FIG. 9*c* in oblique view. FIG. 9*e* shows a section view of compliance chamber 900 in a contracted 940 configuration; such a contracted state may arise when the internal pressure is further decreased below the external pressure, which may be representative of FIG. 3*a*, wherein volume V3 is less than volume V2 and V1. FIG. 9*f* shows the contracted compliance chamber of FIG. 9*e* in oblique view. The embodiments of FIG. 9 also provide for compliance from gasses or vapors within any of the embodiments presented herein; gasses and vapors are considered herein to be non-isovolumetric components in a thrombectomy system which may serve as generalized compliance chambers. FIG. 9 illustrates an embodiment of compliance chamber 30, 900 wherein tubing segments of different properties (diameter, wall thickness, material of construction, hardness, durometer, etc.) are joined thereto to form a continuous fluid pathway. Methods to join or bond the tubing segments include: adhesives, heat seals, compression fittings, barb fittings, quick-disconnect fittings, etc. Either or both tubing segments (flanking compliance chamber 900 may exhibit non-isovolumetric properties through deformation phenomena including: distension, expansion and contraction. Illustrations of collapsible bulb compliance chamber 900 (identified as prior art) are shown to depict a transition, interface or discontinuity between compliance chamber 900 and surrounding tubing. Embodiments of the present invention may also comprise a (more or less) continuous length of flexible tubing acting as compliance chamber 900. Embodiments and methods may comprise the application and removal an external (surface, contact) force which deforms non-isovolumetric components; a peristaltic pump 100 represents an example thereof. The illustrated scale of collapsible bulb prior art may range from displacement of approximately 5 cc to 500 cc (cubic centimeters). Prior art is included to contrast embodiments of the present invention that comprise other structures including arbitrary lengths tubing (of sufficiently compliant construction) acting as compliance chambers 30, 900. Preferred embodiments of the present invention feature the smaller scale of peristaltic pump tubing acting as compliance chambers 30, 900, wherein the displacement of peristaltic pump tubing may range from approximately 0.01 cc to 5 cc.

The temporal sequence depicted in FIG. 9*a* through FIG. 9*f* provides a visual guide for the correlation between pressure, flow and volume. FIG. 9*a* is depicted at maximum volume and FIG. 9*e* is depicted at minimum volume of a representative cycle or iteration; the nominal configuration of FIG. 9*a* is stated to represent the equilibrium condition where the internal pressure is generally equal to the external pressure ($\Delta P \approx 0$, $P \approx 0$, referencing ambient pressure). The configuration of FIG. 9*a* may be changed to that of FIG. 9*e* by at least two means: external force (e.g., a hand squeezing the compliance chamber 900) or differential pressure ($\Delta P$) between the interior and exterior of compliance chamber 900. The configuration depicted in FIG. 9*e* represents: (1) maximum differential pressure ($\Delta P$ or P) and (2) minimum volume (V); at equilibrium with both ends of compliance chamber 900 sealed off by ancillary system components. At some point in time, fluid is permitted to enter into collapsible bulb compliance chamber 900. With flow established, eq. 2 and eq. 3 assert that flow rate (Q) is proportional to $\Delta P$; it follows that the configuration of FIG. 9*e* is a maximum flow, minimum volume configuration. The configuration of FIG. 9*a* is at or near a minimum flow, maximum volume configuration; while FIG. 9*c* depicts and intermediate configuration. Assuming a linear correlation between pressure and volume for the depicted compliance chamber 900, pressure and flow rate proportional to one another and inversely proportional to compliance chamber 900 volume. It intuitively follows that when differential pressure (P or $\Delta P$) is large, then flow (Q) is also large, (in concert with eq. 2 and eq. 3) and compliance chamber 900 volume is small. Therefore, compliance chamber 30, 900 volume is inversely proportional to both flow (Q) and differential pressure ($\Delta P$);

subsequently a coordinate transformation will be introduced to make flow (Q), differential pressure (ΔP) and volume all proportional to one another. This coordinate transformation enables consistent mathematical and computational techniques to be applied to the three relevant parameters to be measured: pressure, flow and volume.

FIG. 9*c* shows small restoring force 935 (Fr) acting radially outward from compliance chamber 900 in intermediate 930 configuration, and FIG. 9*e* shows large restoring force 945 (Fr) in contracted 940 configuration. FIG. 9*a* does not show and restoring force (Fr) as nominal 920 configuration is stated to be or near at static equilibrium (internal and external pressures are approximately equalized). To transition from the nominal 920 configuration to the intermediate 930 configuration to the contracted 940 configuration, at least two plausible methods exist: (1) decreasing the internal pressure and/or (2) application of an external force including examples such as a hand, a gripper, or a peristaltic pump roller, etc. . . . Decreasing the internal pressure of compliance chamber 900 may cause compliance chamber 900 to "collapse" and contain less volume; fluid transfer outward (from compliance chamber 900) may also occur. FIG. 9*e* illustrates compliance chamber 940, in an operational collapsed 900 configuration, which exhibits a lower internal pressure than atmospheric or nominal pressure. It is restoring forces 935, 945 that may provide operational differential pressure (ΔP and/or Δp) that may induce flow in catheter 40. Embodiments of the present invention comprise: a charging step wherein compliance chamber 900 is operationally reduced in volume to a configuration such as depicted as collapsed 940 in FIG. 9*e*. The degree of volumetric reduction achieved (e.g., 10%, 20%, 50%, etc.) may be immaterial in reducing a time domain viscometer to practice; successive cycles may exhibit different volumetric reduction without consequence to functionality, accuracy, precision, etc. With each cycle, or charging step, the internal pressure and volume of compliance chamber 900 may be normalized and/or non-dimensionalized to one. The foregoing assumes a "linear" compliance chamber 900 or compliance chamber 900 operating in a generally linear fashion between two endpoint volumes and/or pressures for each cycle. Subsequent to the charging step, restoring force 935, 945 force the walls of compliance chamber 900 outwardly against atmospheric pressure; the magnitude of this force may affect the internal pressure (ΔP) within compliance chamber 900. Reduced internal pressure (ΔP) across the impenetrable wall(s) of compliance chamber 900 may provide differential pressure (Δp) between approximately opposite ends of catheter 40, such that flow of aspirate through catheter 40 may exist. Experimentation may be required to assess, measure or validate the assumption of linearity of compliance chamber 900. In the event that non-linearities are discovered, such as by experimentation (or other means), operational limits upon the degree of volumetric reduction may be imposed such that the compliance chamber is operated within a generally linear range, or other methods may be invoked.

Displacement volume (V, or simply volume) is herein generally referenced (by convention) to be zero at the nominal or static equilibrium condition depicted in FIGS. 9*a* and 9*b*; thus, the displacement volume (V) of FIG. 9*a* is stated to be zero (by convention). FIG. 9*e* and FIG. 9*f* show displacement volume to be at maximum and FIG. 9*c* and FIG. 9*d* show displacement volume to be at an intermediate value. FIG. 9*a* and FIG. 9*b* depict static equilibrium with equal internal pressure and external pressure and zero displacement volume; both ends of collapsible bulb compliance chamber 900 are stated to be open to atmosphere. Flow rate (Q) into or out of compliance chamber 900 may be defined as the time rate of change of the displacement volume or Q=dV/dt. The compliance chamber 900 embodiment FIG. 9*a* through FIG. 9*f* (annotated as prior art) is used herein to define and measure the relevant quantities flow rate (Q) and volume (V).

Returning to FIG. 5*c*, the ordinate axis is labeled P/P. or $Q/Q_0$ or $V/V_0$ where P and Q are asserted to be proportional by eq. 3; displacement volume, as utilized herein by convention, is asserted to be proportional to P from intuition and the depictions of FIG. 9*a* through 9*f*. The time decay for pressure, flow and volume are shown for three fluids, saline (μ≈1 cP), blood (μ≈4 cP) and thrombus (μ≈30 cP). A representative cycle or iteration of time domain viscometry is detailed and examined: initial conditions are represented in FIG. 9*a*, where P=0, V=0 and Q=0. As defined and illustrated previously, P (or ΔP) is a differential pressure between the interior and exterior regions of compliance chamber 900 and V is a displacement volume from equilibrium of the same component; P and V are generally non-negative quantities which share a zero datum with the static equilibrium condition depicted in FIG. 9*a*. In the following descriptions, (differential) pressure (P or ΔP) and (displacement) volume (V or ΔV) are described and shown to increase in magnitude as the configuration of FIG. 9*a* is operationally changed to the configuration of FIG. 9*e*. These deviations from equilibrium are expressed as non-negative quantities; this convention is utilized for graphical and mathematical convenience. As an example, the displacement volume V is shown in FIG. 5*c* to be a maximum value (normalized to 1 at time t=0); the value of V decreases over time to approach zero as time approaches infinity.

As differential pressure or external force is applied and compliance chamber 900 is shown collapsed and in a static equilibrium configuration as depicted in FIG. 9*e*, where $P_0$=P=max, $V_0$=V=max and again Q=0 (because dV/dt=0 at equilibrium conditions). $P_0$ is measured, specific to this cycle or iteration, and may be set equal to the maximum differential pressure (ΔP) of the cycle or iteration. $V_0$ may be measured or inferred, specific to this cycle or iteration, and may be set equal to the maximum displacement volume of the cycle or iteration. For any cycle or iteration, any observed variation between successive maximum values of pressure and volume are inconsequential; for instance if a successive cycle only achieves a maximum pressure of 60% of $P_0$ the previous cycle, the graph is renormalized such that $P_0$ may again be set equal to the maximum pressure of the cycle. If a first cycle attains a maximum pressure of 100 Pa, then $P_0$ is assigned the value of 100 Pa for that first cycle; if a second cycle attains a maximum pressure of 60 Pa, then $P_0$ is assigned the value of 60 Pa for that second cycle. Measurement of the time constant (t) for a system and fluid is comprises an embodiment of time domain viscometry. Time domain viscometry returns accurate results irrespective of the: maximum or minimum values of pressure, flow and volume of a cycle because the time constant (t) may generally be measured at any arbitrary value of pressure, flow and volume rate such as may be provided by ancillary system components. Similarly, it makes no difference if a cycle or iteration is terminated after a duration of 10τ, 1τ or 0.5τ; measurement of t is generally insensitive to variation in initial and final volumes, flow rates and pressures, including variation between successive cycles.

The quantitative relationship between pressure, flow rate, volume and viscosity is presented and dimensionally confirmed. Time domain viscometry comprises methods and systems to measure pressure in dimensions of $[FL^{-2}]$ and in representative units such as Pa or psi, and transform that pressure data into a measurement of dynamic viscosity in dimensions of $[FL^{-2}T]$ and in representative units including Pa or cP and/or a measurement of flow rate in dimensions of $[L^3T^{-1}]$ in representative units including $m^3/s$, cc/second, liters/minute, etc. Two properties of the exponential function include that: (1) differentiation of an exponential function yields that same exponential function divided by a constant (as shown herein previously) and (2) integration of an exponential function yields that same exponential function multiplied by a constant. In both cases, that constant is the negative of the time constant ($-\tau$).

In FIG. 5*c*, saline pressure trace 550 exhibits an approximate slope of $m\approx-1$ at $t=0$, $m\approx-0.6$ at $t\approx0.7$ and $m\approx-0.4$ at $t\approx1$; this is a result of eq. 11 where the slope (at any point) is equal to the value of the function at that point, divided by the negative of the time constant. The same results may be obtained from the other pressure traces (blood and thrombus) shown in FIG. 5*c*; each graph may be normalized (in time) to each time constant ($\tau_{blood}\approx4$ and $\tau_{thrombus}\approx30$).

The area under the curve bounded by the ordinate axis (P, Q, V), the time axis and saline slope line 515 may be visually observed to be 0.5 in FIG. 5*c*, using the area equation for a triangle: A=½bh, where b and h are the base and height of the triangle; b and h have unit values in FIG. 5*c*. The area under curve saline pressure trace 550 is of interest because it represents the integral of pressure over time, which has dimensions of $[FL^{-2}T]$, identical to the dimensions of viscosity as may be expressed in the units of Pa·s. Therefore, integrating measured pressure over time provides a plausible candidate for the measurement of viscosity, given the dimensional consistency. The area under saline pressure trace 550 is given in eq. 17:

$$\int_0^\infty P dt = P_0 \int_0^\infty e^{-\frac{t}{\tau}} dt = -P_0 \tau e^{-\frac{t}{\tau}} \Big|_0^\infty = \tau P_0 \qquad \text{Eq. 17}$$

The area under normalized curve saline pressure trace 550 is also equal to the time constant t, previously identified as viscosity; $P_0$ is normalized to unity with each iteration or cycle. FIG. 5*c* shows initial differential pressure ($P_0$) to be normalized to 1, and the time axis is normalized to $\tau_{saline}$. $\tau_{saline}$ is generally a strong function of the system configuration, for instance a very compliant (soft) compliance chamber coupled with a small diameter catheter may exhibit a large value of $\tau_{saline}$ because of the frictional resistance of a small diameter conduit coupled with a small differential pressure of a soft compliance chamber. In contrast a stiff compliance chamber coupled with a large diameter catheter may exhibit a small value of $\tau_{saline}$. Therefore measurement of $\tau_{saline}$ is system-specific given the variability of compliance chamber stiffness, catheter diameter and length, displacement volume, etc. Anticipated variability in manufactured components (such as the diameter, length, surface roughness, burrs, etc. of a catheter or the dimensional or hardness variability of peristaltic pump tubing, etc.) also illustrate the necessity and/or prudence of measuring $\tau_{saline}$ specific to the pump, tubing, catheter, control system algorithm, etc. utilized for time domain viscometry. Initial calibration measuring $\tau_{saline}$ (or other reference liquid, e.g., water, blood, oil, paint, etc.) is generally included in preferred embodiments of the present invention. Thrombectomy systems and metering pumps generally incorporate some form of "priming" to displace air with liquid; the act of "priming" a pump or thrombectomy system with saline may provide the necessary and sufficient data to complete measurement of $\tau_{saline}$ for the system (at the time of the procedure and upon the equipment utilized in the procedure). The selection of saline as a reference fluid for normalization and viscometric calibration may be representative of thrombectomy systems; other applications may select other reference fluids including, but not limited to: water, alcohol, oil, paint, blood, etc.

Exponential functions generally possess a property of utility in time domain viscometry: the reciprocal of the initial slope (the time constant) is equal to the area under the (pressure, flow or volume) curve (slopes are shown negative in FIG. 5*c*); conversely the area under the curve is equal to reciprocal of the time constant (ignoring sign convention). Determining a measurement of the area under a curve such as saline pressure trace 550 is explored subsequently; the utility of the above stated property (relating the slope to the area under the curve) will be exploited because numerical differentiation is generally much more computationally and time efficient than numerical integration. The quantity to be determined may be area under a curve; however the mathematical and computational technique to quantify that area may be numerical differentiation (as opposed to numerical integration. Sign conventions may be overlooked herein for clarity of concept.

Both the initial slope (saline slope line 515) and the area under the curve are equal to the reciprocal of the time constant. The computational methods disclosed previously calculated the slopes; this example is computationally efficient by employing finite-difference techniques. Numerical integration of eq. 17 (to determine the time constant, t and thus, the viscosity, μ) is shown to be an equivalent method of measuring the time constant, however numerical integration may only be conducted upon definite integrals, in the case of numerical integration in time domain, data may need to be collected "to infinity" although approximately 5 time constants is shown to be adequately accurate for the functions under consideration (P, V and Q in a linear compliance chamber). Preferred embodiments of the invention employ numerical differentiation of pressure (flow or volume) rather than numerical integration of pressure; the results are identical, but differentiation is more computationally and time efficient. Numerical integration may be performed upon definite integrals using techniques including: Simpson's rule, trapezoid rule, quadrature, etc.; in embodiments of the present invention, establishing practical limits of integration is problematic because of the time required to collect adequate data.

Measurement of viscosity may be accomplished by the embodiments and methods of the present invention and by a definition of viscosity which includes the time integral of pressure, which has been experimentally and dimensionally confirmed. The next problem to be solved is calculation of flow rate which may be integrated to determine the volume delivered (for applications including metering pumps). The quantities $V_0$ and $Q_0$ are deterministic of the volume delivered with each complete cycle or iteration (when time exceeds $5\tau$ or approaches infinity); but there is no constraint that each cycle completes to equilibrium. To normalize many of the preceding examples, water or saline, at approximate viscosity $\mu\approx1$, may be used as a reference or calibration fluid. To determine the volumetric flow rate, a reference volumetric standard is required. One method may be to decrease the pressure in compliance chamber 900 to a reference pressure $P_0$ and measure the volume of liquid displaced, this value is $V_0$. A data set comprising reference $P_0$ and $V_0$ may be used to calibrate the system to measure flow in engineering units, the ratio $P_0/V_0$ may be used as a (ratiometric) calibration constant for subsequent volumetric calculations. An ideal compliance chamber 900, exhibiting linear response, may require only a single calibration constant $P_0/V_0$; non-linear systems may require additional calibration data at different values of $P_0$. Referring to FIG. 5*c*, $P=P_0$ and $V=V_0$ at time t=0; $V_0$ may be known by calibration constant $P_0/V_0$ and all ordinate values are normalized to 1. Eq. 18 (for volume) is provided by analogy with eq. 11 (for pressure).

$$V(t) \approx V_0 e^{-t/T};\ \frac{V\prime}{V} \approx \frac{-1}{T};\ V' \approx -V\frac{1}{\tau} \quad \text{Eq. 18}$$

As with pressure, dV/dt (the flow rate, Q) may be calculated at any point as 1/τ multiplied the value of V at that point, because the slope $V'=-V/\tau$. For example, at t=τ, the flow rate (Q) is approximately equal to $0.368Q_0$. Numerical approximation of dV/dt, evaluated at $V=V_0$ and t=0, may be equal to the slope of saline slope line 515 and thereby the proportional to the rate of volumetric change may be determined. Regardless of the viscosity of the fluid sampled (e.g., water, blood, thrombus, oil, paint, etc.) sampled, the measurement of dV/dt, evaluated at $V=V_0$ and t=0 (or another arbitrary time after t=0) may be the reciprocal of the time constant for that fluid (e.g., water, blood, thrombus, oil, paint, etc.). The ratio of measured time constants for a plurality of fluids is purported herein to be the ratio of the viscosities of the fluids. Measurement of one or more fluids, acting as calibration constants, possessing a known viscosity in engineering units (e.g., 1 cP (saline), 4 cP (blood), Pas, Ib·s/ft$^2$, etc.) may enable quantification of viscosity of any unknown fluid to be quantified in those (or any other) engineering units.

At time t=τ, the volume V of compliance chamber 900 is approximately equal to $0.368V_0$. For a cycle that began at $P_0$ and $V_0$ and ends one time constant, τ, later, $P=0.368P_0$ and $V=0.368V_0$; the volume displaced during this cycle is approximately $0.632V_0$ and with average flow rate of $0.632V_0/(\tau_{seconds})$. Extending the cycle to 5 time constants, the average flow rate is approximately $V_0/(5\tau$ seconds) and the (time integral of or) total flow is the displacement volume $V_0$. For any cycle not reaching approximately 5τ duration, only a portion of displacement volume (V) is transferred. Eq. 19 provides the volume displaced for a cycle of kτ duration, where k is a cycle of arbitrary duration for example purposes.

$$\int_0^{k\tau} Qdt = Q_0 \int_0^{k\tau} e^{-\frac{t}{\tau}} dt = -Q_0 \tau e^{-\frac{t}{\tau}} \Big|_0^{k\tau} = \tau Q_0 \left(1 - e^{-k}\right) \quad \text{Eq. 19}$$

While eq. 19 has the requisite dimensions of volume, implementation of such a computational technique may evaluate $e^{-k}$ with each cycle. At time kτ, $P \approx P_{k\tau}$, which may be measured as the minimum pressure in the cycle, both the minimum pressure and the time of the occurrence may need to be measured to implement the integral approach of eq. 19. Simultaneously with a minimum pressure at time kτ, $V \approx V_{k\tau}$, (this volume is not easily measured) therefore the value of $V_{k\tau}$ may be inferred in preferred embodiments. As a first example, if measured pressure $P_{k\tau} \approx 0.368P_0$ then inferred value $V_{k\tau} \approx (1-0.368)$ or $0.632V_0$; this event may occur at approximately tot. Similarly, if the measured pressure $P_{k\tau} \approx 0.15P_0$ then inferred value $V_{k\tau} \approx 0.85V_0$; this event may occur at approximately t≈2τ. The determination of volume displaced with any cycle may be given by eq. 20.

$$V_{cycle} = V_0 \left(1 - P_{min}/P_0\right) \quad \text{Eq. 20}$$

Figure 14:
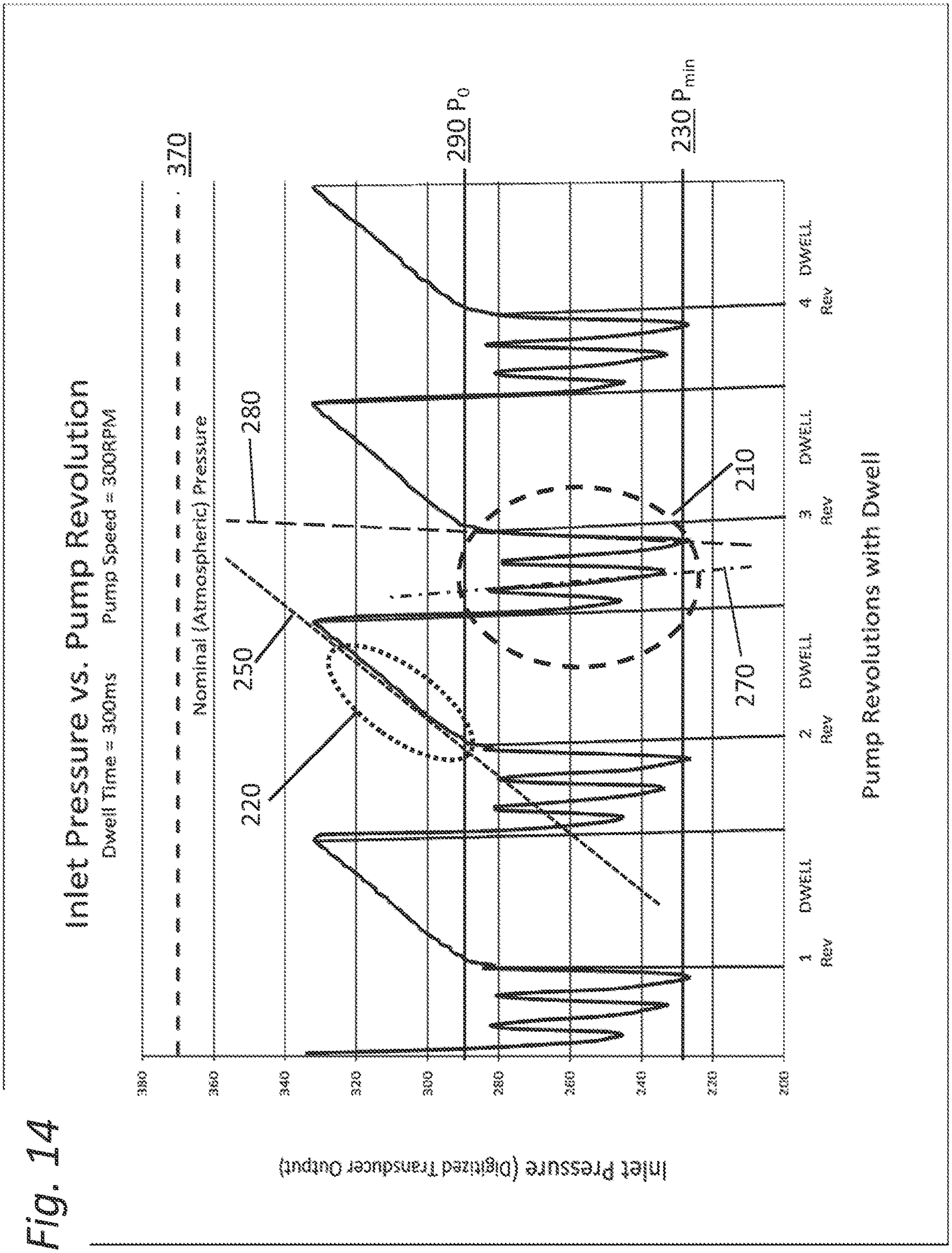
FIG. 14 shows a pressure vs pump revolution pressure trace for water.
Figure 15A:
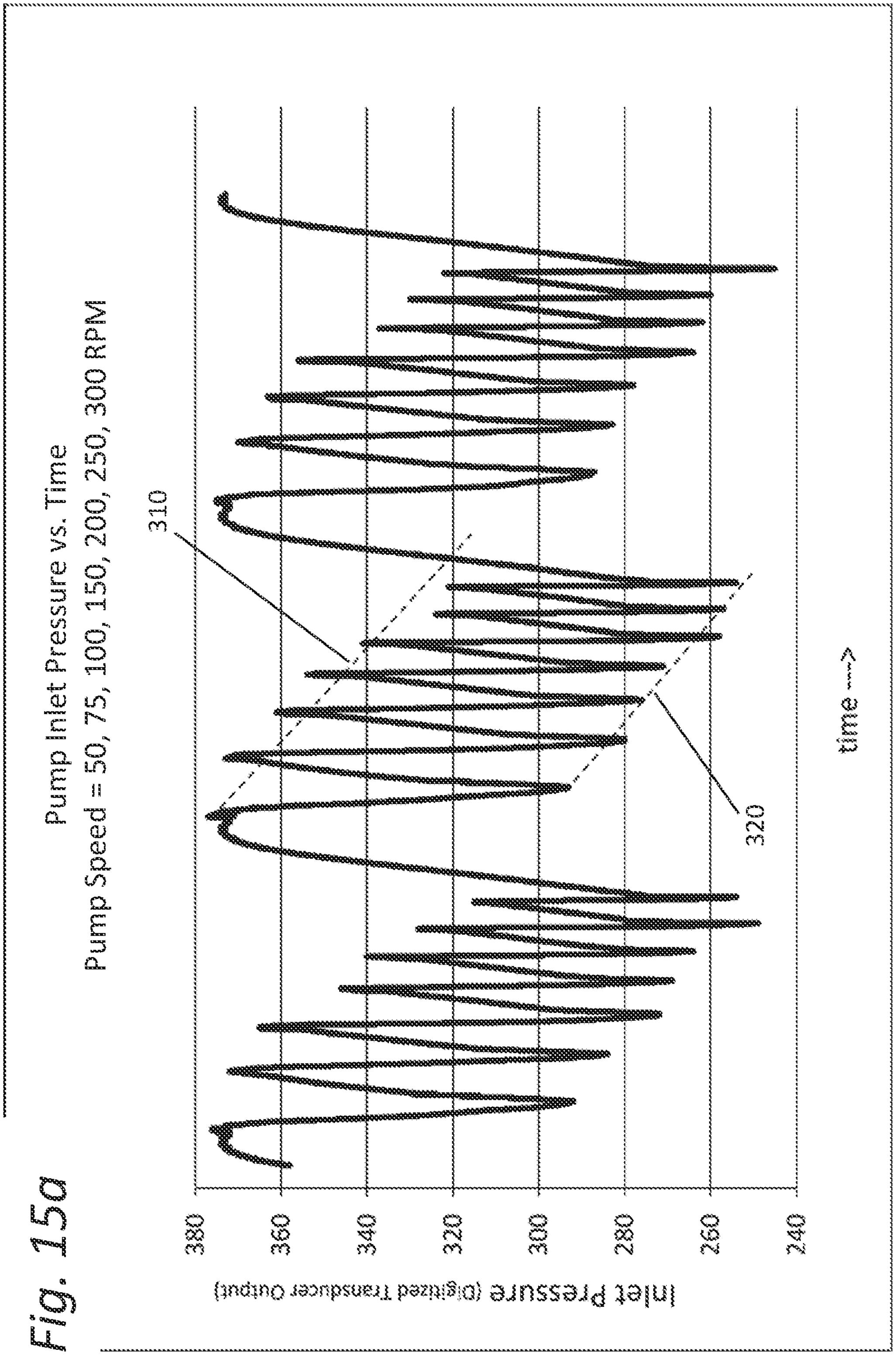
FIG. 15*a* shows a pressure vs time pressure trace (for water) wherein rotor 125 is rotated ⅓ revolution at 7 different speeds. One third revolution produces a single pressure pulse at each rotational speed.
Figure 15B:
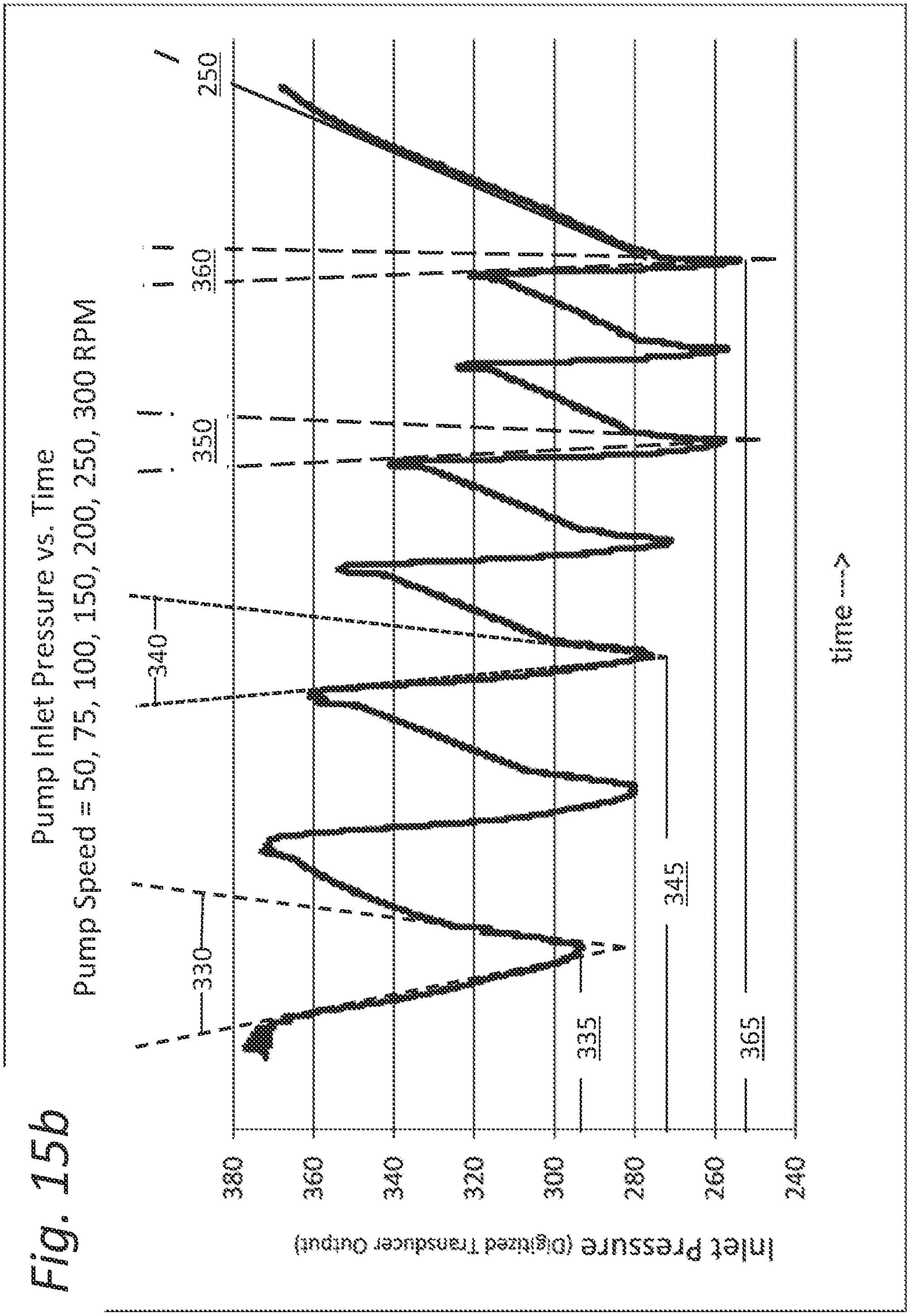
FIG. 15*b* shows an enlarged view of the data of FIG. 15*a* wherein the angle of each "valley" is indicated 330, 340, 350 and 360 for 4 different rotational speeds.

Thus, with each cycle, the volume delivered is proportional to the change in pressure within that cycle. This may be computationally accomplished by measuring $P_{min}/P_0$ for each cycle, calculating $V_{cycle}$ and summing this value over a number of cycles. This may be computationally accomplished by detecting alternating values of the slope of the pressure trace. When the slope of a pressure trace goes from positive to negative, (as shown in FIG. 14, FIG. 15*a* and FIG. 15*b*) a local maximum pressure is identified; likewise then the slope of the pressure trace goes from negative to positive a local minimum pressure is identified. The difference between these two successive pressure extrema is the change in pressure ($P_0$ and $P_{min}$ are thus identified for any cycle). Eq. 19 and eq. 20 enable the measurement of flow by determining the displacement volume delivered with each cycle.

Eq. 18, eq. 19 and eq. 20 provide a dimensionally consistent methodology to calculate total flow and flow rate using pressure and time measurements in a generalized apparatus for time domain viscometry. Prior art in the thrombectomy field makes frequent reference to the measurement of, determination of, monitoring of, characterization of flow (rate) as an indicator of thrombus in a catheter, and prior art is generally limited descriptive terms and/or attribute data to describe flow. Eq. 18, eq. 19 and eq. 20 and related analyses are included herein to distinguish the present invention from prior art, using terminology consistent with prior art (e.g., flow, flow rate, volume, etc.). Eq. 18, eq. 19 and eq. 20 also introduce the extensive property length (and subsequently volume) into the set of dimensions; FIG. 5*c* is annotated with three ordinate scales (pressure, flow rate and volume), pressure is an intensive property while flow rate and volume are extensive properties. FIG. 5*a* has the dimensionless ordinate ($P/P_0$) and abscissa ($t/\tau_{saline}$) which did not affect calculation of the dimensioned quantities such as the time constant (having the dimensions of time). FIG. 5*c* also depicts dimensionless domain and range (abscissa and ordinate, x- and y-axes) however dimensioned quantities are derived therefrom (e.g., viscosity, flow rate and dispensed volume). Herein, quantities (e.g., P, Q, V, μ, $\tau_{saline}$, etc.) may take dimensionless form and act as arbitrary constants (in some cases, scaling factors). To substantiate dimensional analysis of FIG. 5*c*, the ordinate dimensions are P $[FL^{-2}]$, V $[L^3]$ and Q $[L^3T^{-1}]$ and the abscissa dimension is time [T] after normalization by dimensionless numerical values of $P_0$, $V_0$, $Q_0$ and τ. In general, calculations involving extensive properties may require additional arbitrary constants (scaling factors) in contrast to intensive properties which are generally not sensitive to changes in scale.

For a linear compliance chamber which exhibits a pressure decay as expressed in eq. 11 and volume decay as expressed in eq. 18, (and overlooking any sign convention for convenience), the present invention utilizes the properties expressed in eq. 21 and eq. 22. The corresponding equations for flow (as a function of time) are given in eq. 23 for a complete cycle to infinite time.

$$P' = |P/\tau|;\ \int_0^{\infty} Pdt = \tau P_0 (\text{units of viscosity}) \quad \text{Eq. 21}$$

-continued $$V' = |V/\tau| \text{ (units of flow)}; \int_0^\infty V dt = \tau V_0 \qquad \text{Eq. 22}$$

$$Q' = |Q/\tau|; \int_0^\infty Q dt = \tau Q_0 \text{(units of volume)} \qquad \text{Eq. 23}$$

The differential forms of eq. 21, eq. 22 and eq. 23 assert that a time derivative of quantities P, V or Q is equal to the value of that quantity divided by the time constant; and the time integral forms of eq. 21, eq. 22 and eq. 23 assert that integration of quantities P, V or Q is equal to the initial value of that quantity multiplied by the time constant (neglecting any sign conventions). One objective of time domain viscometry is to measure the pressure (of a fluid) in dimensions of $[FL^{-2}]$ in units including: $m^3/s$, cc/second, liters per minute, etc. and transform the pressure measurement into a measurement of dynamic viscosity in dimensions of $[FL^{-2}T]$ and in units including: Pas, cP, etc. This may be accomplished by integration, as shown in eq. 21 which yields the parameter of interest, the time constant, τ; once t is determined, then the viscosity may be determined. Embodiments of numerical integration (of definite integrals) may require data collection over a period of time exceeding approximately 5 time constants, t, in duration. But since the same time constant, τ, may be determined by numerical differentiation, which is time and computationally efficient, preferred embodiments utilize numerical differentiation by finding the slope at the initial pressure, $P_0$; $V_0$ and/or $Q_0$ may be similarly analyzed depending upon the embodiment and application.

Preferred embodiments of the present invention employ the measurement and calculations upon intensive properties including pressure and viscosity. This may allow any scaling factors to be introduced subsequent to the relevant calculations of time domain viscometry. Nevertheless, measurement data of an intensive property (e.g., viscosity, etc.) may be transformed to measurement data of extensive properties (e.g., flow rate, total flow, etc.) as required by the application (e.g., metering pumps, etc.). For metering pumps, it is experimentally determined that flow rate and/or delivery volume are diminished by approximately the ratio of measured viscosities; this is a first-order approximation and higher-order approximations may be developed in conjunction with experimentation to enable accurate measurements of flow rate and delivery volume.

Suction thrombectomy systems may be classified into at least two categories: gas-over-liquid/solid phase and liquid phase, the former being depicted and described heretofore. In the electric-hydraulic analogy, a gas-over-liquid phase system is similar to a battery and a switch, with either full vacuum or no vacuum applied. The analogous electric circuits were used as examples to facilitate derivation and solution of relevant equations. Embodiments depicted heretofore feature structures and systems, such as a vacuum pump (not shown) and vacuum reservoir 10, as a source of differential pressure; such systems are characterized by an evacuated reservoir with a phase interface between the liquid/solid (e.g, blood, thrombus, vessel wall, etc.) and gas/vapor (e.g., air, water vapor, etc.) phases. A typical thrombectomy vacuum reservoir may have volume of approximately 1 liter (approximate range of 100 cc to 3 liters) the pressure of which is determined by the amount (mass, number of moles or molecules) of vapor/gas present within the reservoir. Evacuating such a reservoir (to attain aspiration vacuum) requires time to transfer mass (gas/vapor) on a time scale of approximately 1 second to 60 seconds or more. Because of the time required to fill and evacuate an appropriately-sized reservoir of gas/vapor, suction thrombectomy systems are generally incapable of modulating, or continuously varying, the vacuum level. Prior art (and the embodiments of FIG. 1*a* through FIG. 4*a*), generally utilizes an on/off valve (e.g., pinch valve, solenoid valve, spool valve, poppet valve, etc.) to create either a "full vacuum" or "no vacuum" state with no intermediate state available. The suction thrombectomy embodiments depicted heretofore serve two distinct purposes: (1) enable persons skilled in the art to implement the present invention to new or existing gas-over-liquid/solid phase suction thrombectomy systems, and (2) define the terminology and illustrate the concepts disclosed in forthcoming embodiments.

Example embodiments of liquid-phase suction thrombectomy systems may comprise liquid pumps of types including: peristaltic pumps, diaphragm pumps, gear pumps, centrifugal pumps, turbine pumps, vane pumps, etc. FIG. 10*a* shows an oblique view of an embodiment of the present invention which comprises liquid pump 850 as a source of differential pressure for aspiration in the form of reduced liquid pressure at the pump inlet (in contrast to vacuum reservoir 10). Liquid pump 850 may be a positive displacement pump which prevents flow through the pump when the pump is not operating; thus, liquid pump 850 may thereby also act as a valve. Fluid may flow proximally through catheter 40, through open valve 855 and into manifold 860; wherein pressure sensor 70, liquid pump 850, and spring compliance chamber 865 are in fluid communication. Liquid pump 850 may pump and discharge fluid from manifold 860 to waste reservoir 870. Liquid pump 850 may be reversible and/or variable-speed and may be capable of generating vacuum approaching "full vacuum," boiling or cavitation pressure. Cavitation (or boiling) in a liquid-phase suction thrombectomy system represents the maximum attainable vacuum and may be desirable in order to rapidly aspirate thrombus or clear a clogged catheter 40. Herein, the term cavitation may be used to describe boiling phenomena wherein the ambient pressure is equal to or below the vapor pressure of a fluid. Pressure sensor 70 is depicted as a pressure gauge for illustration purposes; embodiments of pressure sensor 70 generally feature output data to system controller 600 (not shown).

A liquid-phase aspiration embodiment of compliance chamber 30, 900 assembly is shown in FIG. 10*a* as spring compliance chamber 865, (shown in cutaway/exploded view) which shows spring 875 and piston 880 which slidingly engages with the mating cylinder 885 (when assembled). The spring compliance chamber 865 embodiment may afford a linear pressure-volume relationship because a helical spring may be a linear component obeying Hooke's law, F=−kx; this embodiment may provide linear compliance similar to the linear capacitance of an ideal capacitor.

Figure 10B:
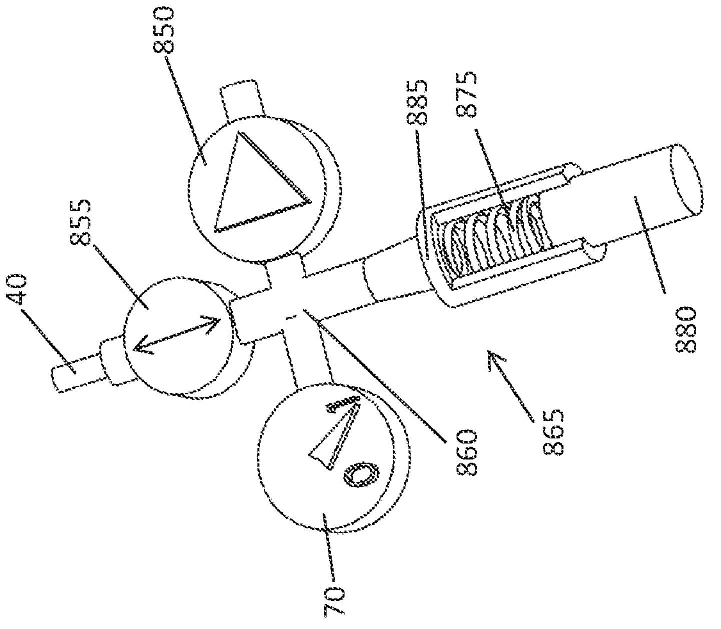
FIG. 10*b* shows the spring compliance chamber of FIG. 10*a* in assembled configuration. The cylinder is shown in cutaway view to afford view of the piston and spring at or near maximum volume.
Figure 10A:
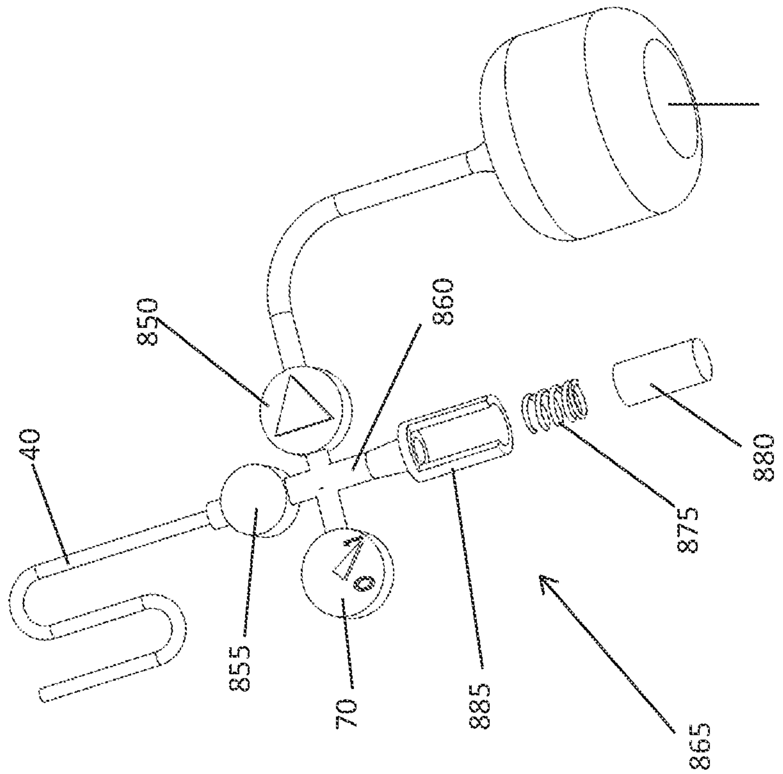
FIG. 10*a* shows an exploded/perspective view of an embodiment of spring compliance chamber. A liquid pump is shown as the source of aspiration.

FIG. 10*b* shows an oblique/cutaway view of spring compliance chamber 865 assembly in an assembled configuration, at or near maximum volume; pressure sensor 70 reads approximately 1 atmosphere on an absolute scale; local pressure, at the distal end of catheter 40, may be measured by pressure sensor 70. Valve 855 is shown in the open position. Liquid pump 850 is not running; the view of FIG. 10*b* is one of static equilibrium (neglecting variations in the local pressure). Cylinder 885 is shown in cutaway view to permit viewing of spring 875 and piston 880. FIG. 10*b* is analogous to FIG. 1*a* wherein $P1 \approx P_{local}$ (measured by pressure sensor 70) and compliance chamber 30 is at or near maximum volume, designated V1.

Figure 10D:
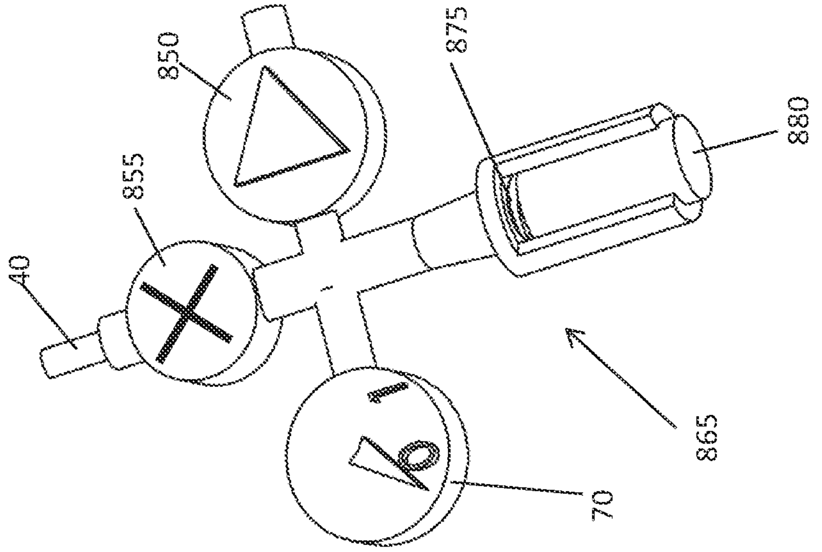
FIG. 10*d* shows the spring compliance chamber of FIG. 10*b* at or near minimum volume, and at or near minimum internal pressure.
Figure 10C:
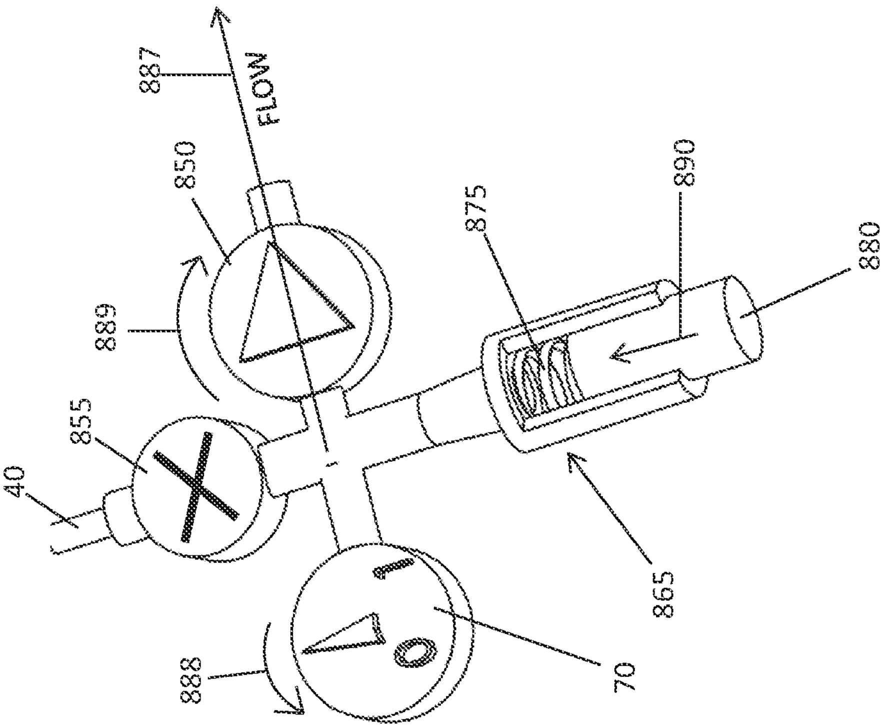
FIG. 10*c* shows the spring compliance chamber of FIG. 10*b* at an intermediate volume. The pressure is decreasing as the spring compliance chamber volume decreases.

FIG. 10*c* shows an oblique/cutaway view of spring compliance chamber 865 assembly wherein valve 855 is closed and liquid pump 850 is operating (pump operating 889) to drive fluid flow toward waste reservoir 870 (not shown) in flow direction 887; the fluid is transferred out of spring compliance chamber 865; piston 880 is moving in the piston movement 890 direction, spring 875 is being compressed. Pressure sensor 70 measures a decreasing pressure 888, shown to be approximately ½ atm (≈15 inHg vacuum). The configuration, action and flow depicted in FIG. 10*c* may be analogous to FIG. 2*a* wherein the volume of compliance chamber 30 is at an intermediate volume and decreasing in magnitude. In FIG. 10*c*, flow through catheter 40 is not permitted because valve 855 is closed. This is in contrast to FIG. 2*a* wherein aspirate flow exists through catheter 40. The configuration, motion and flow depicted in FIG. 10*c* acts to bias spring compliance chamber 865 such that subsequent opening of valve 855 may result in aspirate flow (from catheter 40) and into spring compliance chamber 865 in order that the flow and viscosity measurement aspects of the present invention may occur.

FIG. 10*d* shows an oblique/cutaway view of spring compliance chamber 865 assembly where valve 855 is closed; liquid pump 850 is shown to be stopped, liquid pump 850 may act as a closed valve while stopped. Flow through catheter 40 is prevented because valve 855 is closed. Static equilibrium may be established with pressure sensor 70 measuring pressure which is at or near minimum (at or near maximum vacuum). Piston 880 is at or near full engagement depth and spring 875 is at or near maximum compression. The configuration depicted in FIG. 10*d* may be analogous to FIG. 1*c* wherein compliance chamber 30 is shown to be at or near minimum volume, V3, and pressure P3 is at or near minimum.

Figure 10E:
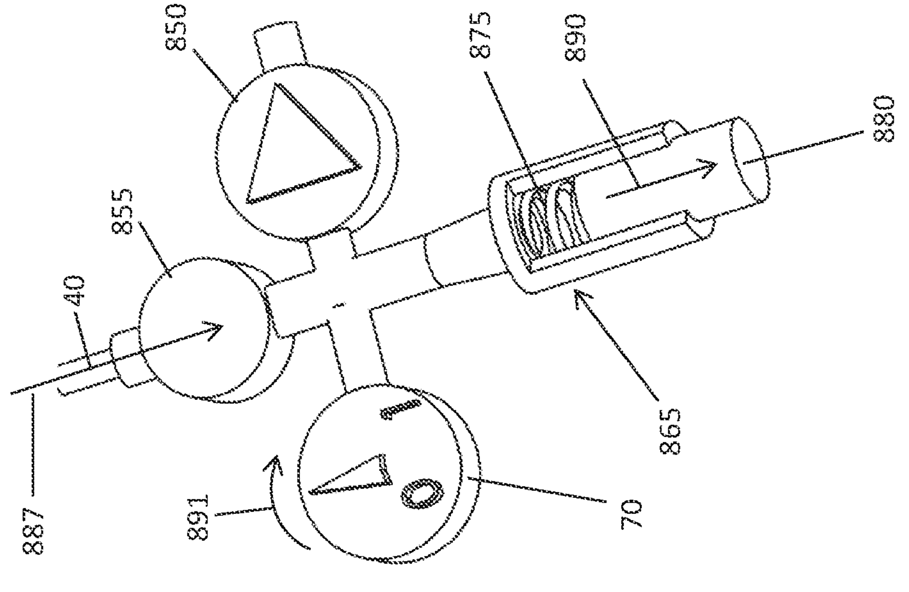
FIG. 10*e* shows the spring compliance chamber of FIG. 10*b* at an intermediate volume. The pressure is increasing as the spring compliance chamber volume increases.

FIG. 10*e* shows an oblique/cutaway view of spring compliance chamber 865 a short period of time after valve 855 is opened, permitting aspirate flow in flow direction 887 into spring compliance chamber 865. Liquid pump 850 is stopped and acts as a closed valve, preventing flow to waste reservoir 870 (not shown). Pressure sensor 70 is depicted to measure an increasing pressure 891, FIG. 10*e* shows instantaneous pressure to be approximately ½ atm (≈15 inHg vacuum). Aspirate (of unknown viscosity) flows from catheter 40, through open valve 855 and into spring compliance chamber 865; the time-domain viscometric calculations of the present invention may subsequently be executed. The viscosity of aspirate contained in catheter 40 may thereby be quantitatively determined, and an appropriate control system response may be executed.

Figure 11:
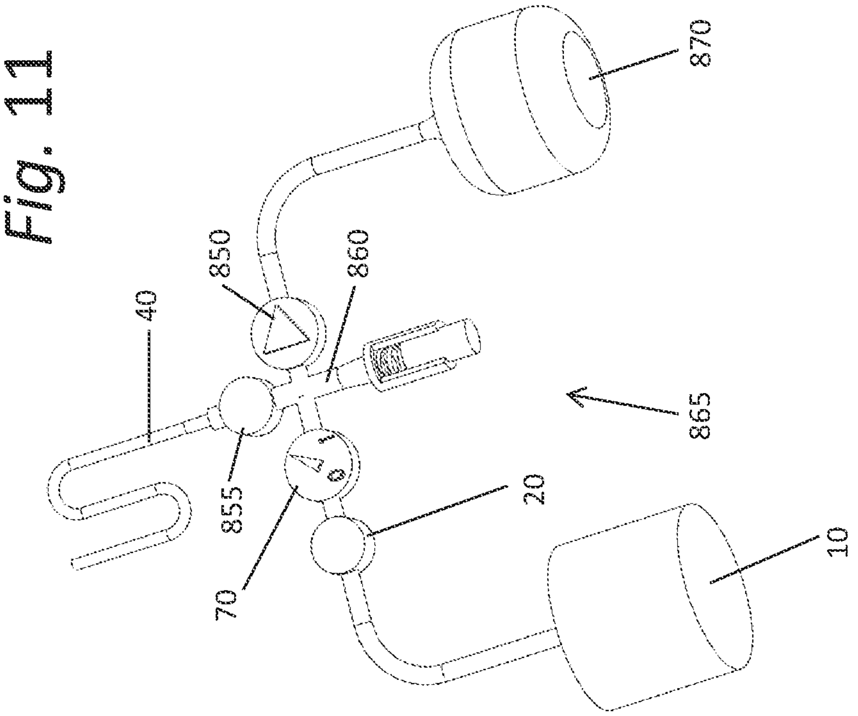
FIG. 11 shows a perspective view of a spring compliance chamber with both a liquid pump and a vacuum reservoir as alternate sources of aspiration.

FIG. 11 shows a perspective view of the embodiments of FIG. 10*a* through FIG. 10*e* with the incorporation of vacuum reservoir 10 and vacuum valve 20 in fluid communication with manifold 860. These additional components may increase the vacuum level available, because vacuum reservoir 10 may be operable at a greater vacuum (lower pressure) level than may be achievable by liquid pump 850. Liquid pump 850 may not be capable of achieving vacuum in excess of approximately 26inHg (vacuum), whereas vacuum reservoir 10 and associated (gas) vacuum pump may achieve a greater vacuum level. Maximum available vacuum may be necessary for efficient and effective aspiration of thrombus.

For any embodiment of a thrombectomy system of the present invention, the physical attributes of compliance chamber 30 may dictate the value of the saline time constant, $\tau_{saline}$. Compliance chambers 30 exhibiting greater volume displacement may take more time to empty or fill; this will result in an increase in $\tau_{saline}$ when compared to smaller displacement counterparts. Compliance chambers 30 exhibiting less rigid structures, components and materials may tend to decrease the value of $\tau_{saline}$ when compared to their more rigid counterparts. A preferred embodiment of compliance chamber 30 provides for a value of $\tau_{saline}$ in the range of 0.1 seconds to 20 seconds.

The preceding disclosures and figures have presented embodiments with combinations of: (1) two sources of differential pressure (liquid pump 850 and vacuum reservoir 10), (2) two embodiments of compliance chamber 30, 900 and spring compliance chamber 865. These disclosed embodiments rely on differential pressure to expand or contract the volume of the compliance chambers. The embodiments of FIG. 1*a* through FIG. 4*a* depict vacuum valve 20 to be physically located downstream of compliance chamber 30 (vacuum valve 20 is intermediate between compliance chamber 30 and vacuum reservoir 10). In these embodiments, vacuum valve 20 may alternatively be located between compliance chamber 30 and catheter 40, or upstream of compliance chamber 30; such a component arrangement provides a noteworthy difference: the presence or absence of flow through catheter 40 at the same time that compliance chamber 30 is being evacuated by fluid communication with vacuum reservoir 10. An objective of the improved thrombectomy system of the present invention is to minimize blood loss during the course of the thrombectomy procedure. As shown in FIG. 1*a* through FIG. 4*a*, aspirate may flow through catheter 40 concomitantly with the evacuation of compliance chamber 30. Conversely, the embodiments of FIG. 10*a* through FIG. 10*d* and FIG. 11 may not permit concomitant aspirate flow through catheter 40 during the time when spring compliance chamber 865 is undergoing volumetric change. The latter configurations and embodiments may isolate spring compliance chamber 865 from catheter 40 (during this time period, the “charging” period) such that total aspirate flow may be diminished during the course of the thrombectomy procedure. In FIG. 10*c* valve 855 is shown to be closed during a “charging” or “emptying” phase of spring compliance chamber 865; opening valve 855 during the charging phase may slow the charging phase (aspirate is concomitantly drawn from both catheter 40 and spring compliance chamber 865). The difference in the two configurations/embodiments may be termed non-isolating (FIG. 1*a* through FIG. 4*a*) or isolating (FIG. 10*a* through FIG. 10*d*); experimentation may be employed to determine the preferred location of valve(s) with respect to compliance chamber(s).

Figure 12B:
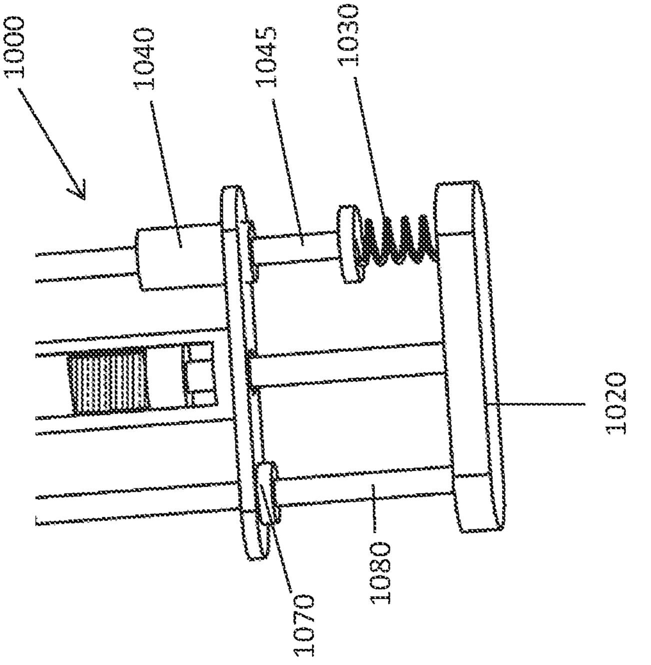
FIG. 12*b* shows a perspective view of a syringe compliance chamber. The linear actuator is shown elastically coupled to plunger by a spring.
Figure 12A:
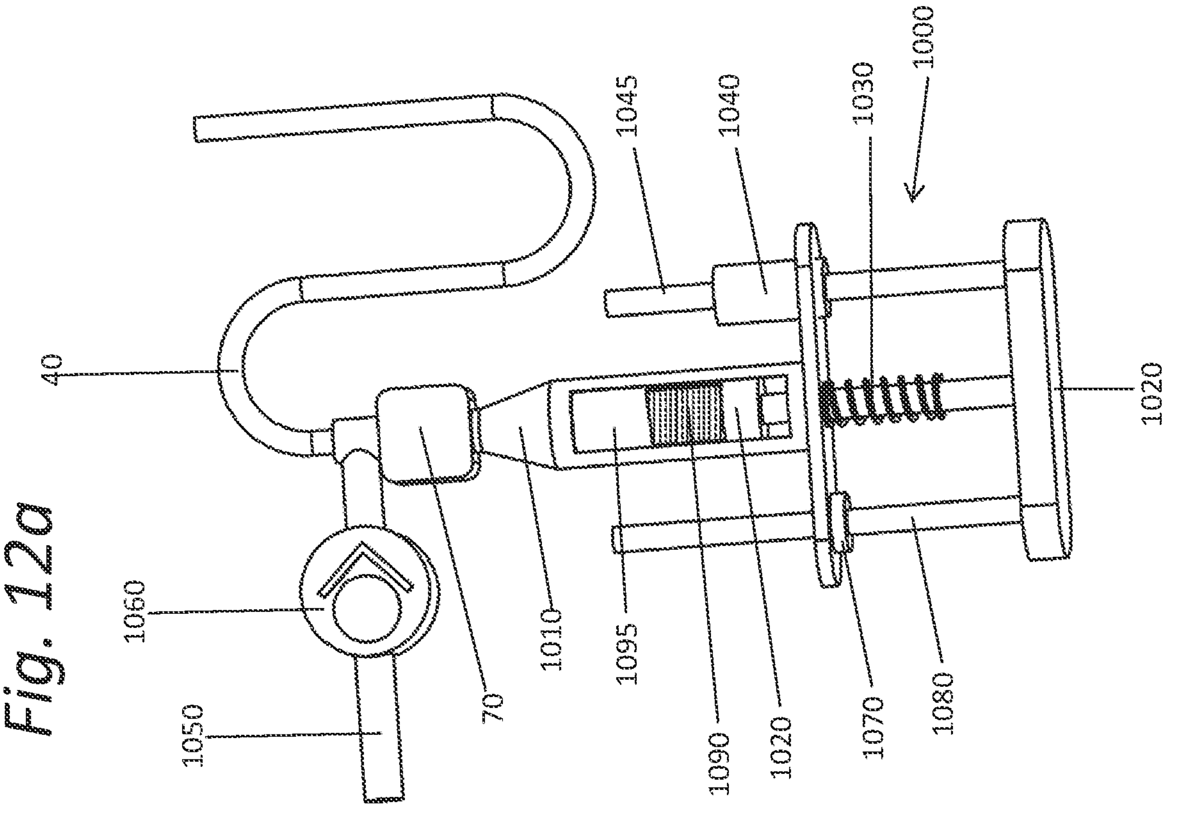
FIG. 12*a* shows a perspective view of a syringe compliance chamber. Two biasing means are shown: a spring (biasing the plunger against the barrel) and a linear actuator; a position linear encoder is shown to measure the plunger position and the syringe volume.

FIG. 12*a* shows a perspective view of an embodiment of a syringe compliance chamber 1000, which is shown to incorporate pressure sensor 70, check valve 1060, waste tube 1050 and catheter 40 in fluid communication with syringe barrel 1010. Waste tube 1050 may also be in fluid communication with a source of differential pressure, such as a liquid pump or a vacuum reservoir and valve assembly (not shown), or waste tube 1050 may discharge to any reservoir. At static equilibrium (no flow), pressure sensor 70 may measure pressure that is approximately equal to $P_{local}$. An increase in pressure within syringe barrel 1010 may result in fluid discharge through waste tube 1050 preferentially over outflow through catheter 40; waste tube 1050 is shown to be of larger diameter and shorter length than catheter 40, thus the waste tube is the preferred fluid pathway because of viscous effects present in catheter 40. Plunger 1020 is shown to have two forcing means: spring 1030 and linear actuator 1040. Spring 1030 may act similarly to spring 875 of FIG. 10*a* through FIG. 10*d*, thus providing a linear spring compliance chamber. Linear actuator 1040 may act to force linear actuator rod 1045 and thus exert force on plunger 1020; this force may be compressive (extending plunger 1020) or tensile (retracting plunger 1020). Linear actuator rod 1045 is shown in FIG. 12*a* to be rigidly coupled to plunger 1020. Linear encoder 1070 is shown to measure the position of plunger 1020 by means of linear encoder rod 1080. The time derivative of linear encoder 1070 position (the plunger velocity/speed) may be used to accurately measure the flow rate by eq. 24:

$$\text{Flow} = \text{Plunger Area} * \text{Plunger velocity} \quad \text{Eq. 24}$$

Thus, a further aspect of the present invention is the ability to directly measure aspirate flow through catheter 40. The functions of linear encoder 1070, linear actuator 1040 and spring 1030 may be combined into fewer than 3 units; the 3 units are shown to be discreet in FIG. 12*a* for clarity.

FIG. 12*a* shows both liquid 1090 and vapor 1095 contained within syringe barrel 1010, this is a special case which may be achieved by the extension of plunger 1020 which thereby decreases the pressure within syringe barrel 1010. If the extension of plunger 1020 is sufficiently rapid, viscous effects of aspirate flow within catheter 40 may prevent adequate aspirate flow rate to maintain the liquid phase within syringe barrel 1010. At liquid-vapor equilibrium the vapor 1095 contents of syringe barrel 1010 may be approximately the vapor pressure of blood at 37° C. (46 mmHg, 6.1 kPa). However the rapid extension of plunger 1020 may create non-equilibrium conditions such that the pressure of vapor 1095 may be less than the liquid-vapor equilibrium pressure of approximately 46 mmHg or 6.1 kPa, or approximately 28.2 inHg vacuum. Embodiments such as depicted in FIG. 12*a* and FIG. 12*b* may thereby achieve a maximum attainable vacuum; maximum attainable vacuum may be beneficial in certain thrombectomy operating modes including aspiration, clot or clog clearing.

Syringe compliance chamber 1000 may thereby achieve the maximum attainable vacuum that may be limited by the principles of chemistry and physics in a compact, easily-sterilized package which may be disposable. A suction thrombectomy system may achieve maximum procedure efficiency and efficacy by employing the maximum attainable vacuum (which may exceed approximately 28.2 inHg) at instances when clinical data indicate the need for maximum attainable vacuum. During periods of the procedure, smaller vacuum levels (greater pressure) may be preferred to minimize blood loss while measuring the viscosity of the aspirate for thrombus, clot or clogs. The embodiment of FIG. 12*a* may be capable of generating any achievable level of vacuum (or pressure) by means of linear actuator 1040, concomitant data collected from pressure sensor 70 may be employed to provide closed-loop feedback as input determine the position, velocity, acceleration or force to be applied to plunger 1020 under system control. Vapor 1095 may also develop in cases involving the contents of catheter 40 being clogged or very viscous; if there is little or no flow through catheter 40 then vapor may develop within barrel 1010. Vapor may also develop within catheter 40, this may be an effective approach to clearing viscous aspirate, clot or clog.

FIG. 12*b* shows a perspective view of an alternate embodiment of syringe compliance chamber 1000, wherein linear actuator rod 1045 is coupled to plunger 1040 by means of spring 1030. During a thrombectomy procedure, linear actuator 1040 may apply a force to linear actuator rod 1045 such that spring 1030 may become compressed (or extended). An advantage of the embodiment of FIG. 12*b* is that spring 1030 may be compressed rapidly by the force supplied by linear actuator rod 1045; this is in contrast to pressure force(s) employed by the prior embodiments. At instances during a thrombectomy procedure, viscosity and flow may be measured without the requiring the time delay associated with the aforementioned charging phase by executing a finite displacement of linear actuator rod 1045. This finite displacement may bias spring 1030 such that a differential pressure is created within syringe compliance chamber 1000. Preferred embodiments may comprise glass syringes because glass syringes generally exhibit less sliding friction than plastic syringes.

Embodiments of the syringe compliance chamber depict what may be an off-the-shelf syringe with a standard interface, such as a Luer-lock fitting. A Luer-lock fitting may not be appropriate because the fluid pathway may be approximately 0.080" or about 6Fr. A syringe fitting with a larger lumen may be advantageous because of the anticipated aspirate which may contain thrombus (proteinaceous and/or fatty solids) which may pass through the syringe compliance chamber fitting. Any such restriction (small passageways) for aspirate flow into and/or out of the syringe compliance chamber may cause viscous losses in the flowing aspirate which may degrade the data collected for time-domain viscometry, aspiration or other purposes in the improved thrombectomy system.

FIG. 9*a* through FIG. 9*f* show compliance chamber 900 as prior-art shown as a generalized reservoir constructed of material with elastic properties. Compliance chambers may comprise elastic reservoirs and may be constructed of materials including, but not limited to: rubbers (buna, silicone, neoprene, nitrile, EPDM, butyl, etc.), plastics (vinyl, PE, PP, PVC, PU, etc.), polymers, etc. Non-rigid tubing comprised of elastic materials may act as a compliance chamber; FIG. 9*a* through FIG. 9*f* depict a length of non-rigid, variable-diameter tubing acting as a compliance chamber. FIG. 10*a* through FIG. 10*e* and FIG. 11 show spring compliance chamber 865 which employs spring 875 as an elastic component permitting the motion of rigid bodies. FIG. 12*a* and FIG. 12*b* show spring 1030 as a biasing element bearing upon plunger 1020. Springs may be made of metals including: spring steel, stainless steel, nitinol, BeCu, music wire, alloy steels, etc. Compliance chambers are non-isovolumetric components which may be components of a thrombectomy system.

Certain disclosed embodiments (e.g., FIG. 10*a* through FIG. 12*b*) depict sources of differential pressure capable of providing pressure (in addition to vacuum) to catheter 40; pressurizing catheter 40 to a pressure exceeding the local pressure may cause reverse or negative aspiration such that outflow may exist from the distal end of catheter 40. Pressurizing catheter 40 may act to dislodge clogs; alternating sequences of vacuum and pressure may be employed to effectively dislodge and aspirate clogs or aspirate of very high measured viscosity. These alternating sequences may continuously or discreetly employ positive, negative and neutral aspiration as effective thrombectomy operating modes to aspirate clogs or high-viscosity aspirate more efficiently and expeditiously. The present invention includes apparatuses operable to intermittently measure aspirate viscosity, including within the alternating sequences of vacuum and pressure. Prior art may anticipate alternating sequences of vacuum and pressure (perhaps in pre-determined sequences); aspects of the present invention permit intermittent viscometry to be performed to assess the effectiveness of the pre-determined sequences.

A novel aspect of preferred embodiments of the present invention and time-domain viscometry is a 3-step process comprising (1) a charging step wherein differential pressure (or force) causes elastic deformation of components comprising a conduit, (2) a discharging and/or measurement step, wherein the deformed element is unconstrained (of pressure or external contact forces) and pressure decay data are successively collected with respect to time and (3) a calculation step, wherein the pressure decay data are analyzed by time-domain differential viscometry. In some embodiments, the calculation step comprises converting the data units (pressure and time) to engineering units, e.g., viscosity, flow rate, etc. In prior art, the data units (pressure and differential pressure) are compared to stored reference values which may comprise an array of arbitrary constants; the outcome of such conditional statements may comprise attribute data [IF (value exceeds a threshold) THEN (alert the operator)]. The present invention also invokes arbitrary constants (e.g., k, K, K*, etc.), however these may be measured and/or calculated at the start of (or at any time within) a single thrombectomy procedure, for example during calibration 801. Pressure vs time data may be collected upon saline and/or blood to determine any or all of the arbitrary constants which may be invoked in time-domain differential viscometry. This is in contrast to relevant prior art which may invoke arbitrary constants obtained from other sources (e.g., databases, stored arrays, artificial intelligence, historical data) which may have been collected under unknown conditions and upon reference fluids of unknown properties.

The foregoing disclosures and embodiments have been presented in the context of a thrombectomy system wherein an objective is to aspirate a minimum amount of blood concomitantly with a maximum amount of thrombus in a minimum amount of time. The referenced co-pending applications disclose the utilization of viscometry to quantitatively and qualitatively assess the "aspirate characteristic" in both quantitative (e.g., 1 cP, 4 cP, 200 cP, 1.5 cc/sec, etc.) and qualitative (e.g., saline, blood, thrombus, clot, clog, high-flow, etc.) terms. Viscometry in thrombectomy systems is disclosed to enable the first stated objective; and a viscometer which (1) utilizes a small volumetric sample size and (2) provides rapid quantitative results enabling the remaining two objectives.

Figure 13B:
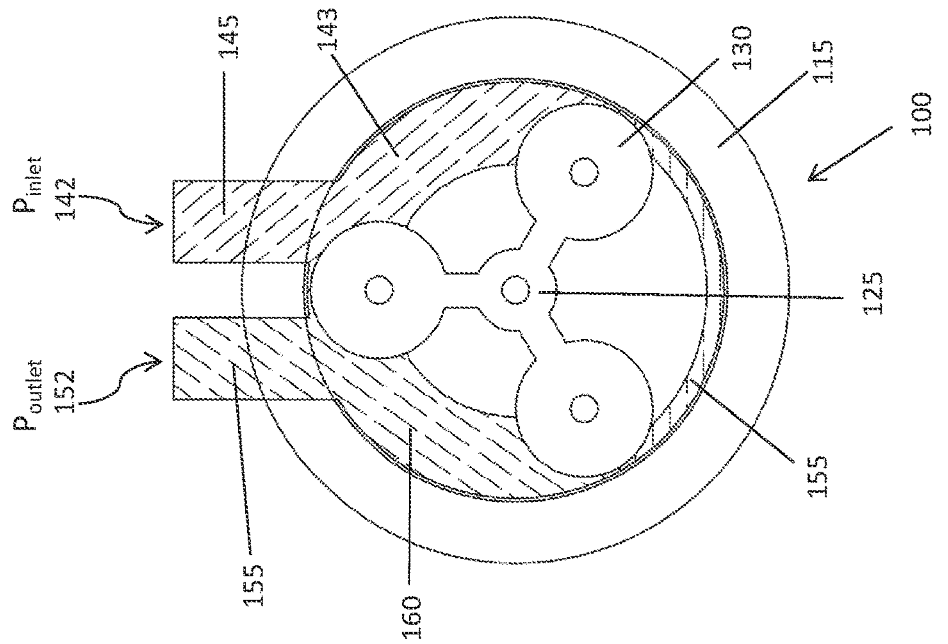
FIG. 13*b* shows the same peristaltic pump at a state wherein approximately zero differential pressure exists between inlet port and outlet port. The inlet tubing is shown in a nominal state.
Figure 13A:
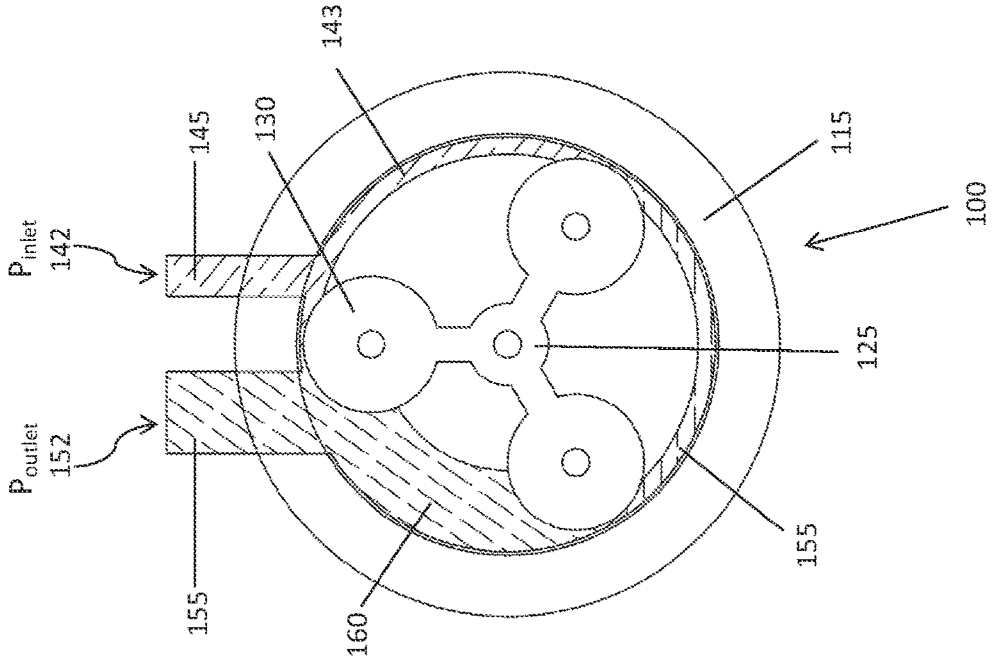
Prior Art Fig. 13a
FIG. 13*a* shows a peristaltic pump at a state wherein differential pressure between the inlet port and outlet port exists. The affected tubing is shown in a collapsed state. A peristaltic pump is prior art.
Figure 13C:
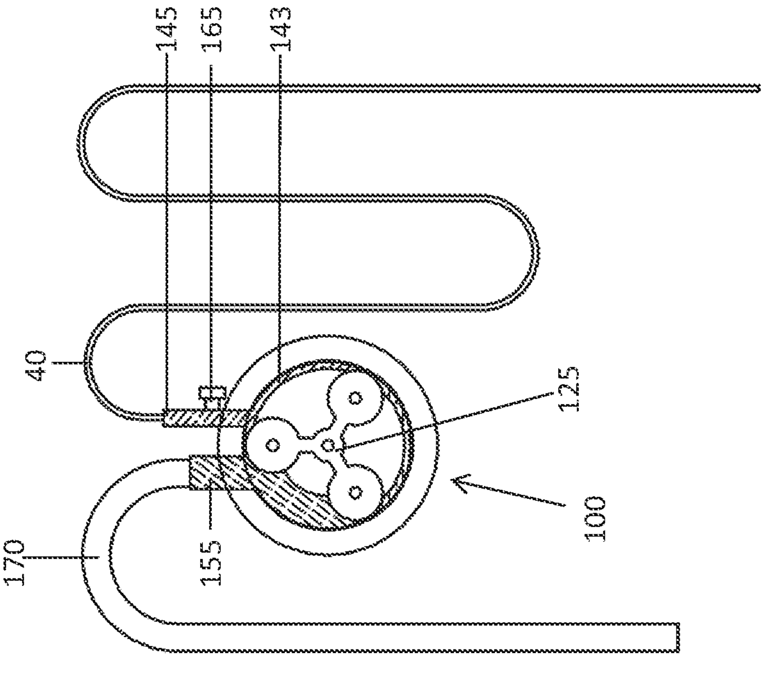
FIG. 13*c* shows a peristaltic pump 100 with a pressure transducer 165 and a catheter 40 shown attached. Prior art thrombectomy systems feature these components in this fluid communication pathway.

Peristaltic pump 100 of FIG. 13*a*, FIG. 13*b* and FIG. 13*c* are annotated as "Prior Art" due to ubiquity. FIG. 13*c* annotates the combination of pressure transducer 165 in fluid communication with peristaltic pump inlet port 145 as "Prior Art." FIG. 13*a* shows peristaltic pump 100, comprised of housing 110 and rotor 125 with 3 rollers 130. Rotor 125 is shown in a "home" position wherein any one of the 3 rollers 130 is intermediate between inlet port 145 and outlet port 155. Because rotor 125 is shown in a home position, inlet port 145 is in fluid communication with inlet cavity 143 and outlet port 155 is in fluid communication with outlet cavity 160; isolated cavity 155 is not in fluid communication with the other two cavities. Inlet cavity 143 is annotated as distinct from inlet port 145 despite that the two are in fluid communication as depicted in FIG. 13*a*, FIG. 13*b* and FIG. 13*c*; not shown is any occurrence wherein rotor 125 has rotated such that roller 130 interrupts fluid communication between inlet cavity 143 from inlet port 145. Outlet port 155 and outlet cavity 160 are approximately isobaric with $P_{outlet}$ 152; inlet port 145 and inlet cavity 143 are approximately isobaric with $P_{inlet}$ 142. Inlet cavity 143 and inlet port 145 are shown to be smaller in size/area than outlet cavity 160 and outlet port 155. $P_{inlet}$ may be inferred to be less than $P_{outlet}$ because the tubing is collapsed in both the inlet cavity 143 and the inlet port 145; isolated cavity 155 is shown to be approximately isobaric with inlet cavity 143 and inlet port 145. FIG. 13*a* may depict a "snapshot" of an operating pump with the rotor 125 rotating at a speed great enough that the tubing of inlet cavity 143 has not have sufficient time to relax toward the nominal dimension. FIG. 13*a* pictorially illustrates why peristaltic pumps deliver reduced volumetric flow at reduced inlet pressures, $P_{inlet}$ 142. FIG. 1*a* may also depict the configuration immediately after rotating rotor 125 is abruptly stopped, and before the tubing/volume of inlet cavity 143 has had sufficient time to expand toward nominal dimensions.

FIG. 13*b* shows peristaltic pump 100 at a time when inlet cavity 143 and/or inlet port 145 have had sufficient time to (fill and) expand toward nominal dimensions. Inlet cavity 143, inlet port 145, outlet cavity 160 and outlet port 155 are all shown to be at nominal dimension, and thus it may be inferred that inlet pressure 142 is now approximately equal to outlet pressure 152. Time domain viscometry may be implemented by analyzing the pressure trace of $P_{inlet}$ 142 with respect to time in the interim period between configuration FIG. 13*a* and FIG. 13*b*.

FIG. 13*c* shows peristaltic pump 100 with pressure transducer 165 and catheter 40 in fluid communication with inlet port 145; discharge 170 is in fluid communication with outlet port 155. Herein, catheter 40 is any generalized conduit with an aspect ratio (length: diameter) of greater than approximately 50. Catheter 40 is therefore "long" and "thin" such that viscous losses are appreciable; quantification of the viscous losses incurred throughout the length of the catheter may be a characteristic feature of time domain viscometry. Specifically, measuring the initial pressure and/or the time rate of change of pressure (the slope of the pressure trace) provide the present invention with the necessary data to quantitatively determine the viscosity of the fluid contained within catheter 40. Discharge 170 is shown to be of a shorter length and larger diameter than catheter 40 such that viscous losses through discharge 170 may be neglected in this example and in reducing the present invention to practice. FIG. 13*c* may be illustrative of a condition arising from abruptly stopping rotor 125 in a home position. The tubing comprising inlet cavity 143 may relax toward a nominal dimension as flow through catheter 40 supplies the required volume to fill the expanding inlet cavity 143. Flow through catheter 40 is generated by the differential pressure between inlet cavity 143 and the distal end of catheter 40. Immediately after rotor 125 is abruptly stopped, pressure within and volume of inlet cavity 143 are at or near minima (overlooking phenomena including shock, water hammer, valve noise, electrical noise, etc.). The pressure within and volume of inlet cavity 143 may subsequently increase in a generally monotonically increasing fashion for a portion of the measurement cycle; this pressure increase may be exponential, linear, logarithmic, etc. as examples. As the volume of inlet cavity 143 increases, flow through catheter 40 provides the requisite volume to fill inlet cavity 143. Therefore flow through catheter 40 will initially be at or near a maximum and generally decrease with time as the differential pressure (along catheter 40) decreases with time.

In the embodiments and context of the present invention, viscosity and flow are generally inversely proportional. Aspects of the present invention quantitatively analyze the time required for the configuration depicted in FIG. 13*a* to assume the configuration depicted in FIG. 2*b*. A fluid of greater viscosity will exhibit a lower flow rate; therefore the fluid of greater viscosity will require a longer period of time to refill inlet cavity 143 (than a fluid of lesser viscosity).

A time constant, τ, is used herein to mean any characteristic period of time required for a predetermined change in a system parameter such as differential pressure. For instance, a time constant may be measured by calculating the slope of the inlet pressure trace of $P_{inlet}$ 142 during the period of time that inlet cavity 143 refills toward nominal volume. This definition of time constant is not unique, because multiple time constants may be defined, derived or experimentally determined which may be comprised of: stopped slopes, running slopes, negative slopes, angles, pressure range and magnitude, etc. Regardless of how any particular time constant may be reasonably defined, it is a function of the fluid viscosity; in general, time constants of greater magnitude may be inferred to measure fluid viscosities of greater magnitude.

In a peristaltic pump embodiment of the present invention, a time constant is defined to be the inverse of the stopped (rotor) slope 250. A fluid of lower viscosity will exhibit rapid flow and a small time constant, τ; this is because inlet cavity 143 fills in a shorter amount of time. A fluid of higher viscosity will exhibit slower flow and a longer time constant, τ; this is because inlet cavity 143 requires a longer amount of time to fill with a more viscous fluid in catheter 40. Experimentally, (and with the chosen definitions for representative time constants), approximately 5τ is generally adequate time for inlet cavity 143 to refill and for the differential pressure to approximately equalize (approach zero) between inlet cavity 143 and the distal end of catheter 40. A time constant may be measured in a fraction of the time constant itself; for example, the determination of a 10 second time constant may be measured in less than approximately 0.4 s, because the initial slope of the pressure trace adequately defines the future differential pressure decay. The time required to determine a time constant is independent of the time constant itself, in the above example, it is immaterial if the time constant is 1 s, 10 s, or 1,000 s; a time constant measurement requires the same duration of approximately 0.4 s. With faster processors, data sampling rates and more efficient coding the time required for a time constant measurement can be reduced, optimization may bring the duration required to measure the time constant to be less than 0.1 s, or 100 ms.

The contents of catheter 40 are thereby analyzed for viscosity, however the contents of catheter 40 are not necessarily homogeneous; there may be stratifications, flow restrictions, partial or total occlusions, solid thrombus or clotted blood present in catheter 40. Any such inhomogeneity contained within catheter 40 will generally result in an increase in measured viscosity, as expected. Catheter 40 may be clogged or "corked;" this may result in a measured viscosity which is large; a clogged catheter may exhibit a pressure trace of zero slope which infers infinite viscosity. In applications including thrombectomy systems, detection of an occluded, clogged or corked catheter provides relevant and valuable data to the clinician and/or to any system controller such that unclogging counter-measures may be enacted, either under system or manual control. Some thrombectomy systems provide for the infusion of saline which mixes with blood; blood which has been diluted with saline may exhibit a lesser viscosity than whole blood. Blood has an approximate viscosity of 4 cP, saline has an approximate viscosity of 1 cP. Any measurement of viscosity (in a thrombectomy procedure) between the approximate values of 1 cP and 4 cP is indicative of blood which is diluted with saline; the concentration of blood in a diluted state may be determined by embodiments of the present invention. The rate at which viscosity changes may be indicative of the inflow through the distal end of catheter 40.

FIG. 14 shows the absolute pressure at inlet port 145 as may be measured by pressure transducer 165, the data are digitized with respect to nominal (atmospheric) pressure being approximately equal to 370 (annotated nominal pressure 370). Rotor 125 of peristaltic pump 100 is rotated a single revolution (at 300 RPM) such that 3 distinct pressure pulses per revolution are evident as each of the 3 rollers 130 pass inlet port 145. The 3 distinct pressure pulses are shown in pulsed trace 210; rotor 125 is then stopped for a 300 ms dwell. Analyzing continuously pulsatile pressure data (a single cycle of which is shown in pulsed trace 210) can be problematic because of the dispersion (amplitude) of the data. As in the prior art of the U.S. Pat. No. 5,720,721 (the '721 patent), averaging these data over one or more revolutions of rotor 125 is a reasonable approach to finding a time-averaged pressure to compare to reference, library or empirical data. The methodology of the '712 patent averages data over pulsatile trace 210 to determine the average inlet pressure; this single numerical variable (data) is compared to reference, library or empirical data for analysis and classification into attribute data. The '712 patent treats the pressure fluctuations of FIG. 14 as "noise" and employs "noise cancellation" techniques to arrive at an average pressure throughout a plurality of pump revolutions. The techniques of the time domain viscometry may identify multiple potential time constants which may be defined by the pulsations experimentally captured in FIG. 14.

FIG. 14 shows the differential pressure decay shown in stopped slope trace 220 which may be caused by abruptly stopping rotor 125 and initiating a dwell period (of 300 ms in FIG. 14). Data within stopped slope trace 220 provide 2 relevant data sources for viscometric analysis: the initial pressure, $P_0$ 290 and stopped slope 250. These two parameters (or measured quantities) permit quantitative approximation of the of the length of time for the differential pressure to decay to approximately zero, at which time the pressure of inlet port 145 may be approximately equal to the nominal pressure 370. Approximately 4 such complete cycles are shown in FIG. 14; the data of FIG. 14 were collected in approximately 2 seconds for 4 cycles, a single cycle may be completed in approximately ½ second. The repeatability of the repetitions of FIG. 14 illustrates that only a single cycle need be executed for reliable data collection.

Further embodiments of the present invention comprise analysis of data within pulsed trace 210; positive running slope 280 is a pressure increase which may result from roller 130 isolating inlet cavity 143 from inlet port 145. Momentum of fluid in any upstream conduit may explain this effect as fluid momentum is converted into pressure; this pressure pulse may subside. Positive running slope 280 can be seen to be greater than stopped slope 250, the minimum pressure for the cycles is approximately $P_{min}$ 230. Negative running slope 270 is a similar measurable parameter illustrated in FIG. 2, wherein the pressure is decreasing at a characteristic rate. An increasing volume in inlet cavity 143 may explain this feature because the viscosity (and/or inertia) of the fluid may impede rapid filling.

As depicted in FIG. 14, embodiments of the present invention may abruptly stop rotor 125 to measure and quantify the stopped slope 250 and initial pressure $P_0$ 290 (illustrated in stopped slope trace 220) to calculate parameters including a time constant (or analogue) which may be quantifiably deterministic of the fluid viscosity. Further aspects of the present invention might analyze data collected while rotor 125 is rotating by analysis of the data contained within pulsed trace 210. Thus, 5 distinct and quantifiable parameters: stopped slope 250, positive running slope 280, negative running slope 270, $P_{min}$ 230 and $P_0$ 290 are shown herein as distinct and independent methods to quantify the viscosity of a fluid. Additional parameters may be similarly defined from examination of pressure data. The present invention may comprise analysis of data collected while rotor 125 is rotational (spinning), stationary (stopped), accelerating or decelerating in either direction. The present invention comprises analysis of transient pressure responses during unsteady-state flow to determine viscosity and/or rheological properties of the fluid contained within catheter 40.

FIG. 15*a* shows inlet pressure vs. time for a peristaltic pump which has been programmed to sequentially advance rotor 125 approximately ⅓ revolution and stop for a dwell of approximately 200 ms. Rotor 125 is rotated at 7 different rotational speeds: 50, 75, 100, 150, 200, 250, and 300 RPM; 7 corresponding peaks/valleys are evident in FIG. 3*a*. At the completion of this cycle, a dwell time of 600 ms is executed to permit sufficient pressure decay such that successive cycles begin and end at approximately the same pressure. FIG. 15*a* illustrates that the pressure peaks/valleys exhibit amplitudes of approximately the same magnitude (independent upon rotor 125 speed). However the peaks/valleys trend downward (to lower pressures) at faster rotor 125 speeds. These peaks and valleys are approximately bounded by upper bound 310 and lower bound 320; both upper bound 310 and lower bound 320 exhibit similar negative slopes. FIG. 15*a* illustrates that faster rotational speeds generate lower pressures and "steeper" slopes (slopes of greater absolute value, given that half of the slopes are negative and half of the slopes are positive). FIG. 15*a* repeats a cycle to illustrate 3 iterations with repeatable results. For the example peristaltic pump 100, a single cycle (as illustrated in FIG. 15*a*) may be completed in less than 3 seconds and utilize a sample size of less than approximately 3 cc.

FIG. 15*b* shows an enlarged view of data generally bounded by upper bound 310 and lower bound 320 of FIG. 15*a*. The curve is analyzed for the running slopes at 4 different pump shaft speeds: 50, 100, 200 and 300 RPM. The leftmost valley of FIG. 15*b* (50 RPM) exhibits characteristic running slopes such as negative running slope 270 and positive running slope 280 shown in FIG. 3*a*. For graphical clarity, negative running slope 270 and positive running slope 280 are combined to form running angle 50 330, which exhibits a measurable angle which is characteristic for 50 RPM. Also illustrated in FIG. 15*b* are: running angle 100 340, running angle 200 350 and running angle 300 360. The included angle between the positive and negative running slopes is seen to decrease with increasing pump speed. FIG. 15*b* also shows characteristic pressures at 3 local pressure minima: Pmin 50 335, Pmin 100 345 and Pmin 300 365. After the cycle (of 7 pump speeds) is completed, stopped slope 250 is also seen in FIG. 15*b*. FIG. 15*b* shows multiple parameters which may be measured: 4 angles, 1 stopped slope and 3 minimum pressures. For graphical clarity, only a fraction of the measurable parameters are numbered and referenced in FIG. 15*b*. Comparison of FIG. 15*a* and FIG. 15*b* illustrates the repeatability of the above-analyzed cycles; this also illustrates that a large amount of data may be collected with a small sample aliquot or volumetric size in a short amount of time. For viscometric and rheological measurements, there is no need to repeat the cycles as shown in FIG. 15*a*; adequate data for analysis may be collected with less than 3 cc of sample aliquot. FIG. 15*b* illustrates that running angle 50 330 is greater than running angle 100 340 and running angle 300 360 exhibits the smallest included angle. Only the rotational speed of rotor 125 was changed in FIG. 15*b*; at greater rotational speeds, the fluid undergoes a greater rate of shear and a smaller included angle is observed. The ratio of the running angles is characteristic of water, which is considered Newtonian and having approximately 1 cP viscosity. Experimental data collected upon sample fluids may exhibit different running angles 330, 340, 350, and 360 as well as different ratios or slopes. The sample data may be analyzed for non-Newtonian properties including: thixotropic, rheopectic, psuedoplastic, shear-thinning, shear-thickening, etc. by comparison of the respective angles. For consistency, accuracy, repeatability and computational efficiency, it may be advantageous to detect any or all of the peaks and/or valleys depicted in FIG. 14, FIG. 15*a* and FIG. 15*b*; the location of peaks and/or valleys may be determined to be the point where the slope of the pressure trace changes sign.

The experimental data presented in FIG. 14, FIG. 15*a* and FIG. 15*b* were collected upon water; multiple parameters including: time constants, slopes, angles, pressure bounds or values (or analogues) may be calculated from these data. Any such parameters (for water) may be used as calibration data for ratiometric analysis of experimental data subsequently collected upon samples of unknown viscosity. Peristaltic pumps are inherently straightforward to prime and purge; furthermore catheters may typically connect with Luer-Lock fittings, both of which facilitate the rapid changeover from one fluid to another (with or without a change of catheters). A peristaltic pump viscometer may therefore be routinely calibrated in situ with one or more calibration fluids which may generally include water or saline. Time-domain viscometry, conducted on a peristaltic pump, is dependent upon many physical variables including the catheter (length, diameter, flow coefficient, etc.), the dimensions and physical properties of the pump tubing, the pump radius and port location, as well as the size/pressure of each roller 130. These physical variables are subject to variation, change and wear, therefore initial, frequent or routine in situ calibration may provide improved instrument accuracy and precision.

Figure 16A:
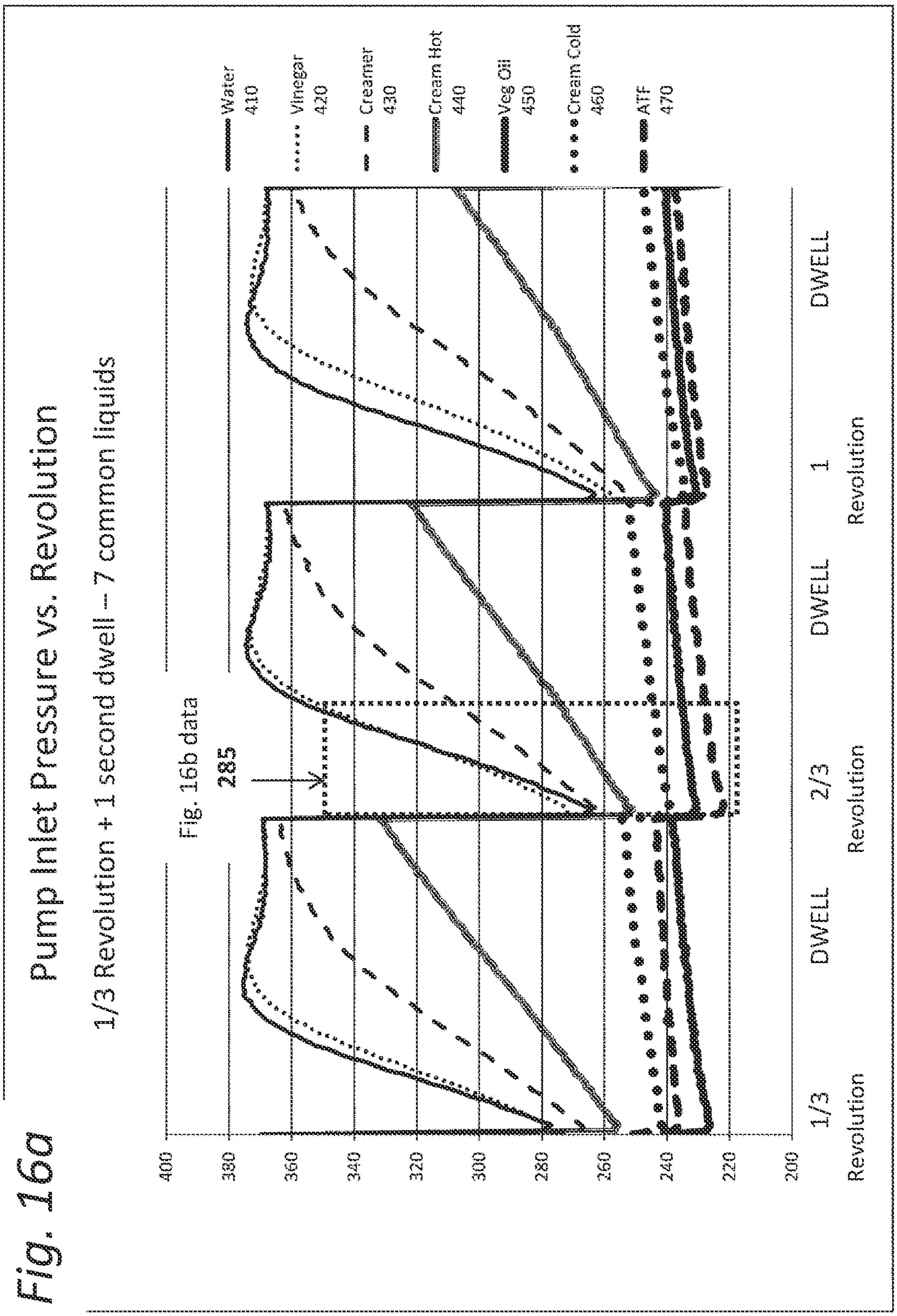
FIG. 16*a* shows pressure traces for 7 different representative fluids. Rotor 125 is rotated ⅓ revolution and a 1 second dwell permits the pump tubing to expand toward nominal dimension.

FIG. 16*a* shows data collected upon an embodiment of a peristaltic pump viscometer with 7 common liquids under test: water 410, vinegar 420, (non-dairy coffee) creamer 430, heavy cream @110° F. 440, vegetable oil 450, heavy cream @45° F. 460, and Dexron IV ATF 470. Analyzed slopes of FIG. 16*a* are stopped rotor slopes (e.g., stopped slope 250); running slopes (e.g., positive running slope 280) are not analyzed in this embodiment. In the example of FIG. 16*a*, approximately 100 data points are collected during the dwell portion of each cycle. These data may be analyzed for any or all of the running slopes and/or minimum pressures as illustrated in FIG. 14, FIG. 15*a* and FIG. 15*b*. The less viscous fluids (water 410, vinegar 420 and creamer 430) exhibit pressure decay sufficient that each new cycle begins at approximately the same initial pressure (approximately 360 to 370). The initial pressures of the more viscous fluids (heavy cream @110° F. 440, vegetable oil 450, heavy cream @45° F. 460, and Dexron IV ATF 470) are seen to decrease with each successive cycle. Greater dwell time will allow for sufficient pressure decay such that the initial pressures return to approximately nominal. Data from the first cycle is sufficient for viscometric analysis, and a longer dwell time (for the more viscous fluids to approach equilibrium) is not required. The running and/or stopped slopes and/or minimum pressures provide sufficient data (in a single ⅓ revolution cycle) for viscometric analysis with a total fluid transfer less than approximately 0.4 cc in the experimental embodiment under test.

Figure 16B:
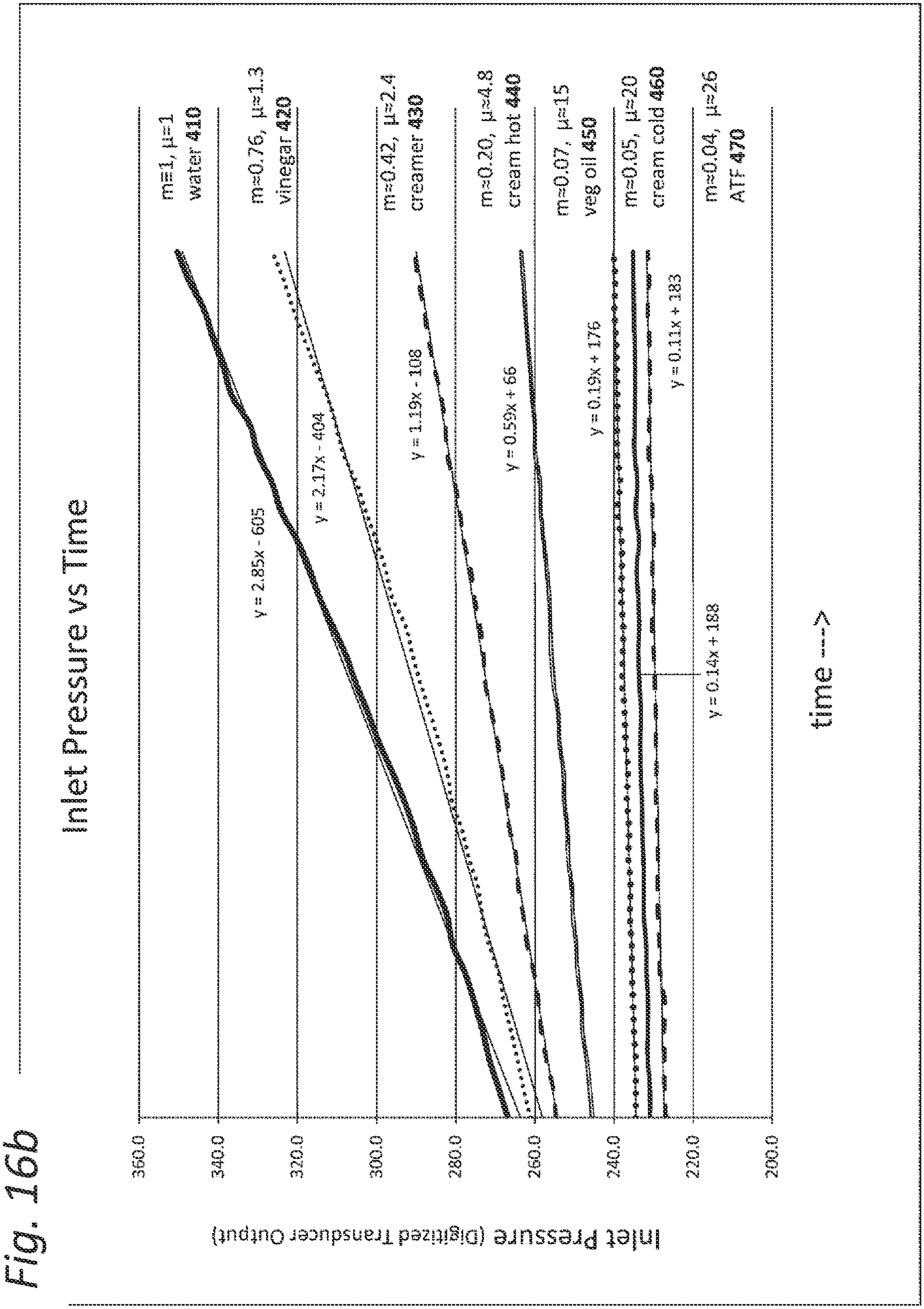
FIG. 16*b* shows linear regression analysis of a portion of the data of FIG. 16*a*. A first order approximation of viscosity is calculated for each of the 7 representative fluids.

FIG. 16*a* shows three repetitions of a cycle of duration slightly in excess of 1 second each. However, all of the pertinent data are contained in a fraction of the time as is illustrated by FIG. 16*b* data 285; FIG. 16*b* shows linear regression of the data contained therein. In FIG. 16*a*, cream hot 440, vegetable oil 450, cream cold 460 and ATF 470 exhibit approximately linear pressure decay with relatively constant slope throughout the dwell; (non-dairy) creamer 430 exhibits a curvilinear pressure decay which may be logarithmic in nature. As the dwell time is increased to approximately three or more time constants of the more viscous fluids, the exponential decay may be visually detected; FIG. 16*a* shows the more viscous fluids during the initial phase of exponential pressure decay. FIG. 16*a* shows that the water 410 and vinegar 420 "overshoot" the nominal pressure; this may be due to fluid inertia effects. Creamer 430 exhibits a pressure decay trace which is exemplary of an exponential decay as depicted in the time scale of FIG. 16*a*.

Some embodiments of the present invention employ linear regression throughout or at periods within the dwell time to find the pressure decay slope; however this may not be suitable for certain fluids, including water 410, vinegar 420, and (non-dairy coffee) creamer 430 because of the curvilinear nature of their respective pressure decay. Examination of the data contained within FIG. 16*b* data 285 reveals generally linear pressure traces (generally constant slope throughout a region). Linear regression is depicted in FIG. 16*b* in order to: (1) validate the observation of linearity within the region and (2) numerically illustrate the calculated slope and mathematical techniques disclosed herein to convert the calculated slope into a calculated viscosity. Preferred embodiments of the present invention may employ finite-difference techniques to measure the slope in a computationally efficient manner.

FIG. 16*b* shows linear regression of the 7 representative fluids. The 7 (stopped rotor) slopes include $m_{water}\approx 2.85$ for water 410, $m_{vinegar}\approx 2.17$ for vinegar 420, . . . $m_{ATF}\approx 0.04$ for ATF 470. Each of these slopes may be normalized to water 410 by dividing by $m_{water}\approx 2.85$. The inverse of the slopes is a first order approximation of viscosity. Using a linear regression embodiment of the present invention, the first order approximations of viscosity are:

$$\mu_{water}\equiv 1\text{ cP};\ \mu_{vinegar}\approx 1.3\text{ cP};\ \mu_{creamer}\approx 2.4\text{ cP};\ \mu_{cream\ hot}\approx 4.8\text{ cP};$$

$$\mu_{veg\ oil}\approx 15\text{ cP};\ \mu_{cream\ cold}\approx 20\text{ cP};\ \mu_{ATF}\approx 26\text{ cP}.$$

Other embodiments of the present invention calculate the pressure decay slope using only a small fraction of the collected stopped slope data. Experimentally, it is found that data from the $1^{st}$ through the $30^{th}$ data points (of the 100 data points collected) provide the necessary and sufficient data for first order viscometric determination. FIG. 16*c* presents analysis of the data of FIG. 16*a*. FIG. 16*c* has columns which are identified as the 7 fluids under test. The rightmost column (Visc Factor) is representative of any plausible relationship between the data and the viscosity of the fluid under test. VF1 is the reciprocal of the normalized slope, and is a first order approximation of viscosity. Viscosity Factor 1 (VF1) may be herein considered a time constant; it represents an amount of time required for an amount of differential pressure decay.

In FIG. 16*c* column 1, 480 (identified as Water) shows calculations made upon pressure data in accordance with embodiments of the present invention. Row 1 485 is the calculated slope of a portion of the data depicted in FIGS. 15*a* and 15*b*; the slope is in arbitrary units and scale. A finite difference method is used to calculate the slope in this embodiment. The entry of row 1 485, column 1 480 is 71.1, this is identified as the slope of this data in the left-most column. The measured slope for water (Row 1, Column 1) has a value of 71.7; this measurement may have the units of pressure/time (e.g., Pa/s, psi/s, etc.); for subsequent calculations, slopes may be considered dimensionless herein. The calculated stopped-rotor slope (for water) of 71.7 is used to normalize (and optionally non-dimensionalize) data to a reference standard of approximately 1 cP (for water). The value of 71.7 is resultant from the system variables including catheter length, diameter, pump specifications, tube dimensions and physical properties, etc. The remaining columns provide similar data for each of the 7 fluids under test. Row 2 of FIG. 16*c* normalizes the slope to value of 1 for water, in part because water has a viscosity of approximately 1 cP. Approximating the slope of the pressure decay for any fluid provides a straightforward, first-order approximation of the viscosity of that fluid. A representative first-order approximation of viscosity is shown in row 3, designated 1/(Norm Slope); row 3 is also designated as VF1, for Viscosity Factor 1. Using a finite difference embodiment of the present invention, the first order approximations of viscosity are:

$$\mu_{water}\equiv 1\text{ cP};\ \mu_{vinegar}\approx 1.3\text{ cP};\ \mu_{creamer}\approx 2.4\text{ cP};\ \mu_{cream\ hot}\approx 4.8\text{ cP};$$

$$\mu_{veg}\text{ oil}\approx 15\text{ cP};\ \mu_{cream\ cold}\approx 20\text{ cP};\ \mu_{ATF}\approx 26\text{ cP}.$$

The finite difference first order approximations exhibit different measurement values than previously calculated using linear regression on linearized exponential data; experimentation may reveal the preferred method for the application. Because viscosity and flow are reciprocals of one another, measuring any slope, at any point in time, is a first order approximation of the flow rate. Row 2 of FIG. 16*c* is the normalized slope of each of the 7 representative fluids. Finite difference approximations of the slope may yield better results (agreement with calibration standards) than linear regression because finite difference estimates the slope at a point (at about the $115^{th}$ data point or approximately 150 ms after rotor 125 is abruptly stopped, in this embodiment). Conversely, linear regression finds the best solution for linearizing data over a range of data (rather than at a point).

Additional and relevant information may also be gleaned by embodiments of the present invention to improve the accuracy and precision of the viscometric and rheological measurements. Row 4 of FIG. 16*c* captures the minimum pressure within a cycle; more viscous fluids tend to exhibit lower minimum pressures. Row 5 normalizes the minimum pressure to water; for example vegetable oil exhibits a pressure factor of 1.22; vegetable oil draws 1.22 times greater vacuum than water in a corresponding cycle. Row 5 is designated as Pressure Factor; row 5 is also designated as VF2, for Viscosity Factor 2. Row 6 is the range of the slope data and is designated as VF3, for Viscosity Factor 3. Viscosity Factor 2 and Viscosity Factor 3 may also herein considered to be time constants. For instance, using example the pressure factor (VF2) value of 1.22 for vegetable oil, one may arrive at a first order approximation of 1.22 cP for vegetable oil, a very poor approximation. Alternatively, taking the quotient of the ranges (VF3), one may arrive at an approximation of 15 cP, a much better approximation.

Row 3 of FIG. 16*c*, designated VF1 (viscosity factor 1), is the inverse of the slope and a first order approximation of viscosity. The presented data exhibit a degree of fidelity to reference data for the representative fluids, however neither accuracy at a point, nor linearity over a span may be assumed without experimentation. Additional viscosity factors (VF2 and VF3 as examples) may be gleaned from the data which provide additional variables for mathematical modeling. Row 7 shows a representative mathematical function which combines the two measured viscosity factors (VF1 and VF2); in this example VF1 is raised to the power VF2. Alternatively, Row 8 shows the product of VF1 and VF2. Rows 7 and 8 are representative higher-order approximations of viscosity which may be experimentally correlated to reference data. Rows 7 and 8 of FIG. 16*c* illustrate that viscosity factors and time constants may be mathematically manipulated to fit experimental data as may be required by the application.

FIG. 16*d* shows an abridged version of the data of the analyses of FIG. 16*c*. In this embodiment, a finite difference slope is calculated from the averages of blocks of data which include a time interval. For example, data points 101 through 105 are averaged, as are data points 126 through 130; the difference in these averages is a first order, finite difference approximation of the slope at approximately data point 115 (under the assumption of constant sampling rate). This finite difference approximation may be normalized to any convenient value such that variables including the sampling rate, system compliance and resistance, etc. are embedded in the analyses. Row 2 of FIG. 16*c* depicts the normalization of the slope of each representative fluid by dividing by the slope of water. A non-dimensionalizing coordinate transformation is undergone which re-defines the slope of each fluid line such that it is a fraction (or multiple) of the slope of water. FIG. 16*d* invokes the mathematical relationship proportional to, annotated by x, wherein the difference in pressure (between two instances in time) is proportional to the slope (in arbitrary dimensions and units). Given that each of the example fluids exhibits a measured slope in the same arbitrary dimensions and units, then the quotient of the slopes algebraically eliminates all arbitrary constants. The techniques of time-domain differential viscometry invoke this by taking the quotient of two measured parameters (e.g., time constants of a first fluid and a second fluid) and ratiometrically determining the quotient of two derived parameters (e.g., viscosity of a second fluid given the known viscosity of the first fluid).

Preferred embodiments of the present invention comprise the integration of peristaltic pump 100, pressure transducer 165 and catheter 40 with system controller 600 to implement time-domain viscometry in fluid systems such as thrombectomy systems. More generally, components for time-domain viscometry include a means to measure pressure, a fluid conduit (catheter), a non-isovolumetric component, and a source of differential pressure. A peristaltic pump provides a non-isovolumetric component (pump tubing) and differential pressure to generate fluid flow. Peristaltic pumps are pulsatile in nature, and provide data that may be considered noisy; these data were therefore subjected to averaging in prior art. Aspects of the present invention analyze the unsteady flow generally provided by a peristaltic pump for viscometric analysis. Specifically, a peristaltic pump may be operated in uninterrupted or interrupted fashion such that any resultant unsteady flow regimes which arise may be analyzed for measurable quantities including pressure decay rate, pressure range, extrema, etc.

Thermo-fluid sciences provide few exact solutions wherein experimental data match corresponding theory without any need for experimentally derived constants. Experimental data are routinely conditioned by means of coordinate transformations, curve-fitting and numerous other techniques to fit experimental data to reference data. Reducing the present invention to practice may comprise curve fitting approximations including: exponential, logarithmic, power, polynomial, spline, etc. The disclosed first order approximation of viscosity is the inverse of a stopped slope 250. In the same manner, positive running slope 280 such as running angle 330, 340, 350, 360, etc. (at variable rotor speeds), negative running slope 270 provide additional first-order approximations of viscosity at varying rates of shear. Additional data including minimum pressure 335, 345, 365, etc., upper bound 310, lower bound 320 and range provide a multitude of measured variables for higher order approximations. Each of these measured variables may be considered an $i^{th}$ Viscosity Factor (or VFi); these viscosity factors may be non-dimensionalized or considered dimensionless for use in logarithmic, exponential, power and polynomial functions. The nature and number of the Viscosity Factors to be measured and evaluated is dependent upon the application and desired accuracy.

As representative embodiments of the present invention, two higher order approximations are disclosed in the forms of:

$$\mu_1 \approx k_1 (VF1)^{k2VF2} \quad \text{(Eq. 25)}$$

$$\mu \approx k_3 (VF1) \times (VF2) \quad \text{(Eq. 26)}$$

where $k_1$, $k_2$ and $k_3$ are experimentally determined calibration constants. Eq. 25 and Eq. 26 are closed-form solutions which are comprised of experimental data and calibration constants which may be valid over a range of data. This is in contrast to prior art wherein experimental data are correlated to reference or library data including charts, tables, spreadsheets, etc. Thus, the present invention provides $1^{st}$ and $2^{nd}$ order approximations of viscosity by employing mathematical relationships between experimental data and calibration constants $k_1$, $k_2$ and $k_3$ resulting in viscosity measurement; flow may be directly inferred. These two disclosed forms (eq. 25 and eq. 26) are representative of generalized data conditioning and curve fitting techniques which may be determined by experimentation in conjunction with experimental data collected upon calibrated viscometers or viscometric standards.

Peristaltic pumps are referenced herein for time-domain viscometry because two requisite components are necessarily present: (1) a source of differential pressure, and (2) a non-isovolumetric component. The present invention may be reduced to practice with other types of pumps including: gear pumps, diaphragm pumps, piston pumps, syringe pumps, progressive cavity pumps, as well as dynamic pumps including axial and centrifugal pumps. The example control system for collecting and analyzing the experimental data presented herein may be comprised of one or more SBC's (Single Board Computers) such as Arduino, Raspberry Pi, etc. All experimental components were sourced through Amazon which shows the cost at the time of filing: (1) Arduino Uno (≈10 US$), (2) peristaltic pump (≈10 US$), (3) pressure/vacuum transducer (≈20 US$), (4) TB6600 microstep driver (≈10 US$), (5) a length of tubing/catheter (≈1 US$). The entirety of the experimental apparatus may be commercially sourced for approximately 50 US$. It is anticipated that other components and/or control systems may be substituted; programming may be accomplished by software programs or programming languages such as C++, Python, LabView, Visual Basic, etc. The present invention may be reduced to practice using any appropriate or analogous controller and/or programming language including proprietary hardware and/or software. The Arduino Uno is representative of any generalized controller which comprises an appropriate processor, volatile and involatile memory, analog and digital I/O and human/machine interfaces. The TB6600 microstep driver used is representative of any motor control system which may allow control over acceleration/deceleration, position and speed. Selected embodiments of the present invention employ the calculation of derivatives, slopes or curvature through finite difference approximations; these embodiments are illustrative of line-by-line programming languages including C++, Python, etc. In contrast, graphical programming languages including LabView, Visual Basic, etc. may include function calls including: calculate slope, calculate derivative, calculate curvature, etc. The scope of the present invention comprises both explicit algebraic calculation of derivatives, slopes and curvature as well as function calls of higher-level programming languages.

A distinction of the present invention over prior art is the generation of quantitative viscosity measurements which may be converted to engineering units, which are variable data. Prior art correlates pressure data to reference or library data to generate attribute data (classification) such as: low flow, high flow, thrombus, clot, clog, obstruction, etc. It is anticipated that such attribute data may be subdivided multiple times such that the attribute data approaches variable data in the limit of a large number of subdivisions. With a large number of attributes available (very tiny, tiny, very small, . . . very big) viscometric analysis may be approximated with multiple conditional statements (of prior art) instead of closed form expressions (of the present invention).

Some thrombectomy systems feature infusion concomitantly with aspiration; this is described and illustrated in references including co-pending U.S. patent application Ser. No. 17/409,635. Infused fluid, typically saline, is generally transported the length a thrombectomy catheter and discharged at or near the distal end. It is anticipated that aspirate sampled from such a system will exhibit a decrease in aspirate viscosity as dilution with saline may occur within the catheter aspiration lumen. The infusion flow rate may be under system setpoint control or may otherwise be known; the aspiration rate (e.g., flow through peristaltic pump 100) may be known or measured by methods of the present invention. For an infusion+aspiration thrombectomy system, the present invention enables improved thrombectomy operating modes to be performed. As an example, the infusion rate may be set equal to the aspiration rate (or vice versa). Assuming zero fluid transfer into and out of the distal opening of the aspiration catheter, a saline/blood interface may form and traverse the length of the catheter (distally to proximally). The large aspect ratio (approximately 50:1 or greater) of a catheter tends to minimize diffusion across the interface because of the small interface area. This type of flow may be termed "plug flow" in fluid mechanics.

To illustrate an improved thrombectomy operating mode, the following sequence of events may occur:

(1) The aspiration pump is operational at 1 cc/second (as determined by time domain viscosity) and the infusion pumps is off; the catheter is filled with patient blood (at 4 cP).

(2) Thrombus is contacted by the distal end of the catheter and a clogged or corked condition is encountered; the measured viscosity is very large (e.g., greater than 500 cP); the flow rate decreases as a function of the measured viscosity.

(3) The infusion pump is made operational at a flow rate of 1 cc/second, the aspiration pump may now attain a flow rate of 1 cc/second as saline displaces blood along the length of the catheter.

(4) The viscosity of the aspirate may be observed to decrease approximately linearly between 4 cP and 1 cP.

(5) The catheter is now filled with saline at 1 cP viscosity.

This sequence of events may be termed a "saline flush" and may seem of no consequence with the stated initial condition wherein blood at 4 cP generally fills catheter 40. However, when the initial condition is a catheter filled with thrombus exhibiting a viscosity greater than blood (e.g., 40 cP) then the flow rate will be correspondingly less than 1 cc/second. If the measured viscosity exhibits a sudden (e.g., occurring in less than approximately 1 second) increase (e.g., to 500 cP) then the previously described "saline flush" may be effective in replacing thrombus (contained within the catheter) with saline. The cause of the sudden increase (to e.g., 500 cP by a flow anomaly e.g., a clot, clog or distal occlusion) may be attacked with low-viscosity, high-flowing saline at 1 cP.

The preceding example "matched" the infusion and aspiration flow rates to create plug flow and a moving interface between blood/thrombus and saline. Other embodiments may entail aspirating at a greater rate (e.g., 2 cc/s) than infusion (e.g., 1 cc/s) for a net inflow of patient blood of 1 cc/s. This may be advantageous because the average viscosity of the blood/thrombus/saline mixture contained within the catheter may be less than the average viscosity of the blood/thrombus mixture present in the absence of aspiration. The net inflow to the catheter may thereby achieve the desired flow rate of 1 cc/second, however the measured, effective or average viscosity of the fluid contained within the catheter is diminished by dilution with saline. When thrombus, clot or clog are encountered during a thrombectomy procedure, the effectiveness, efficacy and time-efficiency may be improved when the fluid contained within the catheter is of low viscosity. An example catheter 150 cm (1.5 m) in length may be discretized into 150 elements of 1 cm length each; and an example bolus of thrombus of 1000 cP may also be approximately 1 cm in length and is contained in the distal end of the catheter. If the catheter is otherwise filled with saline at 1 cP the measured viscosity may be approximately (149×1 cP+1×1000 cP)/150≈8 cP; if the fluid within the catheter is blood at 4 cP, the measured viscosity may be approximately (149×4 cP+1×1000 cP)/150≈11 cP and if the fluid within the catheter is thrombus at 20 cP, the measured viscosity may be approximately (149 cm×20 cP+1 cm×1000 cP)/150 cm≈27 cP. This example illustrates why it may be advantageous, in a thrombectomy procedure, to have low viscosity fluid in the catheter, particularly when thrombus is encountered. While systems of prior art may utilize techniques such as "saline flush," the present invention enables a quantitative approach to controlling the measured viscosity of the fluid contained within the catheter and thereby afford maximum thrombus, clot and clog clearing efficacy and efficiency. Preferred embodiments employ saline flush and monitoring as automated control system responses and may be evoked with the aid of techniques including Statistical Process Control (SPC), PID control, fuzzy logic control, etc.

As a relevant clinical example of an improved thrombectomy procedure, a "pocket" of thrombus of approximately 100 cP may be encountered at the distal end of catheter 40 and aspirated, creating a bolus. As this bolus of thrombus (within catheter 40) advances and grows in length proximally through the catheter, the measured viscosity may continually increase. For instance, if thrombus at 100 cP occupies 40% (90 cm) of the catheter length (with blood residing in the remaining catheter length, 60 cm) then the measured viscosity may be approximately (90 cm×100 cP+60 cm×4 cP)/150 cm=61.6 cP. This measured average viscosity may now exhibit a time constant approximately 60 times greater than $\tau_{saline}$. If the pocket of thrombus is not yet depleted, then the measured viscosity may continue to rise. But if a saline flush is conducted at some threshold measured viscosity (e.g., 60 cp, 10 cP, 100 cP, etc.) then the subsequent measured viscosity may be returned to below 5 cP with a correspondingly short time constant; thus an automated saline flush during thrombus extraction may reduce the time required perform the aspiration of this "pocket" of thrombus and similar thrombi as well.

The embodiments chosen for inclusion herein have incorporated pressure transducers, high speed data sampling rates (compared to the time scale of the measured phenomena), and multiple calculations being performed on sizeable amounts of data. Time domain viscometry may also be implemented with a human, a stopwatch, and a means to control the pressure within a non-isovolumetric component; this means may be a pump, a valve, a pressurized reservoir, etc. In a manual embodiment: (1) a differential pressure is established in the non-isovolumetric element, distorting it, (2) the differential pressure is relieved such that flow into/out of the non-isovolumetric component exists, (3) the human starts the stopwatch at a first pressure and stops the stopwatch at a second pressure. The human calculates the slope of the pressure decay; the inverse of the slope is a first order approximation of viscosity. This is in contrast to capillary and drip cup viscometers of prior art because herein: (1) pressure is supplied by a distorted non-isovolumetric component (as opposed to gravity), and (2) the time for a prescribed pressure decay is measured (as opposed to the time for a prescribed volume of fluid to flow).

The disclosed embodiments provide the following:

1. a fluid conduit (catheter 40)
2. Five example deformable (non-isovolumetric) elements:
   - 2.1 compliance chamber 30, 900
   - 2.2 spring compliance chamber 865
   - 2.3 syringe compliance chamber 1000
   - 2.4 vapor or gas 1095
   - 2.5 tubing including peristaltic pump tubing
3. Three example sources of differential pressure or positive aspiration:
   - 3.1 vacuum reservoir 10
   - 3.2 liquid pump 850, including peristaltic pump
   - 3.3 syringe compliance chamber 1000
4. Two example means to change the rate of flow through catheter 40:
   - 4.1 valve 855 and/or valve 20
   - 4.2 liquid pump 850
5. Three example means to change the volume of the deformable member:
   - 5.1 2 example pressure means:
     - 5.1.1 vacuum reservoir 10 and valve 20 or valve 855
     - 5.1.2 liquid pump 850 and valve 855
   - 5.2 1 example force means:
     - 5.2.1 actuator 1040
6. Four example means to perform time domain viscometry
   - 6.1 determine the time at which saline trace 550 and/or blood trace 560 intersects 0.368 line 368, create saline drop line 510, blood drop line 520 to find time constant, τ, for any sample
   - 6.2 execute finite difference calculation of slope of saline slope line 515, blood slope line 525 in linear coordinates to find time constant, τ, for any sample
   - 6.3 execute finite difference calculation of slope of saline trace 550, blood trace 615 in linearlized coordinates to find time constant, τ, for any sample
   - 6.4 execute numerical integration of pressure trace to find time constant, τ, for any sample.

Embodiments may comprise a system controller 600 which may orchestrate the succession of charging, measuring and calculation steps, along with the initiation and execution of any system response to any calculation. The calculate tau subroutine 700 algorithm of FIG. 7 illustrates a representative step-wise procedure to measure viscosity and/or flow and quantitatively assess the aspirate viscosity and/or characteristic. Step open valve 704 precedes measurement of P0 in step measure P0 706 (the charging step). Step close valve 708 initiates the measurement step, which consists of successive pressure measurements in step Measure Pi 712, which is shown to be repeated n times at intervals of time. Subsequently, the calculation step is depicted in step calculate tau 714. The calculate tau subroutine 700 returns a value quantitatively descriptive of viscosity and/or flow may be expressed in the units of time as a time constant; these values may be algebraically manipulated to quantitatively describe the aspirate with respect to any reference or calibration data, e.g., saline or blood.

Time domain viscometry is presented herein in the context of a thrombectomy system, however many inventive subsystems have relevance in other disciplines including: industrial, scientific, automotive, civil engineering, in addition to the medical-device applications presented herein. The invention discloses the methodology to inexpensively redesign or retrofit existing products to incorporate the ability to discriminate inhomogeneous inflow and subsequently update a control output setpoint and/or optional valve positions. Inhomogeneous inflow may be separated based upon variable data input including viscosity, absorption, conductivity, etc.; valves may be used to divert fluid to different reservoirs. Homogeneous inflow may be periodically viscometrically measured for changes in variable input data over time to determine onset and/or degree of fluid degradation. The scope and detail of this disclosure, combined with a broad array of embodiments enable persons skilled in the art to implement time domain differential viscometry and associated control systems in ubiquitous applications.

In summary, aspects of the present invention include, among any others:

A time-domain viscometer which measures the time rate-of-change change of a fluid property (pressure) and quantitatively determines additional fluid properties (viscosity and/or flow).

A thrombectomy system which comprises a time-domain viscometer.

A thrombectomy system which is in-situ calibrated to one or more homogeneous fluids.

A thrombectomy system which analyzes inhomogeneous patient data with respect to data from homogeneous fluids.

A thrombectomy system which analyzes inhomogeneous patient data with respect to homogeneous patient data.

A thrombectomy system which quantitatively determines fluid properties (viscosity and/or flow rate) of homogeneous and/or inhomogeneous patient data.

An automated thrombectomy system which controls the setpoints of system components in response to quantitative viscometric analysis of patient data.

An automated thrombectomy system which achieves the maximum attainable vacuum in response to viscometric analysis of patient data.

An automated thrombectomy system which aspirates a minimum amount of viable blood while concomitantly aspirating a maximum amount of thrombus in a minimum amount of time.

The preceding disclosure may now be compared to prior art to identify the similarities and differences; the differences helping define the scope of the prior art as distinct from scope of the present invention. The '683 patent discloses an algorithm in FIG. 13 comprising measuring ΔP and comparing the magnitude to three arbitrary constants (ΔPmin, ΔPmax and X) over an undisclosed time period T, defined as "optimized sample period." ΔPmin, ΔPmax and "confidence multiplier" X are not defined. In this process, variable data (ΔP) are collected and converted to attribute data by conditional statements with experimental data and arbitrary constants as arguments. If ΔP is greater than ΔPmin and if ΔP is less than the product of X and ΔPmax then the outcome of any iteration is always "clot." If confidence multiplier is "too small," then the outcome of any iteration of the flowchart is always "clot." This illustrates that the control system may not be robust to changes in the arbitrary constants; outcomes may be biased toward a preferred or otherwise erroneous classification of "clot" or "open flow." Note that intensive variable data (ΔP) is collected in pressure units and the flowchart returns the attribute data value of "clot" or "open flow" which do not have dimensions or units. There are two outcomes of the flow chart: Stay Open . . . and Stay Closed . . . , and there are two attribute data characteristics: clot and open flow.

The '683 patent states: " . . . the sensing unit is configured to determine flow rate within the connecting tube and to produce a signal representative of such flow, typically as either unrestricted flow, restricted flow, or clogged." This illustrates the use of attribute data with three defined levels or characteristics. The sensing unit is depicted and described in embodiments to comprise a pressure sensor. Pressure is measured dimensions of $[FL^{-2}]$ and may have units such as Pascal (Pa) or psi; and the " . . . the sensing unit is configured to determine . . . either unrestricted flow, restricted flow, or clogged." Herein dimensioned variable pressure data is converted to dimensionless attribute data termed "flow rate." In engineering units, flow rate may be expressed in dimensions of $[L^3T^{-1}]$ with units including $m^3/s$ or liters per minute or cc per second, etc. The '683 disclosure does not instruct how to transform intensive variable data (pressure) with dimensions of $[FL^{-2}]$ to extensive attribute data (flow rate) with dimensions of $[L^3T^{-1}]$. The '683 does not instruct how to "determine flow rate" in engineering units (e.g., 1 cc/second, 1 liter/minute, etc.) but does allude to a method to "determine . . . either unrestricted flow, restricted flow or clogged." The '683 patent determines and evaluates attribute data to effect a control system response.

U.S. Pat. No. 11,716,880 (the '880 patent) states "a first sensor configured to measure a characteristic of flow" and subsequently "A 'characteristic of flow may include a pressure, a flow rate, a flow velocity or a variation or disturbance in any of these." A layman's definition of characteristic may be "typical of a particular person, place or thing," and a statistician's definition of characteristic may be "Attribute data is [sic] data that have a quality characteristic (or attribute) that meets or does not meet product specification." The first sensor is illustrated and described to comprise a pressure transducer which outputs variable data measurement of the intensive property pressure, but no means is disclosed therein to convert the intensive property pressure into the extensive property flow. Claim 1 of the '880 patent includes: " . . . and a controller configured to . . . vary the operation of the peristaltic pump based at least in part on . . . a change in the characteristic of flow." The '880 patent monitors for and detects a change in attribute data (e.g., characteristic of flow) at least in part to vary the operation of the peristaltic pump.

Alternatively, the sensor of the '880 patent may comprise an ultrasound sensor wherein "The pulse count above/below one or more pre-determined thresholds is ultimately what determines whether the overall system is in a free-flow or clot removal state and to what degree." Ostensibly, an ultrasound sensor is capable of generating variable data in engineering units such as: cc/second, liters per minute, etc.; however the '880 disclosure and claims repeatedly state: " . . . a change in the characteristic of flow . . . " wherein a first characteristic (e.g., free-flow) changes to a second characteristic (e.g., clot removal). The embodiments, disclosure and claims of the '880 patent demonstrate a methodology that monitors and detects changes in discrete attribute data; detection of these changes is used to determine discrete control system responses.

An example from prior art is U.S. Pat. No. 5,720,721 (the '721 patent) wherein a peristaltic pump is used as a metering pump; pressure transducers are in fluid communication with the inlet and outlet ports of a peristaltic pump. Therein viscosity is "monitored" by a single pressure transducer (reading strain in units of psi) on the pump inlet port. Two values of strain are recorded: "strain running" and "strain stopped" as calibration data for a given fluid of unknown viscosity. Therein, a change in running strain (over an arbitrary length of time) is referred to as a change in delta strain, and is purportedly inferred to represent a change in viscosity. Only the inlet pressure is measured, so therein delta strain means a change pressure over time. From the '721 patent: "It is presently believed that the increase in rotations necessary to compensate for the occlusion or higher viscosity is proportional with the delta strain with an empirically defined range." An " . . . empirically defined range . . . " therefore means invoking an arbitrary calibration constant which may have units of (N rotations)/psi and dimensions of $[L^2F^{-1}]$; this arbitrary calibration constant may be obtained through empirical or experimental means. The '721 monitors pressure and purports to thereby monitor viscosity, but the disclosure reveals that an increase in rotations proportional to delta strain (multiplied by an arbitrary constant) is believed to compensate for "the occlusion or higher viscosity." Therein, variable data (delta strain) is used synonymously with pressure as used herein.

The invention is presented herein in the context of a thrombectomy system, however many inventive subsystems have relevance in other disciplines including: industrial, scientific, automotive, civil engineering, in addition to the medical-device applications presented herein. The invention discloses the methodology to inexpensively redesign or retrofit existing products to incorporate the ability to discriminate inhomogeneous inflow and subsequently update a control output setpoint and optional valve positions. The scope and detail of this disclosure, combined with a broad array of embodiments enable persons skilled in the art to implement time domain viscometry and associated control systems in ubiquitous applications.

In order to provide a clear and consistent understanding of the disclosure and the appended claims, including the scope to be given such terms, the following glossary of terms and definitions is provided.

Viscosity—the resistance of a fluid to flow; herein including the resistance of a homogeneous liquid or inhomogeneous mixture of liquids and/or solids to flow through a catheter or conduit. Example: an inhomogeneous mixture of thrombus and blood might be uniformly distributed or spatially discrete along the length of a catheter. The viscosity of this inhomogeneous mixture may be measured by a viscometer. The measured viscosity may be approximately inversely proportional to the rate of flow through the catheter. Herein viscosity may be construed to mean the average or effective viscosity of fluid contained within a conduit or catheter. Eq. 0 provides a mathematical description where $\hat{\mu}$ is the viscosity of a differential fluid volume element; the effective or average viscosity may be calculated by integrating the viscosities of the differential fluid volume elements along the length of the catheter.

$$\mu \approx \frac{1}{L}\int_0^L \hat{\mu}dx \qquad \text{Eq. 0}$$

Note that if even a single differential fluid volume element has a very large value of $\hat{\mu}$ (e.g., greater than approximately 10,000 cP) the measured, effective or average value of μ will also increase to a very large value. Thus, a clogged or corked catheter might be indicated by a very large value of μ.

Viscometer—An instrument that measures the viscosity of fluids. Herein, viscometer generally means any apparatus that: (1) employs any system of creating flow through a conduit or catheter, (2) concurrently measures the rate of change of fluid pressure and (3) determines the viscosity of the fluid contained within the conduit or catheter. Viscosity may be measured in arbitrary units which may or may not be converted to engineering units. Example: a first oil exhibits a time constant of 30 seconds and a second oil exhibits a time constant of 90 seconds. The arbitrary unit of the example is time.

Time Constant—a characteristic length of time for a system parameter or signal (current, voltage, pressure, volume, flow, etc.) to change (herein e.g., return toward equilibrium) by a specified amount. A reduction to 1/e, or approximately 36.8% of the initial value is mathematically convenient example. Herein, multiple time constants may be defined depending upon system parameters including rotor speed, rotor position, compliance chamber volume, etc.

Differential Viscometer—An instrument that measures the ratio or difference in viscosity between two or more liquids, e.g., water and oil, or an unknown fluid and a reference fluid. Differential viscometry may ratiometrically determine the viscosity of an unknown fluid with respect to a reference fluid. Example: water (1 cP viscosity) exhibits a time constant of 1 second and an oil exhibits a time constant of 30 seconds: the viscosity of this oil may be approximately 30 times greater than water, the viscosity of the first oil may be approximately equal to 30 cP. The engineering unit of the example is cP.

Viscometry—Herein, the process of measuring the viscosity of a fluid sample or aliquot which may be transported from a first fluid reservoir to a second fluid reservoir by means of a conduit or catheter; the viscosity of the fluid sample or aliquot within the conduit or catheter is measured.

Catheter—any fluid conduit with a (large) length-to-diameter aspect ratio greater than approximately 50. Diameters may range from sub-millimeter to meters (at corresponding lengths). For flow calculation example purposes, herein a representative catheter is considered to be in the ranges of 3Fr to 12Fr (1 mm to 4 mm) diameter and between 50 cm and 200 cm in length.

Fluid—Any combination of liquids, vapors, gasses and solids which may be transported through a conduit.

Fluid Property—any intensive or extensive property of a fluid which may be measured. Relevant intensive fluid properties include pressure, viscosity, temperature, etc.; relevant extensive fluid properties include volume, mass, flow rate, time, etc.

Fluid Homogeneity—the absence of spatial gradients of a fluid property within the fluid.

Fluid Inhomogeneity—the presence of spatial gradients of a fluid property within the fluid. Spatial gradients (of fluid property) in an inhomogeneous fluid become temporal gradients as an inhomogeneous fluid is sampled or aspirated and measured.

Aliquot—a portion of a larger whole, especially a sample taken for analysis.

Homogeneous Fluid—any sequence of fluid aliquots, from a reservoir of fluid, which exhibits negligible measurable deviations in a fluid property (viscosity) with respect to time. Examples: water, saline, viable blood, oil, etc.

Inhomogeneous Fluid—any sequence of fluid aliquots, from a reservoir of fluid, which exhibits significant measurable deviations in a fluid property (e.g., viscosity) with respect to time; these deviations in viscosity may be indicative of changes of the fluid composition of the aliquot. Examples: a time-dependent sequence of saline, blood, blood containing 10%, 20%, 30% . . . thrombus, blood containing saline, blood containing clots, etc.

Pressure—spatially continuous physical force exerted on or against an object by something (generally a fluid) in contact with it. Pressure may be measured and expressed in absolute or gage units; gage units may be offset/translated to atmospheric or other reference pressure.

Vacuum—a condition below atmospheric pressure, local pressure or other reference pressure. Vacuum may be preferred in reference to gasses and vapors.

Suction—a differential pressure that may induce fluid flow toward the source. Suction may be preferred in reference to liquids, solids, slurries, inhomogeneous fluids, etc.

Differential Pressure—the difference in pressure between two locations in space.

Time Domain Viscometry—quantitatively measuring the viscosity of a fluid by correlating the change in pressure (the range, or dependent variable) with respect to time (the domain, or independent variable). Time derivatives of pressure may be evaluated to elicit slopes, time constants, etc.; non-isovolumetric elements may be incorporated. Viscosity and/or flow may be quantitatively measured.

Differential Viscometry—ratiometrically determining the viscosity of a fluid (of unknown viscosity) by dividing a measured parameter (e.g., slope, time constant, pressure/time, pressure, etc.) by the same parameter of a fluid of known viscosity.

Aspirate (noun)—any fluid, liquid, solid, slurry or heterogeneous matter transferred through a conduit or catheter; also the contents of the conduit or catheter.

Aspirate or aspirating (verb)—employ (ing) differential pressure to transfer any fluid, liquid, solid, gas, vapor, slurry or heterogeneous matter through a conduit or catheter. Sources of differential pressure include: pumps, evacuated reservoirs, syringes, compliance chambers, atmospheric pressure, phase change, gravity, etc.

Aspiration or Positive Aspiration—The net removal of fluid from any reservoir including the patient vascular system; net mass transfer is inflow into the distal aperture of the catheter.

Source of Aspiration—any fluid transfer system that may cause continuous, pulsatile, interrupted, unsteady or steady fluid flow within a conduit or catheter. Relevant examples include: liquid pump, evacuated reservoir, syringe, etc.

Neutral or Isovolumetric Aspiration—Any combination of aspiration and infusion such that there is negligible net mass transfer into or out of the catheter. Also zero net aspiration resulting from zero differential pressure or a clogged catheter.

Negative aspirationInfusion of extracorporeal liquid at a rate that exceeds the aspiration rate. Negative aspiration may result from (1) reversal of the rotational direction of a liquid or aspirate pump, (2) advancing the plunger of a syringe, (3) operation of an infusion system, e.g., pressurized reservoir, infusion pump, etc.

Aspirate Characteristic or Fluid Characteristic—Attribute classification of aspirate or any fluid into subsets by any logical means, including mathematical evaluation, statistical inference or other algorithm. Example aspirate characteristics include: blood, saline, thrombus, SAE 30 motor oil, SAE 0W40 motor oil, clot and clog, etc.

Controlled Source of Differential Pressure—any setpoint controlled system that causes fluid to flow within a catheter. Examples include the shaft speed of a pump (0%, 10%, 20%, 30% . . . 100% of full speed) or an evacuated reservoir operating at variable vacuum level (0 mmHg, 10 mmHg, 20 mmHg, 25 mmHg), a syringe with the plunger subjected to force, etc.

Liquid Pump or Aspirate Pump—a liquid pump in fluid communication with a catheter lumen which may be operable to create flow. Bi-directional aspirate pumps may be operable in either the positive aspiration or negative aspiration directions. Operable to generate a differential pressure that causes fluid flow in either direction through the catheter. Example: setpoint-controlled peristaltic pump, capable of generating suction head exceeding approximately 20 inHg and pressure exceeding approximately 40 psi. Rotational speed range is approximately 0 RPM to 12,000 RPM (0 Hz to 200 Hz).

Reservoir—Any supply, source or sink of fluid; herein also any open or closed structure which may contain, retain or constrain fluid.

Infusion Pump—a liquid pump that is in fluid communication with a catheter lumen which may typically operate to create flow in the infusion direction. Example: peristaltic pump or piston pump, capable of pressures ranging from 3 psi to 10,000 psi. Rotational speed range is approximately 6 RPM to 12,000 RPM (0.1 Hz to 200 Hz).

Setpoint—The desired value of a control output, e.g., pump speed, vacuum, pressure or temperature. Herein also, the analog or digital output, from system controller, that changes the magnitude of the controlled output.

Update—The act of refreshing a control output (e.g., setpoint, thrombectomy operating mode, aspirate characteristic) to either a new or unchanged value. Control outputs are updated periodically and not necessarily simultaneous with any other event.

Thrombus—Any coalescence of blood or tissue components which remains attached to the vascular system. Herein, thrombus also includes mobile emboli (detached thrombi) as a result of any phenomena including a thrombectomy procedure. Mobile emboli, aspirated by catheter are herein also considered thrombus or thrombi. The composition of thrombus may include: clotted blood, proteinaceous and/or fatty masses, etc.

Thrombectomy Operating Mode—Any mode of operating a thrombectomy system comprising setpoint control of at least one system that effects characteristic flow regimes. Examples include: (1) viscometric inflow sampling, (2) intermediate aspiration (intermediate vacuum), (3) maximum aspiration (maximum vacuum), (4) negative aspiration ("reverse flow"), (5) calibration, etc. Thrombectomy operating modes may also include any temporal combination of the above listed examples, e.g., maximum aspiration interspersed with viscometric inflow sampling and/or negative aspiration.

Homogeneous data—process data, e.g., pressure, viscosity, etc., from measurements conducted upon homogeneous fluid samples or aliquots which exhibit approximately constant properties with respect to time, e.g., a continuous stream of saline or blood. Viscosity may remain approximately constant, with respect to samples or aliquots collected over a period of time, for homogeneous data.

Inhomogeneous data—process data, e.g., viscometric, from measurements conducted upon inhomogeneous fluid samples or aliquots which change with time, e.g., a saline aliquot, followed by a blood aliquot, followed by a thrombus aliquot, followed by a SAE30 motor oil aliquot, etc. Viscosity may vary with respect to time for inhomogeneous data.

Reference Data—data which may be externally defined and which may be accessed through databases, memory, storage, etc.

Calibration Data—data which may be collected upon samples or aliquots of known intensive, extensive or physical properties. Calibration data may be homogeneous. Calibration data may be collected during a thrombectomy procedure.

Patient Data—data which may be collected upon samples or aliquots of known or unknown intensive, extensive or physical properties. Homogeneous patient data may also be calibration data; patient data may be collected during a thrombectomy procedure.

Process Data—data which may be collected at a generally stationary location while process fluid passes one or more sensors. Fluctuations in process data may be attributed to fluids which exhibit spatial inhomogeneities which manifest as temporal inhomogeneities. Calibration and patient data may be process data.

Variable Data—quantitative information which is typically continuous (subject to the resolution of the instrumentation); mathematical analyses (including statistical) may readily be performed upon variable data. Also called measurement data. Variable data may be transformed or converted to attribute data in a degenerative process.

Attribute Data—qualitative information which falls into discrete categories; mathematical operations and analyses generally may not be performed upon attribute data of small sample size. Also called go/no-go or yes/no data. Attribute data generally may not be converted or transformed to variable data for small sample size.

Viscometric Inflow Sampling—thrombectomy operating mode wherein an objective may be monitoring the aspirate viscosity for data indicative of thrombus within or obstructing flow to the catheter; preferred embodiments of viscometric inflow sampling may minimize blood loss.

Sample Size (statistics)—the number of participants or observations included in a study.

Units or Units of Measure—dimensioned combinations of base units (e.g., mass, force, length, time, temperature, etc.) which may sufficiently define any intensive or extensive properties of matter. Relevant intensive properties (and a representative unit) include: pressure (Pa) and viscosity (cP); relevant extensive properties include flow rate (cc/s), volume (cc) and time(s).

Unit Conversion (Factor)—a ratio that expresses how many of one unit are equal to another unit. Example: convert 1 atmosphere to pascals (Pa); the conversion is from one unit of pressure to another unit of pressure.

$$1\text{ atm}\times\left(\frac{101{,}000\text{ Pa}}{1\text{ atm}}\right)=101{,}000\text{ Pa}$$

Set of Dimensions—The combination of base units of any measurement or parameter. Herein, in FLT (force, length, time) dimensions, pressure has the dimensions of $[FL^{-2}]$, an example unit is 1 Pascal (1 Pa)≡1 $N/m^2$ and dynamic viscosity (p) has the dimensions of $[FL^{-2}T]$, and example units are 1 Pa·s=1,000 cP. The example unit of force is newton (N), the unit of length is meter (m), the unit of time is second(s) and cP is a derived unit or engineering unit which exhibits the convenient physical property that $\mu_{water}\approx 1$.

Coordinate Transformation—A mathematical or graphic process of obtaining a modified set of coordinates by performing some nonsingular operation on the coordinate axes, such as rotation, scaling or translation.

Data Set—any N×M matrix or array of data, where N=>1 and M=>1; where N and M are positive integers, at least one of which is greater than 1. The data may be organized by row and column. A representative example is a 4×2 matrix with 4 values of pressure in the first column and 4 values of time in the second column. A 1×1 data set is a single data value, such as viscosity, flow, pressure or time.

Measure—ascertain the size, amount, or degree of (something) by using an instrument or device marked in standard units or by comparing it with an object of known size. Measurements generate variable data in characteristic units (e.g., meters, Newtons, volumetric flow in cc/second, viscosity in Pa·seconds, etc.).

Monitor—observe and check the progress or quality (of something) over a period of time; keep under systematic review. Monitors generate attribute data with no characteristic units or dimensions (e.g., low flow, high flow, thrombus, clot, clog, high viscosity, low viscosity, etc.).

Cavitation—Cavitation is the process whereby pressure variations in a liquid can, in a short period of time, cause countless small cavities to form and then implode. Cavitation is destructive to tissue (e.g., blood, thrombus, etc.) in part due to the localized heat transfer and pressure shock of the collapsing vapor bubble; the duration of a cavitation event may be fractions of a second (range of approximately 1 ns to 1 s) for a vapor cavity to form, grow and collapse by condensation. Cavitation may be observed in high-speed rotating equipment such as turbomachinery or a boat propeller; cavitation may also be observed when a high-velocity jet of liquid is discharged in to a fluid reservoir. Some residual gas or vapor pockets may exist after a cavitation event, however the preponderance of the vapor is returned to the liquid phase through condensation. An ultrasonic cleaner is an example of cavitation cleaning.

Boiling point—The boiling point of a liquid is the temperature at which its vapor pressure is equal to the ambient or local pressure. A liquid boils when the ambient pressure is equal to (or less than) the vapor pressure. Suction thrombectomy systems may boil liquid (wherein a significant fraction of the vapor does not return to the liquid phase) or cavitate liquid (wherein a significant fraction of the vapor returns to the liquid phase). Boiling and cavitation may be used interchangeable herein.

Time-Domain Calculations—Herein, calculations employing differential and/or integral calculus, in time domain, upon quantities of a first set of dimensions and units which generate quantities of a second set of dimensions and units. Time-domain calculations may be executed by means including: analytical solutions, numerical solutions, computational solutions, etc.

The following referencing numbers are used in this disclosure:

| | |
|---|---|
| 10 | vacuum reservoir |
| 20 | vacuum valve |
| 30 | compliance chamber |
| 40 | catheter |
| 50 | patient body |
| 60 | ambient atmosphere |
| 70 | pressure sensor |
| 100 | peristaltic pump |
| 110 | voltage source |
| 115 | pump housing |
| 120 | switch |
| 125 | rotor |
| 130 | capacitor |
| 130 | roller |
| 140 | variable resistor |
| 142 | inlet pressure |
| 143 | inlet cavity |
| 145 | inlet port |
| 150 | neutral charge |
| 152 | outlet pressure |
| 153 | isolated cavity |
| 155 | outlet port |
| 160 | outlet cavity |
| 165 | pressure transducer |
| 170 | discharge |
| 210 | pulsed trace |
| 220 | stopped slope trace |
| 230 | Pmin |
| 250 | partial charge |
| 250 | stopped slope |
| 270 | negative running slope |
| 280 | positive running slope |
| 285 | FIG. 16b data |
| 290 | P0 |
| 310 | upper bound |
| 320 | lower bound |
| 330 | running angle 50 |
| 335 | Pmin 50 |
| 340 | running angle 100 |
| 345 | Pmin 100 |
| 350 | fully charged |
| 350 | running angle 200 |
| 360 | running angle 300 |
| 365 | Pmin300 |
| 368 | 0.368 line |
| 370 | nominal pressure |
| 410 | water |
| 420 | vinegar |
| 430 | creamer |
| 440 | cream hot |
| 450 | vegetable oil |
| 460 | cream cold |
| 470 | ATF |
| 480 | column 1 |
| 485 | row 1 |
| 510 | saline drop line |
| 515 | saline slope line |

| | |
|---|---|
| 520 | blood drop line |
| 525 | blood slope line |
| 530 | thrombus drop line |
| 535 | thrombus slope line |
| 550 | saline trace |
| 560 | blood trace |
| 600 | system controller |
| 639 | clinician input |
| 641 | USB BT I/O |
| 643 | memory |
| 645 | program |
| 647 | input |
| 649 | output |
| 651 | microprocessor |
| 653 | drivers, amplifiers, relays |
| 655 | video display |
| 657 | graphics driver |
| 659 | tone generator |
| 661 | speaker |
| 700 | calculate tau subroutine |
| 702 | start |
| 704 | open valve |
| 706 | measure PO |
| 708 | close valve |
| 710 | wait delta t |
| 712 | measure Pi |
| 714 | calculate tau |
| 716 | repeat n times |
| 718 | exit |
| 800 | thrombectomy flowchart |
| 801 | calibration |
| 802 | start |
| 803 | viscometric inflow sampling |
| 804 | catheter in saline |
| 806 | catheter in blood |
| 808 | confirm plausibility |
| 810 | initialize j |
| 812 | reposition catheter |
| 814 | call tau subroutine |
| 816 | tau > blood |
| 818 | tau 1000x blood |
| 820 | tau 100x blood |
| 822 | tau 10x blood |
| 824 | tau 1.1x blood |
| 830 | clog clearing |
| 832 | clot clearing |
| 834 | thrombus routine 1 |
| 836 | thrombus routine 2 |
| 838 | no aspiration |
| 840 | increment j |
| 850 | liquid pump |
| 855 | valve |
| 860 | manifold |
| 865 | spring compliance chamber |
| 870 | waste reservoir |
| 875 | spring |
| 880 | piston |
| 885 | cylinder |
| 887 | flow direction |
| 888 | decreasing pressure |
| 889 | pump operating |
| 890 | piston movement |
| 891 | increasing pressure |
| 900 | compliance chamber |
| 910 | inlet/outlet |
| 920 | nominal |
| 930 | neutral |
| 940 | contracted |
| 1000 | syringe compliance chamber |
| 1010 | barrel |
| 1020 | plunger |
| 1030 | spring |
| 1040 | actuator |
| 1045 | actuator rod |
| 1050 | waste tube |
| 1060 | check valve |
| 1070 | encoder |
| 1080 | encoder rod |

| | |
|---|---|
| 1090 | liquid |
| 1095 | vapor |

What is claimed is:

1. An apparatus for transporting a fluid and determining a transport property of the fluid, the apparatus comprising:

a conduit configured to receive a fluid, the conduit having a nominal volume while at a nominal pressure, the conduit including a boundary that is movable between:

(i) a nominal dimension associated with the nominal volume and the nominal pressure, and (ii) a displaced dimension associated with a displacement volume and a pressure that is not the nominal pressure;

a boundary actuator configured to place the boundary in the displaced dimension;

a pressure sensor in fluid communication with the conduit and configured to measure a pressure of the fluid; and a controller operatively coupled to the boundary actuator and the pressure sensor, the controller configured to:

(a) operate the boundary actuator to place the boundary in the displaced dimension, (b) obtain a first pressure measurement at a first time and a second pressure measurement at a second time while the boundary relaxes from the displaced dimension toward the nominal dimension, (c) determine a pressure decay rate from the first and second pressure measurements, (d) compute a time constant from the pressure decay rate, and (e) determine the transport property of the fluid as a function of the computed time constant.

2. The apparatus of claim 1, wherein the transport property comprises a viscosity of the fluid.

3. The apparatus of claim 2, wherein the viscosity is determined from an algebraic comparison of the computed time constant and a predetermined time constant.

4. The apparatus of claim 1, wherein the transport property comprises a volumetric flow rate of the fluid.

5. The apparatus of claim 4, wherein the volumetric flow rate is determined from the computed time constant and a time-dependent hydraulic model.

6. The apparatus of claim 4, wherein the volumetric flow rate is determined from an algebraic comparison of the computed time constant and a predetermined time constant.

7. The apparatus of claim 1, further comprising a memory containing at least one stored data block corresponding to a reference fluid, the data block containing at least one of a predetermined time constant, a predetermined pressure slope, a predetermined pressure integral, or a predetermined viscosity value associated with the reference fluid.

8. The apparatus of claim 7, wherein the reference fluid is selected from water, saline, blood, thrombus, clot, clog, alcohol, vinegar, creamer, vegetable oil, motor oil, automatic transmission fluid, calibration standard and paint.

9. The apparatus of claim 7, wherein the memory is configured with at least three data blocks corresponding to at least three reference fluids; and the controller is configured to determine if a viscosity of the fluid is greater than the viscosity of a first reference fluid by determining if the computed time constant is greater than the predetermined time constant of the first reference fluid.

10. The apparatus of claim 9, wherein the controller is configured to determine if the viscosity of the fluid is less than the viscosity of a second reference fluid by determining if the computed time constant is less than the predetermined time constant of the second reference fluid; the apparatus thereby determining that the viscosity of the fluid is intermediate between the viscosity of the first reference fluid and the viscosity of the second reference fluid.

11. The apparatus of claim 9, wherein the conduit is configured to receive the first reference fluid; and wherein the controller is configured to store, to the first data block corresponding to the first reference fluid, at least one of the computed time constant, a computed slope of pressure, a computed integral of pressure, or a viscosity value of the first reference fluid.

12. The apparatus of claim 1, wherein the boundary is an elastomer separating the internal volume of the conduit from atmospheric pressure.

13. The apparatus of claim 12, wherein the boundary actuator comprises a moving roller configured to apply a surface contact force to the boundary.

14. The apparatus of claim 1, wherein the boundary is a piston slidingly engaged in a cylinder.

15. The apparatus of claim 14, wherein the piston is biased by a spring.

16. The apparatus of claim 1, wherein the boundary actuator comprises a vacuum valve fluidically coupled to an evacuated reservoir.

17. A method of quantitatively determining a transport property of a fluid, the method comprising:

providing a conduit configured to receive a fluid, the conduit having a nominal volume while at a nominal pressure, the conduit including a boundary that is movable between:

(i) a nominal dimension associated with the nominal volume and the nominal pressure, and (ii) a displaced dimension associated with a displacement volume and a pressure that is not the nominal pressure;

using a boundary actuator to place the boundary in the displaced dimension;

obtaining a first pressure measurement at a first time and a second pressure measurement at a second time while the boundary relaxes from the displaced dimension toward the nominal dimension;

determining a pressure decay rate from the first and second pressure measurements;

computing a time constant from the pressure decay rate; and determining the transport property of the fluid as a function of the computed time constant.

18. The method of claim 17, wherein the transport property comprises a volumetric flow rate of the fluid.

19. The method of claim 18, wherein the volumetric flow rate is determined from the computed time constant and a time-dependent hydraulic model.

20. The method of claim 18, wherein the volumetric flow rate is determined from an algebraic comparison of the computed time constant and a predetermined time constant.

* * * * *